(12) United States Patent
Hosse et al.

(10) Patent No.: US 11,365,232 B2
(45) Date of Patent: *Jun. 21, 2022

(54) INTERLEUKIN-2 FUSION PROTEINS AND USES THEREOF

(71) Applicant: Roche Glycart AG, Schlieren (CH)

(72) Inventors: Ralf Hosse, Cham (CH); Christian Klein, Bonstetten (CH); Ekkehard Moessner, Kreuzlingen (CH); Laurence Bernard Peterson, Cambridge (GB); Pablo Umana, Wollerau (CH); Linda Wicker, Cambridge (GB)

(73) Assignee: Roche Glycart AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,141

(22) Filed: Feb. 5, 2020

(65) Prior Publication Data

US 2020/0172591 A1   Jun. 4, 2020

Related U.S. Application Data

(60) Division of application No. 15/695,899, filed on Sep. 5, 2017, now Pat. No. 10,562,949, which is a division of application No. 14/967,019, filed on Dec. 11, 2015, now abandoned, which is a continuation of application No. 13/960,149, filed on Aug. 6, 2013, now abandoned.

(60) Provisional application No. 61/681,676, filed on Aug. 10, 2012.

(51) Int. Cl.
*A61K 38/20* (2006.01)
*C07K 14/55* (2006.01)
*C07K 16/46* (2006.01)
*C07K 16/18* (2006.01)

(52) U.S. Cl.
CPC .......... *C07K 14/55* (2013.01); *A61K 38/2013* (2013.01); *C07K 16/18* (2013.01); *C07K 16/46* (2013.01); *C07K 2317/21* (2013.01); *C07K 2319/00* (2013.01); *C07K 2319/30* (2013.01)

(58) Field of Classification Search
CPC ................................................ A61K 38/2013
See application file for complete search history.

(56) References Cited

U.S. PATENT DOCUMENTS

| | | | |
|---|---|---|---|
| 5,650,150 A | 7/1997 | Gillies | |
| 6,955,807 B1 | 10/2005 | Shanafelt et al. | |
| 8,969,526 B2 | 3/2015 | Baehner et al. | |
| 9,266,938 B2 | 2/2016 | Ast et al. | |
| 9,447,159 B2 | 9/2016 | Ast et al. | |
| 10,184,009 B2 | 1/2019 | Ast et al. | |
| 10,202,464 B2 | 2/2019 | Ast et al. | |
| 2004/0175357 A1 | 9/2004 | Shanafelt et al. | |
| 2004/0229338 A1 | 11/2004 | King et al. | |
| 2010/0021477 A1 | 1/2010 | Tsui et al. | |
| 2010/0260765 A1 | 10/2010 | Barry et al. | |
| 2011/0274650 A1 | 11/2011 | Gavin et al. | |
| 2012/0251531 A1 | 10/2012 | Baehner et al. | |
| 2013/0195795 A1 | 8/2013 | Gavin et al. | |
| 2015/0218260 A1 | 8/2015 | Klein et al. | |
| 2015/0239981 A1 | 8/2015 | Baehner et al. | |
| 2016/0090407 A1 | 3/2016 | Hosse et al. | |
| 2016/0208017 A1 | 7/2016 | Ast et al. | |
| 2016/0263240 A1 | 9/2016 | Ast et al. | |
| 2017/0137530 A1 | 5/2017 | Baehner et al. | |
| 2018/0009868 A1 | 1/2018 | Hosse et al. | |

FOREIGN PATENT DOCUMENTS

| | | |
|---|---|---|
| WO | 85/00817 | 2/1985 |
| WO | 99/43713 | 9/1999 |
| WO | 99/60128 A1 | 11/1999 |
| WO | 2003/048334 A2 | 6/2003 |
| WO | 2005/007121 A2 | 1/2005 |
| WO | 2005/086798 | 9/2005 |
| WO | 2006/058077 | 6/2006 |
| WO | 2008/003473 | 1/2008 |
| WO | 2009/061853 A2 | 5/2009 |
| WO | 2009/135615 A2 | 11/2009 |
| WO | 2009/135615 A3 | 11/2009 |
| WO | 2009/135615 A8 | 11/2009 |
| WO | 2010/085495 A1 | 7/2010 |
| WO | 2012/062228 A2 | 5/2012 |
| WO | 2012/107417 | 8/2012 |
| WO | 2012/107417 A1 | 8/2012 |
| WO | 2012/123381 A1 | 9/2012 |
| WO | 2012/130831 A1 | 10/2012 |
| WO | 2012/146628 | 11/2012 |
| WO | 2012/146628 A1 | 11/2012 |
| WO | 2012/178137 A1 | 12/2012 |

(Continued)

OTHER PUBLICATIONS

(Extended European Search Report for European Patent Application No. 18201416.7 dated May 15, 2019).

Armour et al., "Recombinant human IgG molecules lacking Fcÿ receptor I binding and monocyte triggering activities" Eur. J. Immunol. 29:2613-2634 (May 10, 1999).

Bork et al., "Powers and Pitfalls in Sequence Analysis: the 70% Hurdle" Genorme Res. 10:398-400 ( 2000).

(Continued)

*Primary Examiner* — Prema M Mertz

(74) *Attorney, Agent, or Firm* — Jonathan P. Aumais

(57) ABSTRACT

The present invention generally relates to fusion proteins of immunoglobulins and interleukin-2 (IL-2). In addition, the present invention relates to polynucleotides encoding such fusion proteins, and vectors and host cells comprising such polynucleotides. The invention further relates to methods for producing the fusion proteins of the invention, and to methods of using them in the treatment of disease.

6 Claims, 17 Drawing Sheets

Specification includes a Sequence Listing.

(56) References Cited

FOREIGN PATENT DOCUMENTS

| WO | 2014/023752 | A1 | 2/2014 |
|----|-------------|-----|--------|
| WO | 2014/153063 | A1 | 9/2014 |
| WO | 2014/153111 | A2 | 9/2014 |
| WO | 2016/022671 | A1 | 2/2016 |

OTHER PUBLICATIONS

Bowie, J. et al., "Deciphering the message in protein sequences: tolerance to amino acid substitutions" Science 247(4948):1306-1310 (Mar. 16, 1990).

Brandenburg et al., "IL-2 induces in vivo suppression by CD4\\\superscript:+\\\CD25\\\superscript:+\\\FoXp3\\\superscript:+\\\ regulatory T cells" Eur. J. Immunol. 38:1643-1653 ( 2008).

Burgess et al., "Possible dissociation of the heparin-binding and mitogenic activities of heparin-binding (Acidic Fibroblast) growth factor-1 from its receptor-binding activities by site-directed mutagenesis of a single lysine residue" Journal of Cell Biology 111:2129-2138 (1990).

International Search Report and Written Opinion on patentability for International Patent Application No. PCT/EP2015/052312 dated Jun. 2, 2015.

De La Rosa et al., "Interleukin-2 is essential for CD4\\\superscript:+\\\CD25\\\superscript:+\\\regulatory T cell function" Eur. J. Immunol. 34:2480-2488 ( 2004).

Gillies et al., "Improving the Efficacy of Antibody-Interleukin 2 Fusion Proteins by Reducing Their Interaction with Fc Receptors," Cancer Research, vol. 59(9), pp. 2159-2166 (1999).

Harvill et al, "An IgG3-IL2 fusion protein activates complement, binds FcTRI, generates LAK activity and shows enhanced binding to the high affinity IL-2R," Immunotechnology, vol. 1(2), pp. 95-105 (1995).

Helguera et al., "Vaccination with novel combinations of anti-HER2/neu cytokines fusion proteins and soluble protein antigen elicits a protective immune response against HER2/neu expressing tumors," Vaccine 24 (2006) 304-316.

Kim et al., "Immunoglobulin-Cytokine Fusion Molecules: The New Generation of Immunomodulating Agents," Transplantation Proceedings, 30, 4031-4036 (1998).

Kunzendorf et al., "Suppression of Cell-mediated and Humoral Immune Responses by an Interleukin-2-Immunoglobulin Fusion Protein in Mice" J. Clin. Invest. 97(5): 1204-1210 (Mar. 1996).

Lazar et al., "Transforming Growth Factor α: Mutation of Aspartic Acid 47 and Leucine 48 Results in Different Biological Activities" Molecular and Cellular Biology 8(3):1247-1252 (Mar. 1988).

Presta et al., "Molecular engineering and design of therapeutic antibodies" Current Opinion in Immunology 20:460-470 ( 2008).

Shields et al., "High Resolution Mapping of the Binding Site on Human IgG1 for FcγRI, FcγRII, FcγRIII, and FcRn and design of IgG1 variants with improved binding to the RcγR" J Biol Chem 276(9):6591-6604 (Mar. 2, 2001).

Strohl, R., "Optimization of Fc-mediated effector functions of monoclonal antibodies" Current Opinion in Biotechnology 20(6):685-691 ( 2009).

The International Search Report and Written Opinion, dated Nov. 4, 2013, in the corresponding PCT Patent Application No. PCT/EP2013/066516.

Wang et al., "Structure of the quaternary complex of interleukin-2 with its α, beta, and γc receptors" Science 310(5751):1159-1163 ( 2005).

SEQUENCE LISTING

```
<160> NUMBER OF SEQ ID NOS: 47

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 399
<212> TYPE: DNA
<213> ORGANISM: Artificial Sequence
<220> FEATURE:
<223> OTHER INFORMATION: Wild-type human IL-2

<400> SEQUENCE: 2
gcacctactt caagttctac aaagaaaaca cagctacaac tggagcattt actgctggat        60
ttacagatga ttttgaatgg aattaataat tacaagaatc ccaaactcac caggatgctc       120
acatttaagt tttacatgcc caagaaggcc acagaactga aacatcttca gtgtctagaa       180
gaagaactca aacctctgga ggaagtgcta aatttagctc aaagcaaaaa ctttcactta       240
agacccaggg acttaatcag caatatcaac gtaatagttc tggaactaaa gggatctgaa       300
acaacattca tgtgtgaata tgctgatgag acagcaacca ttgtagaatt tctgaacaga       360
tggattacct tttgtcaaag catcatctca acactgact                              399
```

<210> SEQ ID NO 3
<211> LENGTH: 133
<212> TYPE: PRT
<213> ORGANISM: Artificial Sequence
<220> FEATURE:
<223> OTHER INFORMATION: Wild-type human IL-2 (C125A)

<400> SEQUENCE: 3

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130
```

<210> SEQ ID NO 4
<211> LENGTH: 399
<212> TYPE: DNA
<213> ORGANISM: Artificial Sequence
<220> FEATURE:
<223> OTHER INFORMATION: Wild-type human IL-2 (C125A) (1)

<400> SEQUENCE: 4

```
gctcctacat cctccagcac caagaaaacc cagctccagc tggaacatct cctgctggat      60
ctgcagatga tcctgaacgg catcaacaac tacaagaacc ccaagctgac ccggatgctg     120
accttcaagt tctacatgcc caagaaggcc accgagctga acatctgca gtgcctggaa     180 gaggaactga agcctctgga agaggtgctg aacctggccc agtccaagaa cttccacctg     240
aggcctcggg acctgatctc caacatcaac gtgatcgtgc tggaactgaa gggctccgag     300
acaaccttca tgtgcgagta cgccgacgag acagctacca tcgtggaatt tctgaaccgg     360
tggatcacct tcgcccagtc catcatctcc accctgacc                            399
```

<210> SEQ ID NO 5
<211> LENGTH: 399
<212> TYPE: DNA
<213> ORGANISM: Artificial Sequence
<220> FEATURE:
<223> OTHER INFORMATION: Wild-type human IL-2 (C125A) (2)

<400> SEQUENCE: 5

```
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa     180 gaagaactca aacctctgga ggaagtgcta aatttagctc aaagcaaaaa ctttcactta     240
```

```
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct ttgcccaaag catcatctca acactgact                           399

<210> SEQ ID NO 6
<211> LENGTH: 399
<212> TYPE: DNA
<213> ORGANISM: Artificial Sequence
<220> FEATURE:
<223> OTHER INFORMATION: Wild-type human IL-2 (C125A) (3)

<400> SEQUENCE: 6
gctcctacta gcagctccac caagaaaacc cagctccagc tggaacatct gctgctggat     60
ctgcagatga tcctgaacgg catcaacaac tacaagaacc ccaagctgac ccggatgctg    120
accttcaagt tctacatgcc caagaaggcc accgaactga acatctgca gtgcctggaa    180 gaggaactga gcctctggag agaggtgctg aacctggccc agagcaagaa cttccacctg    240
aggcccaggg acctgatcag caacatcaac gtgatcgtgc tggaactgaa gggcagcgag    300
acaaccttca tgtgcgagta cgccgacgag acagccacca tcgtggaatt tctgaaccgg    360
tggatcacct tcgcccagag catcatcagc accctgaca                           399

<210> SEQ ID NO 7
<211> LENGTH: 399
<212> TYPE: DNA
<213> ORGANISM: Artificial Sequence
<220> FEATURE:
<223> OTHER INFORMATION: Wild-type IL-2 (C125A) (4)

<400> SEQUENCE: 7
gcacctactt caagttctac aaagaaaaca cagctacaac tggagcattt actgctggat     60
ttacagatga ttttgaatgg aattaataat tacaagaatc ccaaactcac caggatgctc    120
acatttaagt tttacatgcc caagaaggcc acagaactga acatcttca gtgtctagaa    180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct ttgcccaaag catcatctca acactgact                           399

<210> SEQ ID NO 8
<211> LENGTH: 227
<212> TYPE: PRT
<213> ORGANISM: Homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 115
<212> TYPE: PRT
<213> ORGANISM: Artificial Sequence
<220> FEATURE:
<223> OTHER INFORMATION: DP47GS VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser
        115

<210> SEQ ID NO 10
<211> LENGTH: 345
<212> TYPE: DNA
<213> ORGANISM: Artificial Sequence
<220> FEATURE:
<223> OTHER INFORMATION: DP47GS VH

<400> SEQUENCE: 10
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctgagtg gtctcagct attagtggta gtggtggtag cacatactac      180
gcagactccg tgaagggccg gttcaccatc tccagagaca attccaagaa cacgctgtat     240

```
ctgcagatga acagcctgag agccgaggac acggccgtat attactgtgc gaaaggcagc    300
ggatttgact actggggcca aggaaccctg gtcaccgtct cgagt                    345
```

<210> SEQ ID NO 11
<211> LENGTH: 108
<212> TYPE: PRT
<213> ORGANISM: Artificial Sequence
<220> FEATURE:
<223> OTHER INFORMATION: DP47GS VL

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 12
<211> LENGTH: 324
<212> TYPE: DNA
<213> ORGANISM: Artificial Sequence
<220> FEATURE:
<223> OTHER INFORMATION: DP47GS VL

<400> SEQUENCE: 12

```
gaaatcgtgt taacgcagtc tccaggcacc ctgtctttgt ctccagggga agagccacc     60 ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagtatggta gctcaccgct gacgttcggc    300
caggggacca agtggaaat caaa                                            324
```

<210> SEQ ID NO 13
<211> LENGTH: 592
<212> TYPE: PRT
<213> ORGANISM: Artificial Sequence
<220> FEATURE:
<223> OTHER INFORMATION: DP47GS HC(Fc knob,P329G LALA)-IL2

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480
```

```
Gln Met Ile Leu Asn Gly Ile Asn Asn Tyr Lys Asn Pro Lys Leu Thr
                485                 490                 495
Arg Met Leu Thr Phe Lys Phe Tyr Met Pro Lys Lys Ala Thr Glu Leu
            500                 505                 510
Lys His Leu Gln Cys Leu Glu Glu Glu Leu Lys Pro Leu Glu Glu Val
        515                 520                 525
Leu Asn Leu Ala Gln Ser Lys Asn Phe His Leu Arg Pro Arg Asp Leu
    530                 535                 540
Ile Ser Asn Ile Asn Val Ile Val Leu Glu Leu Lys Gly Ser Glu Thr
545                 550                 555                 560
Thr Phe Met Cys Glu Tyr Ala Asp Glu Thr Ala Thr Ile Val Glu Phe
                565                 570                 575
Leu Asn Arg Trp Ile Thr Phe Ala Gln Ser Ile Ile Ser Thr Leu Thr
            580                 585                 590

<210> SEQ ID NO 14
<211> LENGTH: 1776
<212> TYPE: DNA
<213> ORGANISM: Artificial Sequence
<220> FEATURE:
<223> OTHER INFORMATION: DP47GS HC(Fc knob,P329G LALA)-IL2

<400> SEQUENCE: 14
gaggtgcaat tgttggagtc tgggggaggc ttggtacagc ctgggggtc cctgagactc      60
tcctgtgcag cctccggatt cacctttagc agttatgcca tgagctgggt ccgccaggct    120
ccagggaagg gctgagtg gtctcagct attagtggta gtggtggtag cacatactac       180
gcagactccg tgaagggccg gttcaccatc tccagagaca attccaagaa cacgctgtat    240
ctgcagatga acagcctgag agccgaggac acggccgtat attactgtgc gaaaggcagc    300
ggatttgact actggggcca aggaaccctg gtcaccgtct cgagtgctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagctgcag gggaccgtc agtcttcctc     720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgccccatc gagaaaacca tctccaaagc caaagggcag    1020
ccccgagaac acaggtgta cacccctgccc catgcccggg atgagctgac caagaaccag    1080
gtcagcctgt ggtgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtggcggcgg aggctccgga ggcggaggtt ctggaggcgg aggctccgca    1380
cctacttcaa gttctacaaa gaaaacacag ctacaactgg agcatttact gctggattta    1440
```

```
cagatgattt tgaatggaat taataattac aagaatccca aactcaccag gatgctcaca   1500
tttaagtttt acatgcccaa gaaggccaca gaactgaaac atcttcagtg tctagaagaa   1560
gaactcaaac ctctggagga agtgctaaat ttagctcaaa gcaaaaactt tcacttaaga   1620
cccagggact taatcagcaa tatcaacgta atagttctgg aactaaaggg atctgaaaca   1680
acattcatgt gtgaatatgc tgatgagaca gcaaccattg tagaatttct gaacagatgg   1740
attacctttg cccaaagcat catctcaaca ctgact                             1776
```

<210> SEQ ID NO 15
<211> LENGTH: 445
<212> TYPE: PRT
<213> ORGANISM: Artificial Sequence
<220> FEATURE:
<223> OTHER INFORMATION: DP47GS HC(Fc hole, P329G LALA)

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 16
<211> LENGTH: 1335
<212> TYPE: DNA
<213> ORGANISM: Artificial Sequence
<220> FEATURE:
<223> OTHER INFORMATION: DP47GS HC(Fc hole, P329G LALA)

<400> SEQUENCE: 16
gaggtgcaat tgttggagtc tgggggaggc ttggtacagc ctgggggttc cctgagactc      60
tcctgtgcag cctccggatt cacctttagc agttatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggcagc     300
ggatttgact actggggcca aggaaccctg gtcaccgtct cgagtgctag caccaagggc     360
ccctccgtgt tccccctggc ccccagcagc aagagcacca gcggcggcac agccgctctg     420
ggctgcctgg tcaaggacta cttccccgag cccgtgaccg tgtcctggaa cagcggagcc     480
ctgacctccg gcgtgcacac cttccccgcc gtgctgcaga gttctggcct gtatagcctg     540
agcagcgtgg tcaccgtgcc ttctagcagc ctgggcaccc agacctacat ctgcaacgtg     600
aaccacaagc ccagcaacac caaggtggac aagaaggtgg agcccaagag ctgcgacaaa     660
actcacacat gcccaccgtg cccagcacct gaagctgcag gggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctcgg cgcccccatc gagaaaacca tctccaaagc caaagggcag    1020
ccccgagaac acaggtgtg cacctgcccc catcccggg atgagctgac caagaaccag    1080
gtcagcctct cgtgcgcagt caaaggcttc tatcccagcg acatcgccgt ggagtgggag    1140
agcaatgggc agccggagaa caactacaag accacgcctc ccgtgctgga ctccgacggc    1200
tccttcttcc tcgtgagcaa gctcaccgtg gacaagagca ggtggcagca ggggaacgtc    1260
```

```
ttctcatgct ccgtgatgca tgaggctctg cacaaccact acacgcagaa gagcctctcc    1320
ctgtctccgg gtaaa                                                     1335
```

<210> SEQ ID NO 17
<211> LENGTH: 592
<212> TYPE: PRT
<213> ORGANISM: Artificial Sequence
<220> FEATURE:
<223> OTHER INFORMATION: DP47GS HC (Fc wt, P329G LALA)-IL2

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590

<210> SEQ ID NO 18
<211> LENGTH: 1776
<212> TYPE: DNA
<213> ORGANISM: Artificial Sequence
<220> FEATURE:
<223> OTHER INFORMATION: DP47GS HC (Fc wt, P329G LALA)-IL2

<400> SEQUENCE: 18
gaggtgcaat tgttggagtc tgggggaggc ttggtacagc ctggggggtc cctgagactc       60
tcctgtgcag cctccggatt cacctttagc agttatgcca tgagctgggt ccgccaggct      120
ccagggaagg gctggagtg gtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gaaaggcagc      300
ggatttgact actggggcca aggaaccctg gtcaccgtct cgagtgctag caccaagggc      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagaaagttg agcccaaatc ttgtgacaaa      660
actcacacat gcccaccgtg cccagcacct gaagctgcag ggggaccgtc agtcttcctc      720

```
ttccccccaa acccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgcccccatc gagaaaacca tctccaaagc caagggcag   1020 ccccgagaac acaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtggcggcgg aggctccgga ggcggaggtt ctggaggcgg aggctccgca   1380
cctacttcaa gttctacaaa gaaaacacag ctacaactgg agcatttact gctggattta   1440
cagatgattt tgaatggaat taataattac aagaatccca aactcaccag gatgctcaca   1500
tttaagtttt acatgcccaa gaaggccaca gaactgaaac atcttcagtg tctagaagaa   1560
gaactcaaac ctctggagga agtgctaaat ttagctcaaa gcaaaaactt tcacttaaga   1620
cccagggact taatcagcaa tatcaacgta atagttctgg aactaaaggg atctgaaaca   1680
acattcatgt gtgaatatgc tgatgagaca gcaaccattg tagaatttct gaacagatgg   1740
attacctttg cccaaagcat catctcaaca ctgact                              1776
```

<210> SEQ ID NO 19
<211> LENGTH: 215
<212> TYPE: PRT
<213> ORGANISM: Artificial Sequence
<220> FEATURE:
<223> OTHER INFORMATION: DP47GS LC

<400> SEQUENCE: 19

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 20
<211> LENGTH: 645
<212> TYPE: DNA
<213> ORGANISM: Artificial Sequence
<220> FEATURE:
<223> OTHER INFORMATION: DP47GS LC

<400> SEQUENCE: 20

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatggta gctcaccgct gacgttcggc     300
caggggacca agtggaaat caaacgtacg gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgt                     645
```

<210> SEQ ID NO 21
<211> LENGTH: 466
<212> TYPE: PRT
<213> ORGANISM: Artificial Sequence
<220> FEATURE:
<223> OTHER INFORMATION: Human IL-2R-beta-Fc(hole) fusion protein

<400> SEQUENCE: 21

Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

-continued

```
Asn Ile Ser Trp Glu Ile Ser Gln Ala Ser His Tyr Phe Glu Arg His
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190

Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Cys
            355                 360                 365

Thr Leu Pro Pro Ser Arg Asp Glu Leu Thr Lys Asn Gln Val Ser Leu
        370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 22
<211> LENGTH: 1401
<212> TYPE: DNA
<213> ORGANISM: Artificial Sequence
<220> FEATURE:
<223> OTHER INFORMATION: Human IL-2R-beta-Fc(hole) fusion protein

<400> SEQUENCE: 22

```
atggacatga gggtcccccgc tcagctcctg ggcctcctgc tgctctggtt cccaggtgcc    60
aggtgtgcgg tgaatggcac ttcccagttc acatgcttct acaactcgag agccaacatc   120
tcctgtgtct ggagccaaga tgggctctg caggacactt cctgccaagt ccatgcctgg   180
```

```
ccggacagac ggcggtggaa ccaaacctgt gagctgctcc ccgtgagtca agcatcctgg      240
gcctgcaacc tgatcctcgg agccccagat tctcagaaac tgaccacagt tgacatcgtc      300
accctgaggg tgctgtgccg tgagggggtg cgatggaggg tgatggccat ccaggacttc      360
aagccctttg agaaccttcg cctgatggcc cccatctccc tccaagttgt ccacgtggag      420
acccacagat gcaacataag ctgggaaatc tcccaagcct ccactacttt gaaagacac       480 ctggagttcg aggcccggac gctgtcccca ggcacacct gggaggaggc ccccctgctg       540
actctcaagc agaagcagga atggatctgc ctggagacgc tcaccccaga cacccagtat      600
gagtttcagg tgcgggtcaa gcctctgcaa ggcgagttca cgacctggag ccctggagc       660 cagcccctgg ccttcagaac aaagcctgca gcccttggga aggacaccgg agctcaggac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtgcaccctg cccccatccc gggatgagct gaccaagaac    1140
caggtcagcc tctcgtgcgc agtcaaaggc ttctatccca gcgacatcgc cgtggagtgg    1200
gagagcaatg ggcagccgga gaacaactac aagaccacgc ctcccgtgct ggactccgac    1260
ggctccttct tcctcgtgag caagctcacc gtggacaaga gcaggtggca gcagggaac     1320 gtcttctcat gctccgtgat gcatgaggct ctgcacaacc actacacgca gaagagcctc    1380
tccctgtctc cgggtaaatg a                                              1401
```

<210> SEQ ID NO 23
<211> LENGTH: 492
<212> TYPE: PRT
<213> ORGANISM: Artificial Sequence
<220> FEATURE:
<223> OTHER INFORMATION: Human IL-2R-gamma-Fc(knob) fusion protein

<400> SEQUENCE: 23

```
Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140
```

```
Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
                180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 24
<211> LENGTH: 1479
<212> TYPE: DNA
<213> ORGANISM: Artificial Sequence
<220> FEATURE:
<223> OTHER INFORMATION: Human IL-2R-gamma-Fc(knob) fusion protein

<400> SEQUENCE: 24
atgttgaagc catcattacc attcacatcc ctcttattcc tgcagctgcc cctgctggga      60
gtggggctga acacgacaat tctgacgccc aatgggaatg aagacaccac agctgatttc     120
```
ttcctgacca ctatgcccac tgactccctc agtgtttcca ctctgcccct cccagaggtt        180
cagtgttttg tgttcaatgt cgagtacatg aattgcactt ggaacagcag ctctgagccc        240
cagcctacca acctcactct gcattattgg tacaagaact cggataatga taaagtccag        300
aagtgcagcc actatctatt ctctgaagaa atcacttctg ctgtcagtt gcaaaaaaag         360 gagatccacc tctaccaaac atttgttgtt cagctccagg acccacggga acccaggaga        420
caggccacac agatgctaaa actgcagaat ctggtgatcc cctgggctcc agagaaccta        480
acacttcaca aactgagtga atcccagcta gaactgaact ggaacaacag attcttgaac        540
cactgtttgg agcacttggt gcagtaccgg actgactggg accacagctg gactgaacaa        600
tcagtggatt atagacataa gttctccttg cctagtgtgg atgggcagaa acgctacacg        660
tttcgtgttc ggagccgctt aacccactc tgtggaagtg ctcagcattg gagtgaatgg         720
agccacccaa tccactgggg gagcaatact tcaaaagaga tcctttcct gtttgcattg         780 gaagccggag ctcaggacaa aactcacaca tgcccaccgt gcccagcacc tgaactcctg        840
gggggaccgt cagtcttcct cttccccca aaacccaagg acaccctcat gatctcccgg         900
acccctgagg tcacatgcgt ggtggtggac gtgagccacg aagaccctga ggtcaagttc        960
aactggtacg tggacggcgt ggaggtgcat aatgccaaga caaagccgcg ggaggagcag       1020
tacaacagca cgtaccgtgt ggtcagcgtc ctcaccgtcc tgcaccagga ctggctgaat       1080
ggcaaggagt acaagtgcaa ggtctccaac aaagccctcc cagcccccat cgagaaaacc       1140
atctccaaag ccaaagggca gccccgagaa ccacaggtgt acaccctgcc cccatgccgg       1200
gatgagctga ccaagaacca ggtcagcctg tggtgcctgg tcaaaggctt ctatcccagc       1260
gacatcgccg tggagtggga gagcaatggg cagccggaga acaactacaa gaccacgcct       1320
cccgtgctgg actccgacgg ctccttcttc ctctacagca agctcaccgt ggacaagagc       1380
aggtggcagc aggggaacgt cttctcatgc tccgtgatgc atgaggctct gcacaaccac       1440
tacacgcaga agagcctctc cctgtctccg ggtaaatga                              1479

<210> SEQ ID NO 25
<211> LENGTH: 219
<212> TYPE: PRT
<213> ORGANISM: Artificial Sequence
<220> FEATURE:
<223> OTHER INFORMATION: Human IL-2R alpha subunit + Avi-tag + His-tag

<400> SEQUENCE: 25

Met Gly Trp Ser Cys Ile Ile Leu Phe Leu Val Ala Thr Ala Thr Gly
1               5                   10                  15

Val His Ser Glu Leu Cys Asp Asp Pro Pro Glu Ile Pro His Ala
            20                  25                  30

Thr Phe Lys Ala Met Ala Tyr Lys Glu Gly Thr Met Leu Asn Cys Glu
        35                  40                  45

Cys Lys Arg Gly Phe Arg Arg Ile Lys Ser Gly Ser Leu Tyr Met Leu
    50                  55                  60

Cys Thr Gly Asn Ser Ser His Ser Ser Trp Asp Asn Gln Cys Gln Cys
65                  70                  75                  80

Thr Ser Ser Ala Thr Arg Asn Thr Thr Lys Gln Val Thr Pro Gln Pro
                85                  90                  95

Glu Glu Gln Lys Glu Arg Lys Thr Thr Glu Met Gln Ser Pro Met Gln
            100                 105                 110

Pro Val Asp Gln Ala Ser Leu Pro Gly His Cys Arg Glu Pro Pro Pro 115                 120                 125
Trp Glu Asn Glu Ala Thr Glu Arg Ile Tyr His Phe Val Val Gly Gln
        130                 135                 140

Met Val Tyr Tyr Gln Cys Val Gln Gly Tyr Arg Ala Leu His Arg Gly
145                 150                 155                 160

Pro Ala Glu Ser Val Cys Lys Met Thr His Gly Lys Thr Arg Trp Thr
                165                 170                 175

Gln Pro Gln Leu Ile Cys Thr Gly Val Asp Glu Gln Leu Tyr Phe Gln
            180                 185                 190

Gly Gly Ser Gly Leu Asn Asp Ile Phe Glu Ala Gln Lys Ile Glu Trp
        195                 200                 205

His Glu Ala Arg Ala His His His His His His
210                 215

<210> SEQ ID NO 26
<211> LENGTH: 660
<212> TYPE: DNA
<213> ORGANISM: Artificial Sequence
<220> FEATURE:
<223> OTHER INFORMATION: Human IL-2R alpha subunit + Avi-tag + His-tag

<400> SEQUENCE: 26
atgggatgga gctgtatcat cctcttcttg gtagcaacag ctaccggtgt gcattccgag      60
ctctgtgacg atgacccgcc agagatccca cacgccacat tcaaagccat ggcctacaag     120
gaaggaacca tgttgaactg tgaatgcaag agaggtttcc gcagaataaa aagcgggtca     180
ctctatatgc tctgtacagg aaactctagc cactcgtcct gggacaacca atgtcaatgc     240
acaagctctg ccactcggaa cacaacgaaa caagtgacac ctcaacctga gaacagaaa      300 gaaaggaaaa ccacagaaat gcaaagtcca atgcagccag tggaccaagc gagccttcca     360
ggtcactgca gggaacctcc accatgggaa aatgaagcca cagagagaat ttatcatttc     420
gtggtggggc agatggttta ttatcagtgc gtccagggat acagggctct acacagaggt     480
cctgctgaga gcgtctgcaa aatgacccac gggaagacaa ggtggaccca gccccagctc     540
atatgcacag tgtcgacga acagttatat tttcagggcg gctcaggcct gaacgacatc     600
ttcgaggccc agaagatcga gtggcacgag gctcgagctc accaccatca ccatcactga     660

<210> SEQ ID NO 27
<211> LENGTH: 473
<212> TYPE: PRT
<213> ORGANISM: Artificial Sequence
<220> FEATURE:
<223> OTHER INFORMATION: Murine IL-2R-beta-Fc(hole) fusion protein

<400> SEQUENCE: 27

Met Asp Met Arg Val Pro Ala Gln Leu Leu Gly Leu Leu Leu Leu Trp
1               5                   10                  15

Phe Pro Leu Leu Leu Leu Trp Phe Pro Gly Ala Arg Cys Ala Val Lys
            20                  25                  30

Asn Cys Ser His Leu Glu Cys Phe Tyr Asn Ser Arg Ala Asn Val Ser
        35                  40                  45

Cys Met Trp Ser His Glu Glu Ala Leu Asn Val Thr Thr Cys His Val
    50                  55                  60

His Ala Lys Ser Asn Leu Arg His Trp Asn Lys Thr Cys Glu Leu Thr
65                  70                  75                  80

Leu Val Arg Gln Ala Ser Trp Ala Cys Asn Leu Ile Leu Gly Ser Phe
                85                  90                  95

Pro Glu Ser Gln Ser Leu Thr Ser Val Asp Leu Leu Asp Ile Asn Val
            100                 105                 110

Val Cys Trp Glu Glu Lys Gly Trp Arg Arg Val Lys Thr Cys Asp Phe
            115                 120                 125

His Pro Phe Asp Asn Leu Arg Leu Val Ala Pro His Ser Leu Gln Val
            130                 135                 140

Leu His Ile Asp Thr Gln Arg Cys Asn Ile Ser Trp Lys Val Ser Gln
145                 150                 155                 160

Val Ser His Tyr Ile Glu Pro Tyr Leu Glu Phe Glu Ala Arg Arg Arg
                165                 170                 175

Leu Leu Gly His Ser Trp Glu Asp Ala Ser Val Leu Ser Leu Lys Gln
            180                 185                 190

Arg Gln Gln Trp Leu Phe Leu Glu Met Leu Ile Pro Ser Thr Ser Tyr
        195                 200                 205

Glu Val Gln Val Arg Val Lys Ala Gln Arg Asn Asn Thr Gly Thr Trp
        210                 215                 220

Ser Pro Trp Ser Gln Pro Leu Thr Phe Arg Thr Arg Pro Ala Asp Pro
225                 230                 235                 240

Met Lys Glu Gly Ala Gln Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Cys Thr Leu Pro Pro Ser Arg Asp Glu Leu
        370                 375                 380

Thr Lys Asn Gln Val Ser Leu Ser Cys Ala Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Val Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 28
<211> LENGTH: 1422
<212> TYPE: DNA
<213> ORGANISM: Artificial Sequence
<220> FEATURE:

<223> OTHER INFORMATION: Murine IL-2R-beta-Fc(hole) fusion protein

<400> SEQUENCE: 28

```
atggacatga gggtccccgc tcagctcctg ggcctcctgc tgctctggtt cccctcctg      60
ctgctctggt tcccaggtgc caggtgtgca gtgaaaaact gttcccatct tgaatgcttc    120
tacaactcaa gagccaatgt ctcttgcatg tggagccatg aagaggctct gaatgtcaca    180
acctgccacg tccatgccaa gtcgaacctg cgacactgga caaaacctg tgagctaact     240
cttgtgaggc aggcatcctg ggcctgcaac ctgatcctcg ggtcgttccc agagtcccag    300
tcactgacct ccgtggacct ccttgacata aatgtggtgt gctgggaaga aagggttgg     360
cgtagggtaa agacctgcga cttccatccc tttgacaacc ttcgcctggt ggcccctcat    420
tccctccaag ttctgcacat tgatacccag agatgtaaca taagctggaa ggtctcccag    480
gtctctcact acattgaacc atacttggaa tttgaggccc gtagacgtct tctgggccac    540
agctgggagg atgcatccgt attaagcctc aagcagagac agcagtggct cttcttggag    600
atgctgatcc ctagtacctc atatgaggtc caggtgaggg tcaaagctca acgaaacaat    660
accgggacct ggagtccctg gagccagccc ctgaccttc ggacaaggcc agcagatccc     720
atgaaggagg gagctcagga caaaactcac acatgcccac gtgcccagc acctgaactc     780
ctgggggac cgtcagtctt cctcttccc ccaaaaccca aggacacccct catgatctcc     840
cggaccctg aggtcacatg cgtggtggtg gacgtgagcc acgaagaccc tgaggtcaag    900
ttcaactggt acgtggacgg cgtggaggtg cataatgcca agacaaagcc gcgggaggag   960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagcccgca gaaccacagg tgtgcacccct gcccccatcc   1140
cgggatgagc tgaccaagaa ccaggtcagc ctctcgtgcg cagtcaaagg cttctatccc   1200
agcgacatcg ccgtggagtg ggagagcaat gggcagccgg agaacaacta caagaccacg   1260
cctcccgtgc tggactccga cggctccttc ttcctcgtga gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                       1422
```

<210> SEQ ID NO 29
<211> LENGTH: 500
<212> TYPE: PRT
<213> ORGANISM: Artificial Sequence
<220> FEATURE:
<223> OTHER INFORMATION: Murine IL-2R-gamma-Fc(knob) fusion protein

<400> SEQUENCE: 29

```
Met Asp Met Arg Val Pro Ala Gln Leu Leu Gly Leu Leu Leu Leu Trp
1               5                   10                  15

Phe Pro Leu Leu Leu Leu Trp Phe Pro Gly Ala Arg Cys Trp Ser Ser
            20                  25                  30

Lys Val Leu Met Ser Ser Ala Asn Glu Asp Ile Lys Ala Asp Leu Ile
        35                  40                  45

Leu Thr Ser Thr Ala Pro Glu His Leu Ser Ala Pro Thr Leu Pro Leu
    50                  55                  60

Pro Glu Val Gln Cys Phe Val Phe Asn Ile Glu Tyr Met Asn Cys Thr
65                  70                  75                  80

Trp Asn Ser Ser Ser Glu Pro Gln Ala Thr Asn Leu Thr Leu His Tyr
                85                  90                  95
```

```
Arg Tyr Lys Val Ser Asp Asn Asn Thr Phe Gln Glu Cys Ser His Tyr
            100                 105                 110

Leu Phe Ser Lys Glu Ile Thr Ser Gly Cys Gln Ile Gln Lys Glu Asp
            115                 120                 125

Ile Gln Leu Tyr Gln Thr Phe Val Val Gln Leu Gln Asp Pro Gln Lys
        130                 135                 140

Pro Gln Arg Arg Ala Val Gln Lys Leu Asn Leu Gln Asn Leu Val Ile
145                 150                 155                 160

Pro Arg Ala Pro Glu Asn Leu Thr Leu Ser Asn Leu Ser Glu Ser Gln
                165                 170                 175

Leu Glu Leu Arg Trp Lys Ser Arg His Ile Lys Glu Arg Cys Leu Gln
            180                 185                 190

Tyr Leu Val Gln Tyr Arg Ser Asn Arg Asp Arg Ser Trp Thr Glu Leu
        195                 200                 205

Ile Val Asn His Glu Pro Arg Phe Ser Leu Pro Ser Val Asp Glu Leu
        210                 215                 220

Lys Arg Tyr Thr Phe Arg Val Arg Ser Arg Tyr Asn Pro Ile Cys Gly
225                 230                 235                 240

Ser Ser Gln Gln Trp Ser Lys Trp Ser Gln Pro Val His Trp Gly Ser
                245                 250                 255

His Thr Val Glu Glu Asn Pro Ser Leu Phe Ala Leu Glu Ala Gly Ala
            260                 265                 270

Gln Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
        370                 375                 380

Ile Glu Lys Thr Ile Ser Lys Ala Lys Gly Gln Pro Arg Glu Pro Gln
385                 390                 395                 400

Val Tyr Thr Leu Pro Pro Cys Arg Asp Glu Leu Thr Lys Asn Gln Val
                405                 410                 415

Ser Leu Trp Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
        450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500
```

<210> SEQ ID NO 30
<211> LENGTH: 1503
<212> TYPE: DNA
<213> ORGANISM: Artificial Sequence
<220> FEATURE:
<223> OTHER INFORMATION: Murine IL-2R-gamma-Fc(knob) fusion protein

<400> SEQUENCE: 30

| | | | | | |
|---|---|---|---|---|---|
| atggacatga | gggtccccgc | tcagctcctg | ggcctcctgc | tgctctggtt | ccccctcctg | 60 |
| ctgctctggt | tcccaggtgc | caggtgttgg | agttccaagg | tcctcatgtc | cagtgcgaat | 120 |
| gaagacatca | aagctgattt | gatcctgact | tctacagccc | ctgaacacct | cagtgctcct | 180 |
| actctgcccc | ttccagaggt | tcagtgcttt | gtgttcaaca | tagagtacat | gaattgcact | 240 |
| tggaatagca | gttctgagcc | tcaggcaacc | aacctcacgc | tgcactatag | gtacaaggta | 300 |
| tctgataata | atacattcca | ggagtgcagt | cactatttgt | tctccaaaga | gattacttct | 360 |
| ggctgtcaga | tacaaaaaga | agatatccag | ctctaccaga | catttgttgt | ccagctccag | 420 |
| gacccccaga | accccagag | cgagctgta | cagaagctaa | acctacagaa | tcttgtgatc | 480 |
| ccacgggctc | cagaaaatct | aacactcagc | aatctgagtg | aatcccagct | agagctgaga | 540 |
| tggaaaagca | gacatattaa | agaacgctgt | ttacaatact | tggtgcagta | ccggagcaac | 600 |
| agagatcgaa | gctggacgga | actaatagtg | aatcatgaac | ctagattctc | cctgcctagt | 660 |
| gtggatgagc | tgaaacggta | cacatttcgg | gttcggagcc | gctataaccc | aatctgtgga | 720 |
| agttctcaac | agtggagtaa | atggagccag | cctgtccact | gggggagtca | tactgtagag | 780 |
| gagaatcctt | ccttgtttgc | actggaagct | ggagctcagg | acaaaactca | cacatgccca | 840 |
| ccgtgcccag | cacctgaact | cctgggggga | ccgtcagtct | tcctcttccc | cccaaaaccc | 900 |
| aaggacaccc | tcatgatctc | ccggacccct | gaggtcacat | gcgtggtggt | ggacgtgagc | 960 |
| cacgaagacc | ctgaggtcaa | gttcaactgg | tacgtggacg | gcgtggaggt | gcataatgcc | 1020 |
| aagacaaagc | cgcgggagga | gcagtacaac | agcacgtacc | gtgtggtcag | cgtcctcacc | 1080 |
| gtcctgcacc | aggactggct | gaatggcaag | gagtacaagt | gcaaggtctc | caacaaagcc | 1140 |
| ctcccagccc | ccatcgagaa | aaccatctcc | aaagccaaag | gcagccccg | agaaccacag | 1200 |
| gtgtacaccc | tgcccccatg | ccgggatgag | ctgaccaaga | accaggtcag | cctgtggtgc | 1260 |
| ctggtcaaag | gcttctatcc | cagcgacatc | gccgtggagt | gggagagcaa | tgggcagccg | 1320 |
| gagaacaact | acaagaccac | gcctcccgtg | ctggactccg | acggctcctt | cttcctctac | 1380 |
| agcaagctca | ccgtggacaa | gagcaggtgg | cagcagggga | acgtcttctc | atgctccgtg | 1440 |
| atgcatgagg | ctctgcacaa | ccactacacg | cagaagagcc | tctccctgtc | tccgggtaaa | 1500 |
| tga | | | | | | 1503 |

<210> SEQ ID NO 31
<211> LENGTH: 213
<212> TYPE: PRT
<213> ORGANISM: Artificial Sequence
<220> FEATURE:
<223> OTHER INFORMATION: Murine IL-2R alpha subunit + Avi-tag + His-tag

<400> SEQUENCE: 31

Met Gly Trp Ser Cys Ile Ile Leu Phe Leu Val Ala Thr Ala Thr Gly
1               5                   10                  15

Val His Ser Glu Leu Cys Leu Tyr Asp Pro Pro Glu Val Pro Asn Ala
            20                  25                  30

Thr Phe Lys Ala Leu Ser Tyr Lys Asn Gly Thr Ile Leu Asn Cys Glu

```
                35                  40                  45
Cys Lys Arg Gly Phe Arg Arg Leu Lys Glu Leu Val Tyr Met Arg Cys
 50                  55                  60
Leu Gly Asn Ser Trp Ser Ser Asn Cys Gln Cys Thr Ser Asn Ser His
 65                  70                  75                  80
Asp Lys Ser Arg Lys Gln Val Thr Ala Gln Leu Glu His Gln Lys Glu
                 85                  90                  95
Gln Gln Thr Thr Thr Asp Met Gln Lys Pro Thr Gln Ser Met His Gln
            100                 105                 110
Glu Asn Leu Thr Gly His Cys Arg Glu Pro Pro Trp Lys His Glu
        115                 120                 125
Asp Ser Lys Arg Ile Tyr His Phe Val Glu Gly Gln Ser Val His Tyr
130                 135                 140
Glu Cys Ile Pro Gly Tyr Lys Ala Leu Gln Arg Gly Pro Ala Ile Ser
145                 150                 155                 160
Ile Cys Lys Met Lys Cys Gly Lys Thr Gly Trp Thr Gln Pro Gln Leu
                165                 170                 175
Thr Cys Val Asp Glu Gln Leu Tyr Phe Gln Gly Gly Ser Gly Leu Asn
            180                 185                 190
Asp Ile Phe Glu Ala Gln Lys Ile Glu Trp His Glu Ala Arg Ala His
        195                 200                 205
His His His His His
    210

<210> SEQ ID NO 32
<211> LENGTH: 642
<212> TYPE: DNA
<213> ORGANISM: Artificial Sequence
<220> FEATURE:
<223> OTHER INFORMATION: Murine IL-2R alpha subunit + Avi-tag + His-tag

<400> SEQUENCE: 32
atgggatgga gctgtatcat cctcttcttg gtagcaacag ctaccggtgt gcattccgaa      60
ctgtgtctgt atgacccacc cgaggtcccc aatgccacat tcaaagccct ctcctacaag     120
aacggcacca tcctaaactg tgaatgcaag agaggtttcc gaagactaaa ggaattggtc     180
tatatgcgtt gcttaggaaa ctcctggagc agcaactgcc agtgcaccag caactcccat     240
gacaaatcga gaaagcaagt tacagctcaa cttgaacacc agaaagagca acaaaccaca     300
acagacatgc agaagccaac acagtctatg caccaagaga accttacagg tcactgcagg     360
gagccacctc cttggaaaca tgaagattcc aagagaatct atcatttcgt ggaaggacag     420
agtgttcact acgagtgtat tccgggatac aaggctctac agagaggtcc tgctattagc     480
atctgcaaga tgaagtgtgg aaaacggggt ggactcagc ccagctcac atgtgtcgac     540 gaacagttat attttcaggg cggctcaggc ctgaacgaca tcttcgaggc cagaagatc     600 gagtggcacg aggctcgagc tcaccaccat caccatcact ga                       642

<210> SEQ ID NO 33
<211> LENGTH: 480
<212> TYPE: PRT
<213> ORGANISM: Artificial Sequence
<220> FEATURE:
<223> OTHER INFORMATION: Cynomolgous IL-2R-beta-Fc(knob) fusion
      protein + Avi-tag

<400> SEQUENCE: 33

Met Gly Trp Ser Cys Ile Ile Leu Phe Leu Val Ala Thr Ala Thr Gly
```

-continued

```
1               5                   10                  15
Val His Ser Ala Val Asn Gly Thr Ser Arg Phe Thr Cys Phe Tyr Asn
                20                  25                  30
Ser Arg Ala Asn Ile Ser Cys Val Trp Ser Gln Asp Gly Ala Leu Gln
                35                  40                  45
Asp Thr Ser Cys Gln Val His Ala Trp Pro Asp Arg Arg Trp Asn
50                  55                  60
Gln Thr Cys Glu Leu Leu Pro Val Ser Gln Ala Ser Trp Ala Cys Asn
65                  70                  75                  80
Leu Ile Leu Gly Thr Pro Asp Ser Gln Lys Leu Thr Ala Val Asp Ile
                85                  90                  95
Val Thr Leu Arg Val Met Cys Arg Glu Gly Val Arg Trp Arg Met Met
                100                 105                 110
Ala Ile Gln Asp Phe Lys Pro Phe Glu Asn Leu Arg Leu Met Ala Pro
                115                 120                 125
Ile Ser Leu Gln Val Val His Val Glu Thr His Arg Cys Asn Ile Ser
                130                 135                 140
Trp Lys Ile Ser Gln Ala Ser His Tyr Phe Glu Arg His Leu Glu Phe
145                 150                 155                 160
Glu Ala Arg Thr Leu Ser Pro Gly His Thr Trp Glu Glu Ala Pro Leu
                165                 170                 175
Met Thr Leu Lys Gln Lys Gln Glu Trp Ile Cys Leu Glu Thr Leu Thr
                180                 185                 190
Pro Asp Thr Gln Tyr Glu Phe Gln Val Arg Val Lys Pro Leu Gln Gly
                195                 200                 205
Glu Phe Thr Thr Trp Ser Pro Trp Ser Gln Pro Leu Ala Phe Arg Thr
210                 215                 220
Lys Pro Ala Ala Leu Gly Lys Asp Thr Gly Ala Gln Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
                260                 265                 270
Pro Glu Val Thr Cys Val Val Val Asp Val Ser His Glu Asp Pro Glu
                275                 280                 285
Val Lys Phe Asn Trp Tyr Val Asp Gly Val Glu Val His Asn Ala Lys
                290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
                340                 345                 350
Ser Lys Ala Lys Gly Gln Pro Arg Glu Pro Gln Val Tyr Thr Leu Pro
                355                 360                 365
Pro Cys Arg Asp Glu Leu Thr Lys Asn Gln Val Ser Leu Trp Cys Leu
                370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
                420                 425                 430
```

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Ser
    450                 455                 460

Gly Gly Leu Asn Asp Ile Phe Glu Ala Gln Lys Ile Glu Trp His Glu
465                 470                 475                 480

<210> SEQ ID NO 34
<211> LENGTH: 1443
<212> TYPE: DNA
<213> ORGANISM: Artificial Sequence
<220> FEATURE:
<223> OTHER INFORMATION: Cynomolgous IL-2R-beta-Fc(knob) fusion
      protein + Avi-tag

<400> SEQUENCE: 34

```
atgggatgga gctgtatcat cctcttcttg gtagcaacag ctaccggtgt gcattccgcg      60
gtcaacggca cttcccggtt cacatgcttc tacaactcga gagccaacat ctcctgtgtc    120
tggagccaag atggggctct gcaggacact tcctgccaag tccacgcctg gccggacaga    180
cggcggtgga accaaacctg tgagctgctc cctgtgagtc aagcatcctg ggcctgcaac    240
ctgatcctcg aaccccaga ttctcagaaa ctgaccgcag tggatatcgt caccctgagg    300
gtgatgtgcc gtgaagggt gcgatggagg atgatgccca tccaggactt caaacccttt    360
gagaaccttc gcctgatggc cccatctcc ctccaagtcg tccacgtgga gacccacaga    420
tgcaacataa gctggaaaat ctcccaagcc tcccactact ttgaaagaca cctggagttt    480
gaggcccgga cgctgtcccc aggccacacc tgggaggagg cccccctgat gaccctcaag    540
cagaagcagg aatggatctg cctggagacg ctcaccccag acacccagta tgagtttcag    600
gtgcgggtca gcctctgca aggcgagttc acgacctgga gcccctggag ccagcccctg    660
gccttcagga caaagcctgc agcccttggg aaggacaccg gagctcagga caaaactcac    720
acatgcccac cgtgcccagc acctgaactc ctggggggac cgtcagtctt cctcttcccc    780
ccaaaaccca aggacaccct catgatctcc cggacccctg aggtcacatg cgtggtggtg    840
gacgtgagcc acgaagaccc tgaggtcaag ttcaactggt acgtggacgg cgtggaggtg    900
cataatgcca agacaaagcc gcgggaggag cagtacaaca gcacgtaccg tgtggtcagc    960
gtcctcaccg tcctgcacca ggactggctg aatggcaaga gtacaagtg caaggtctcc   1020
aacaaagccc tcccagcccc catcgagaaa accatctcca aagccaaagg gcagccccga   1080
gaaccacagg tgtacaccct gccccatgc cgggatgagc tgaccaagaa ccaggtcagc   1140
ctgtggtgcc tggtcaaagg cttctatccc agcgacatcg ccgtggagtg ggagagcaat   1200
gggcagccgg agaacaacta caagaccacg cctcccgtgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaat ccggaggcct gaacgacatc ttcgaggccc agaagattga atggcacgag   1440
tga                                                                1443
```

<210> SEQ ID NO 35
<211> LENGTH: 489
<212> TYPE: PRT
<213> ORGANISM: Artificial Sequence
<220> FEATURE:
<223> OTHER INFORMATION: Cynomolgous IL-2R-gamma-Fc(hole) fusion protein

<400> SEQUENCE: 35

```
Met Gly Trp Ser Cys Ile Ile Leu Phe Leu Val Ala Thr Ala Thr Gly
1               5                   10                  15

Val His Ser Leu Asn Thr Thr Ile Leu Thr Pro Asn Gly Asn Glu Asp
            20                  25                  30

Ala Thr Thr Asp Phe Phe Leu Thr Ser Met Pro Thr Asp Ser Leu Ser
        35                  40                  45

Val Ser Thr Leu Pro Leu Pro Glu Val Gln Cys Phe Val Phe Asn Val
    50                  55                  60

Glu Tyr Met Asn Cys Thr Trp Asn Ser Ser Glu Pro Gln Pro Thr
65                  70                  75                  80

Asn Leu Thr Leu His Tyr Trp Tyr Lys Asn Ser Asp Asn Asp Lys Val
                85                  90                  95

Gln Lys Cys Ser His Tyr Leu Phe Ser Glu Glu Ile Thr Ser Gly Cys
            100                 105                 110

Gln Leu Gln Lys Lys Glu Ile His Leu Tyr Gln Thr Phe Val Val Gln
        115                 120                 125

Leu Gln Asp Pro Arg Glu Pro Arg Arg Gln Ala Thr Gln Met Leu Lys
    130                 135                 140

Leu Gln Asn Leu Val Ile Pro Trp Ala Pro Glu Asn Leu Thr Leu Arg
145                 150                 155                 160

Lys Leu Ser Glu Ser Gln Leu Glu Leu Asn Trp Asn Asn Arg Phe Leu
                165                 170                 175

Asn His Cys Leu Glu His Leu Val Gln Tyr Arg Thr Asp Trp Asp His
            180                 185                 190

Ser Trp Thr Glu Gln Ser Val Asp Tyr Arg His Lys Phe Ser Leu Pro
        195                 200                 205

Ser Val Asp Gly Gln Lys Arg Tyr Thr Phe Arg Val Arg Ser Arg Phe
    210                 215                 220

Asn Pro Leu Cys Gly Ser Ala Gln His Trp Ser Glu Trp Ser His Pro
225                 230                 235                 240

Ile His Trp Gly Ser Asn Ser Ser Lys Glu Asn Pro Phe Leu Phe Ala
                245                 250                 255

Leu Glu Ala Gly Ala Gln Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Gly Ala Pro Ile Glu Lys Thr Ile Ser Lys Ala Lys Gly Gln
    370                 375                 380

Pro Arg Glu Pro Gln Val Cys Thr Leu Pro Pro Ser Arg Asp Glu Leu
385                 390                 395                 400

Thr Lys Asn Gln Val Ser Leu Ser Cys Ala Val Lys Gly Phe Tyr Pro
                405                 410                 415
```

```
Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Val Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 36
<211> LENGTH: 1470
<212> TYPE: DNA
<213> ORGANISM: Artificial Sequence
<220> FEATURE:
<223> OTHER INFORMATION: Cynomolgous IL-2R-gamma-Fc(hole) fusion protein

<400> SEQUENCE: 36
atgggatgga gctgtatcat cctcttcttg gtagcaacag ctaccggtgt gcattccctg      60
aacacgacaa ttctgacgcc aatgggaat gaagacgcca caactgattt cttcctgacc     120
tctatgccca ctgactccct cagtgtttcc actctgcccc tcccagaggt tcagtgtttt     180
gtgttcaatg tcgagtacat gaattgcact tggaacagca gctctgagcc ccagcctacc     240
aacctcactc tgcattattg gtacaagaat tcggataatg ataaagtcca gaagtgcagc     300
cactatctat tctctgaaga aatcacttct ggctgtcagt gcaaaaaaa ggagatccac     360 ctctaccaaa cgtttgttgt tcagctccag gacccacggg aacccaggag acaggccaca     420
cagatgctaa aactgcagaa tctggtgatc cctgggctc cggagaacct aacacttcgc     480
aaactgagtg aatcccagct agaactgaac tggaacaaca gattcttgaa ccactgtttg     540
gagcacttgg tgcagtaccg gactgactgg gaccacagct ggactgaaca atcagtggat     600
tatagacata agttctcctt gcctagtgtg gatgggcaga acgctacac gtttcgtgtc     660 cggagccgct ttaacccact ctgtggaagt gctcagcatt ggagtgaatg gagccaccca     720
atccactggg ggagcaatag ttcaaaagag aatccttttcc tgtttgcatt ggaagccgga     780
gctcaggaca aaactcacac atgcccaccg tgcccagcac ctgaactcct ggggggaccg     840
tcagtcttcc tcttccccc aaaacccaag gacaccctca tgatctcccg gacccctgag     900
gtcacatgcg tggtggtgga cgtgagccac gaagaccctg aggtcaagtt caactggtac     960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagccctc ggcgccccca tcgagaaaac catctccaaa    1140
gccaaagggc agccccgaga accacaggtg tgcaccctgc ccccatcccg ggatgagctg    1200
accaagaacc aggtcagcct ctcgtgcgca gtcaaaggct ctatcccag cgacatcgcc    1260 gtggagtggg agagcaatgg gcagccggag aacaactaca agaccacgcc tcccgtgctg    1320
gactccgacg gctccttctt cctcgtgagc aagctcaccg tggacaagag caggtggcag    1380
caggggaacg tcttctcatg ctccgtgatg catgaggctc tgcacaacca ctacacgcag    1440
aagagcctct ccctgtctcc gggtaaatga                                    1470

<210> SEQ ID NO 37
<211> LENGTH: 217
```

<212> TYPE: PRT
<213> ORGANISM: Artificial Sequence
<220> FEATURE:
<223> OTHER INFORMATION: Cynomolgous IL-2R alpha subunit + Avi-tag + His-tag

<400> SEQUENCE: 37

Met Gly Trp Ser Cys Ile Ile Leu Phe Leu Val Ala Thr Ala Thr Gly
1               5                   10                  15

Glu Leu Cys Asp Asp Asp Pro Pro Lys Ile Thr His Ala Thr Phe Lys
            20                  25                  30

Ala Met Ala Tyr Lys Glu Gly Thr Met Leu Asn Cys Glu Cys Lys Arg
        35                  40                  45

Gly Phe Arg Arg Ile Lys Ser Gly Ser Pro Tyr Met Leu Cys Thr Gly
    50                  55                  60

Asn Ser Ser His Ser Ser Trp Asp Asn Gln Cys Gln Cys Thr Ser Ser
65                  70                  75                  80

Ala Ala Arg Asn Thr Thr Lys Gln Val Thr Pro Gln Pro Glu Glu Gln
                85                  90                  95

Lys Glu Arg Lys Thr Thr Glu Met Gln Ser Gln Met Gln Leu Ala Asp
            100                 105                 110

Gln Val Ser Leu Pro Gly His Cys Arg Glu Pro Pro Trp Glu Asn
        115                 120                 125

Glu Ala Thr Glu Arg Ile Tyr His Phe Val Val Gly Gln Thr Val Tyr
    130                 135                 140

Tyr Gln Cys Val Gln Gly Tyr Arg Ala Leu His Arg Gly Pro Ala Glu
145                 150                 155                 160

Ser Val Cys Lys Met Thr His Gly Lys Thr Arg Trp Thr Gln Pro Gln
                165                 170                 175

Leu Ile Cys Thr Gly Glu Val Asp Glu Gln Leu Tyr Phe Gln Gly Gly
            180                 185                 190

Ser Gly Leu Asn Asp Ile Phe Glu Ala Gln Lys Ile Glu Trp His Glu
        195                 200                 205

Ala Arg Ala His His His His His His
    210                 215

<210> SEQ ID NO 38
<211> LENGTH: 654
<212> TYPE: DNA
<213> ORGANISM: Artificial Sequence
<220> FEATURE:
<223> OTHER INFORMATION: Cynomolgous IL-2R alpha subunit + Avi-tag + His-tag

<400> SEQUENCE: 38
atgggatgga gctgtatcat cctcttcttg gtagcaacag ctaccggtga gctctgtgac      60
gatgacccgc caaaaatcac acatgccaca ttcaaagcca tggcctacaa ggaaggaacc     120
atgttgaact gtgaatgcaa gagaggtttc gcagaataa aaagcgggtc acctatatg       180
ctctgtacag gaaactctag ccactcgtcc tgggacaacc aatgtcaatg cacaagctct     240
gctgctcgga acacaacaaa acaagtgaca cctcaacctg aagaacagaa agaaagaaaa     300
accacagaaa tgcaaagtca atgcagctg gcggaccaag tgagccttcc aggtcactgc      360
agggaacctc caccgtggga aaatgaagcc acagaaagaa tttatcattt cgtggtgggg     420
cagacggttt actaccagtg cgtccaggga tacagggctc tacacagagg tcctgctgag     480
agcgtctgca aaatgaccca cgggaagaca agatggaccc agccccagct catatgcaca     540

```
ggtgaagtcg acgaacagtt atattttcag gcggctcag gcctgaacga catcttcgag      600
gcccagaaga tcgagtggca cgaggctcga gctcaccacc atcaccatca ctga           654
```

```
<210> SEQ ID NO 39
<211> LENGTH: 19
<212> TYPE: PRT
<213> ORGANISM: Artificial Sequence
<220> FEATURE:
<223> OTHER INFORMATION: leader sequence

<400> SEQUENCE: 39

Met Asp Trp Thr Trp Arg Ile Leu Phe Leu Val Ala Ala Ala Thr Gly
 1               5                  10                  15

Ala His Ser
```

```
<210> SEQ ID NO 40
<211> LENGTH: 57
<212> TYPE: DNA
<213> ORGANISM: Artificial Sequence
<220> FEATURE:
<223> OTHER INFORMATION: leader sequence

<400> SEQUENCE: 40
atggactgga cctggagaat cctcttcttg gtggcagcag ccacaggagc ccactcc        57
```

```
<210> SEQ ID NO 41
<211> LENGTH: 57
<212> TYPE: DNA
<213> ORGANISM: Artificial Sequence
<220> FEATURE:
<223> OTHER INFORMATION: leader sequence

<400> SEQUENCE: 41
atggactgga cctggaggat cctcttcttg gtggcagcag ccacaggagc ccactcc        57
```

```
<210> SEQ ID NO 42
<211> LENGTH: 22
<212> TYPE: PRT
<213> ORGANISM: Artificial Sequence
<220> FEATURE:
<223> OTHER INFORMATION: leader sequence

<400> SEQUENCE: 42

Met Asp Met Arg Val Pro Ala Gln Leu Leu Gly Leu Leu Leu Leu Trp
 1               5                  10                  15

Phe Pro Gly Ala Arg Cys
                20
```

```
<210> SEQ ID NO 43
<211> LENGTH: 66
<212> TYPE: DNA
<213> ORGANISM: Artificial Sequence
<220> FEATURE:
<223> OTHER INFORMATION: leader sequence

<400> SEQUENCE: 43
atggacatga gggtccccgc tcagctcctg ggcctcctgc tgctctggtt cccaggtgcc     60
aggtgt                                                                66
```

```
<210> SEQ ID NO 44
<211> LENGTH: 19
<212> TYPE: PRT
<213> ORGANISM: Artificial Sequence
<220> FEATURE:
```

```
<223> OTHER INFORMATION: leader sequence

<400> SEQUENCE: 44

Met Gly Trp Ser Cys Ile Ile Leu Phe Leu Val Ala Thr Ala Thr Gly
1               5                   10                  15

Val His Ser

<210> SEQ ID NO 45
<211> LENGTH: 57
<212> TYPE: DNA
<213> ORGANISM: Artificial Sequence
<220> FEATURE:
<223> OTHER INFORMATION: leader sequence

<400> SEQUENCE: 45
atgggatgga gctgtatcat cctcttcttg gtagcaacag ctaccggtgt gcattcc        57

<210> SEQ ID NO 46
<211> LENGTH: 57
<212> TYPE: DNA
<213> ORGANISM: Artificial Sequence
<220> FEATURE:
<223> OTHER INFORMATION: leader sequence

<400> SEQUENCE: 46
atgggctggt cctgcatcat cctgtttctg gtggctaccg ccactggagt gcattcc        57

<210> SEQ ID NO 47
<211> LENGTH: 57
<212> TYPE: DNA
<213> ORGANISM: Artificial Sequence
<220> FEATURE:
<223> OTHER INFORMATION: leader sequence

<400> SEQUENCE: 47
atgggctggt cctgcatcat cctgtttctg gtcgccacag ccaccggcgt gcactct        57
```

INTERLEUKIN-2 FUSION PROTEINS AND USES THEREOF

CROSS-REFERENCE TO RELATED APPLICATIONS

This application is a divisional of and claims the right of priority under 35 USC § 121 to U.S. patent application Ser. No. 15/695,899, filed Sep. 5, 2017, now U.S. Pat. No. 10,562,949, issued Feb. 18, 2020, which is a divisional of U.S. patent application Ser. No. 14/967,019, filed on Dec. 11, 2015, now abandoned, which is a continuation of U.S. patent application Ser. No. 13/960,149, filed on Aug. 6, 2013, now abandoned, which claims the benefit of U.S. Provisional Patent Application No. 61/681,676, filed on Aug. 10, 2012, each of which are commonly owned with this application, the contents of which are hereby expressly incorporated in their entirety as though fully set forth herein.

Sequence Listing

This application contains a Sequence Listing that is submitted electronically in ASCII format and is hereby incorporated by reference in its entirety. Said ASCII copy, created on Jan. 16, 2020, is named P31142-US-4-SeqListing.txt and is 84,447 bytes in size.

FIELD OF THE INVENTION

The present invention generally relates to fusion proteins of immunoglobulins and interleukin-2 (IL-2). In addition, the present invention relates to polynucleotides encoding such fusion proteins, and vectors and host cells comprising such polynucleotides. The invention further relates to methods for producing the fusion proteins of the invention, and to methods of using them in the treatment of disease.

BACKGROUND

Regulatory T cells ($T_{reg}$s) represent specific subsets of T lymphocytes that are crucial for the maintenance of self-tolerance. These CD4$^+$CD25$^{hi}$ cells with suppressor function can be distinguished from effector T cells by the intracellular expression of the transcription factor Foxp3, as well as other cell markers such as CD127$^{lo}$, CTLA-4$^+$, LAP, CD39$^+$, PD-1$^+$, GARP, etc. Foxp3 is critical for $T_{reg}$ differentiation and function, and Foxp3 gene deficiency and mutations, both in scurfy mice and patients with immune dysregulation polyendocrinopathy, enteropathy, X-chromosome linked syndrome (IPEX) result in the breakdown of self-tolerance and the development of autoimmune diseases due to $T_{reg}$ deficiency or lack of function.

The autoimmune responses in type 1 diabetes, Systemic Lupus Erythematosus (SLE), multiple sclerosis, and many others are correlated with a deficiency in $T_{reg}$s. Data from animal models support the hypothesis that autoimmune responses are facilitated by a failure of $T_{reg}$s to control the destructive immune response to self. Type 1 diabetes is an autoimmune disease that occurs after the destruction of a majority of the insulin producing β cells in the pancreas. The frequency of type 1 diabetes is ~0.3% of the population in the US and its incidence continues to increase in the US, Europe, and in particular Scandinavia (nearly 1%) and is expected to double within the next twenty years.

The cytokine IL-2 plays a major role in the activation and function of both $T_{reg}$s as well as effector T cells ($T_{eff}$). A deficiency in IL-2 production or lack of responsiveness preferentially results in a loss of $T_{reg}$ function and an increase in the probability of autoimmunity. Because $T_{reg}$s constitutively express the high affinity IL-2 receptor at higher levels than $T_{eff}$, low doses of IL-2 preferentially support the maintenance of $T_{reg}$s as compared to $T_{eff}$ cells.

With the preferential effect of IL-2 for activating $T_{reg}$s in vitro and in vivo, the potential for low dose, long-lived IL-2 therapy would seem to have a high prospect for success in autoimmune diseases. A 200 patient, double blind, placebo controlled type 1 diabetes clinical trial with IL-2 (Proleukin®) is set to begin in late 2013. Recent clinical trials with daily low dose Proleukin ameliorated some of the signs and symptoms of chronic graft-versus-host disease (GVHD) and hepatitis C virus-induced vasculitis (Koreth et al., New Engl J Med 365, 2055-2066 (2011), Saadoun et al., New Engl J Med 365, 2067-2077 (2011)). In both studies low dose Proleukin induced $T_{reg}$s and increased the Treg:Teff ratio. However, Proleukin's poor PK properties make it suboptimal for maintaining low, consistent levels of IL-2 in man, Other methods being tested in clinical trials are personalized expansion of $T_{reg}$s ex vivo followed by reinfusion, but this approach is less than ideal and represents a challenging set of quality control issues.

Thus, a new therapeutic approach that re-establishes the natural regulatory T cell ($T_{reg}$) mediated dominant immune tolerance would greatly enhance the ability to treat patients with autoimmune diseases such as type 1 diabetes, multiple sclerosis, systemic lupus erythematosus, Crohn's disease as well as other immune-based pro-inflammatory diseases such as chronic graft versus host disease, asthma, pulmonary fibrosis, chronic obstructive pulmonary disease, and transplant rejection, both solid organ and bone marrow.

The IL-2 fusion proteins of the present invention preferentially activate $T_{reg}$s, tipping the balance toward a higher $T_{reg}$:$T_{eff}$ ratio and reduce the autoimmune response. They are long-lived, allowing convenient dosing schedules, and devoid of effector functions, reducing potential side effects and impairment of efficacy.

SUMMARY OF THE INVENTION

In one aspect, the invention provides a fusion protein comprising (i) an immunoglobulin molecule comprising a modification reducing binding affinity of the immunoglobulin molecule to an Fc receptor as compared to a corresponding immunoglobulin molecule without said modification, and (ii) two interleukin-2 (IL-2) molecules.

In one embodiment, said immunoglobulin molecule is an IgG-class immunoglobulin molecule, particularly an IgG$_1$-subclass immunoglobulin molecule. In one embodiment, said immunoglobulin molecule is a human immunoglobulin molecule. In one embodiment, said immunoglobulin molecule is capable of specific binding to an antigen. In one embodiment, said immunoglobulin molecule is a monoclonal antibody. In one embodiment, said immunoglobulin molecule is not capable of specific binding to an antigen. In one embodiment, said immunoglobulin molecule comprises a heavy chain variable region sequence based on the human Vh3-23 germline sequence. In a specific embodiment, said immunoglobulin molecule comprises the heavy chain variable region sequence of SEQ ID NO: 9. In one embodiment, said immunoglobulin molecule comprises a light chain variable region sequence based on the human Vk3-20 germline sequence. In a specific embodiment, said immunoglobulin molecule comprises the light chain variable region sequence of SEQ ID NO: 11. In an even more specific embodiment, said immunoglobulin molecule comprises the heavy chain variable region sequence of SEQ ID NO: 9 and the light chain variable region sequence of SEQ ID NO: 11.

In one embodiment, said Fc receptor is an Fcγ receptor, particularly a human Fcγ receptor. In one embodiment, said Fc receptor is an activating Fc receptor. In one embodiment, said Fc receptor is selected from the group of FcγRIIIa (CD16a), FcγRI (CD64), FcγRIIa (CD32) and FcαRI (CD89). In a specific embodiment, said Fc receptor is FcγRIIIa, particularly human FcγRIIIa. In one embodiment, said modification reduces effector function of the immunoglobulin molecule. In a specific embodiment, said effector function is antibody-dependent cell-mediated cytotoxicity (ADCC). In one embodiment, said modification is in the Fc region, particularly the CH2 region, of said immunoglobulin molecule. In one embodiment, said immunoglobulin molecule comprises an amino acid substitution at position 329 (EU numbering) of the immunoglobulin heavy chains. In a specific embodiment, said amino acid substitution is P329G. In one embodiment, said immunoglobulin molecule comprises amino acid substitutions at positions 234 and 235 (EU numbering) of the immunoglobulin heavy chains. In a specific embodiment, said amino acid substitutions are L234A and L235A (LALA). In a particular embodiment, said immunoglobulin molecule comprises the amino acid substitutions L234A, L235A and P329G (EU numbering) in the immunoglobulin heavy chains.

In one embodiment, said IL-2 molecules are wild-type IL-2 molecules. In one embodiment, said IL-2 molecules are human IL-2 molecules. In a specific embodiment, said IL-2 molecules comprise the sequence of SEQ ID NO: 1 or SEQ ID NO: 3, particularly the sequence of SEQ ID NO: 3. In one embodiment, said IL-2 molecules are each fused at their N-terminal amino acid to the C-terminal amino acid of one of the immunoglobulin heavy chains of said immunoglobulin molecule, optionally through a peptide linker.

In a specific embodiment, said fusion protein comprises the polypeptide sequences of SEQ ID NO: 17 and SEQ ID NO: 19. In one embodiment, said fusion protein essentially consists of an immunoglobulin molecule comprising a modification reducing binding affinity of the immunoglobulin molecule to an Fc receptor as compared to a corresponding immunoglobulin molecule without said modification, two interleukin-2 (IL-2) molecules, and optionally one or more peptide linker.

The invention further provides a polynucleotide encoding the fusion protein of the invention. Further provided is a vector, particularly an expression vector, comprising the polynucleotide of the invention. In another aspect, the invention provides a host cell comprising the polynucleotide or the vector of the invention. The invention also provides a method for producing a fusion protein of the invention, comprising the steps of (i) culturing the host cell of the invention under conditions suitable for expression of the fusion protein, and (i) recovering the fusion protein. Also provided is a fusion protein comprising (i) an immunoglobulin molecule comprising a modification reducing binding affinity of the immunoglobulin molecule to an Fc receptor as compared to a corresponding immunoglobulin molecule without said modification, and (ii) two interleukin-2 (IL-2) molecules, produced by said method.

In one aspect, the invention provides a pharmaceutical composition comprising the fusion protein of the invention and a pharmaceutically acceptable carrier. The fusion protein or the pharmaceutical composition of the invention is also provided for use as a Medicament, and for use in the treatment or prophylaxis of an autoimmune disease, specifically type 1 diabetes, multiple sclerosis (MS), systemic lupus erythematosus (SLE) or Crohn's disease, most specifically type 1 diabetes, or graft-versus-host disease or transplant rejection. Further provided is the use of the fusion protein of the invention for the manufacture of a medicament for the treatment of a disease in an individual in need thereof; and a method of treating a disease in an individual, comprising administering to said individual a therapeutically effective amount of a composition comprising the fusion protein of the invention in a pharmaceutically acceptable form. In one embodiment, said disease is an autoimmune disease. In a more specific embodiment, said autoimmune disease is type 1 diabetes, multiple sclerosis (MS), systemic lupus erythematosus (SLE) or Crohn's disease. In an even more specific embodiment, said autoimmune disease is type 1 diabetes. In another embodiment said disease is transplant rejection or graft-versus-host disease. In one embodiment, said individual is a mammal, particularly a human.

Further provided the fusion protein of the invention for use in selective activation of regulatory T cells in vitro or in vivo. In One embodiment, said activation comprises induction of proliferation and/or induction of IL-2 receptor signaling. In one embodiment, said use is in vitro and said fusion protein is used at a concentration of about 1 ng/mL or less, particularly about 0.1 ng/mL or less. In another embodiment, said use is in vivo and said fusion protein is used at a dose of about 20 µg/kg body weight or less, particularly about 12 µg/kg body weight or less.

The invention also provides a method for selective activation of regulatory T cells in vitro or in vivo, comprising contacting said regulatory T cells with the fusion protein of the invention. In one embodiment, said activation comprises induction of proliferation and/or induction of IL-2 receptor signaling. In one embodiment, said method is in vitro and said fusion protein is used at a concentration of about 1 ng/mL or less, particularly about 0.1 ng/mL or less. In another embodiment, said method is in vivo and said fusion protein is used at a dose of about 20 µg/kg body weight or less, particularly about 12 µg/kg body weight or less.

DETAILED DESCRIPTION OF THE INVENTION

Definitions

Figure 1:
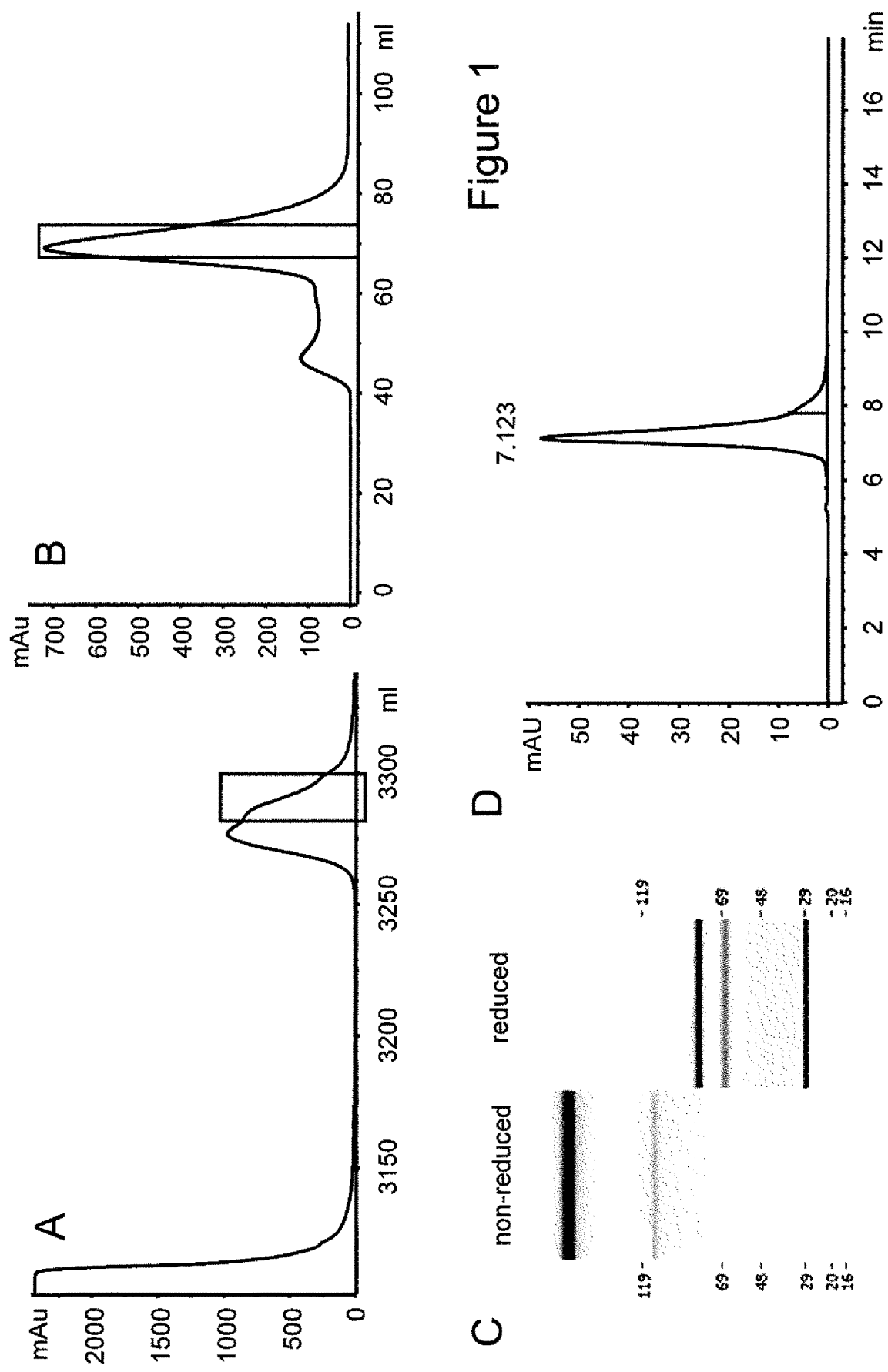
FIG. 1. Purification of DP47GS IgG-IL-2 fusion protein (see SEQ ID NOs 13, 15, 19). (A) Elution profile of the Protein A affinity chromatography step. (B) Elution profile of the size exclusion chromatography step. Yield 4 mg/L. (C) Analytical capillary electrophoresis SDS (Caliper) of the final product. The following band were observed: non-reduced—7.5% area at 111 kDa, 92.5% area at 174 kDa; reduced—23.6% area at 29 kDa, 23.5% area at 67 kDa, 52.9% area at 82 kDa. The product contains about 7.5% "half IgG". (D) Analytical size exclusion chromatography of the final product on a TSKgel G3000 SW XL column (91% monomer content).

Terms are used herein as generally used in the art, unless otherwise defined in the following.

As used herein, the term "fusion protein" refers to a fusion polypeptide molecule comprising an immunoglobulin molecule and an IL-2 molecule, wherein the components of the fusion protein are linked to each other by peptide-bonds, either directly or through peptide linkers. For clarity, the individual peptide chains of the immunoglobulin component of the fusion protein may be linked non-covalently, e.g. by disulfide bonds.

"Fused" refers to components that are linked by peptide bonds, either directly or via one or more peptide linkers.

By "specific binding" is meant that the binding is selective for the antigen and can be discriminated from unwanted or non-specific interactions. The ability of an immunoglobulin to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljebiad et al., Glyco J 17, 323-329 (2000)), and traditional binding assays (Heeley, Endocr Res 28, 217-229 (2002)). In one embodiment, the extent of binding of an immunoglobulin to an unrelated protein is less than about 10% of the binding of the immunoglobulin to the antigen as measured, e.g. by SPR. In certain embodiments, an immunoglobulin that binds to the antigen has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

As used herein, the term "antigenic determinant" is synonymous with "antigen" and refers to a site (e.g. a contiguous stretch of amino acids or a conformational configuration made up of different regions of non-contiguous amino acids) on a polypeptide macromolecule to which an antibody binds, forming an antibody-antigen complex. Useful antigenic determinants can be found, for example, on the surfaces of cells, free in blood serum, and/or in the extracellular matrix (ECM).

As used herein, the term "single-chain" refers to a molecule comprising amino acid monomers linearly linked by peptide bonds.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε (IgE), γ (IgG), or µ (IgM), some of which may be further divided into subclasses, e.g. $γ_1$ ($IgG_1$), $γ_2$ ($IgG_2$), $γ_3$ ($IgG_3$), $γ_4$ ($IgG_4$), $α_1$ ($IgA_1$) and $α_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

As used herein, "Fab fragment" refers to an immunoglobulin fragment comprising a VL domain and a constant domain of a light chain (CL), and a VH domain and a first constant domain (CH1) of a heavy chain.

The "class" of an antibody or immunoglobulin refers to the type of constant domain or constant region possessed by its heavy chain. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively.

The term "variable region" or "variable domain" refers to the domain of an immunoglobulin or antibody heavy or light chain that is generally involved in binding the immunoglobulin or antibody to antigen. However, the immunoglobulin comprised in the fusion protein of the present invention may comprise variable regions which do not confer antigen-binding specificity. The variable domains of the heavy chain and light chain (VH and VL, respectively) of an immunoglobulin or antibody generally have similar structures, with each domain comprising four conserved framework regions (FRs) and three hype/variable regions (HVRs). See, e.g. Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an immunoglobulin or antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol. 196, 901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, Front. Biosci. 13, 1619-1633 (2008)). Unless otherwise indicated, HVR residues and other residues in the variable domain (e.g. FR residues) are numbered herein according to Kabat et al., supra (referred to as "Kabat numbering").

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human immunoglobulin" is one which possesses an amino acid sequence which corresponds to that of an immunoglobulin produced by a human or a human cell or derived from a non-human source that utilizes human immunoglobulin repertoires or other human immunoglobulin-encoding sequences. This definition of a human immunoglobulin specifically excludes a humanized immunoglobulin comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, Which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an immunoglobulin heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a valiant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical immunoglobulin heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of immunological Interest, 5th Ed. Public Health Service, National Institutes of Health, Bethesda, Md., 1991.

The term "effector functions" refers to those biological activities attributable to the Fc region of an immunoglobulin, which vary with the immunoglobulin isotype. Examples of immunoglobulin effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of ea surface receptors (e.g. B cell receptor), and B cell activation.

An "activating Fc receptor" is an Fc receptor that following engagement by an Fc region of an immunoglobulin elicits signaling events that stimulate the receptor-bearing cell to perform effector functions, Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637 (version 141)).

The term "interleukin-2" or "IL-2" as used herein, refers to any native IL-2 from any vertebrate source, including mammals such as primates (e.g. humans) and rodents (e.g. mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule.

By a "native IL-2", also termed "wild-type IL-2", is meant a naturally occurring IL-2. The sequence of a native human IL-2 molecule is shown in SEQ ID NO: 1. For the purpose of the present invention, the term wild-type also encompasses forms of IL-2 comprising one or more amino acid mutation that does not affect IL-2 receptor binding compared to the naturally occurring, native IL-2, such as e.g. a substitution of cysteine at a position corresponding to residue 125 of human IL-2 to alanine. In some embodiments wild-type IL-2 for the purpose of the present invention comprises the amino acid substitution C125A (see SEQ ID NO: 3).

The term "CD25" or "IL-2 receptor α" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of an exemplary human CD25 (with signal sequence, Avi-tag and His-tag) is shown in SEQ ID NO: 25.

The term "high-affinity IL-2 receptor" as used herein refers to the heterotrimeric form of the IL-2 receptor, consisting of the receptor γ-subunit (also known as common cytokine receptor γ-subunit, $\gamma_c$, or CD132), the receptor β-subunit (also known as CD122 or p70) and the receptor α-subunit (also known as CD25 or p55). The term "intermediate-affinity IL-2 receptor" or "IL-2 receptor βγ" by contrast refers to the IL-2 receptor including only the γ-subunit and the β-subunit, without the α-subunit (for a review see e.g. Olejniczak and Kasprzak, Med Sci Monit 14, RA179-189 (2008)). The amino acid sequences of exemplary human CD122 and CD132 (fused to an Fc region with a His-tag) are shown in SEQ ID NOs 21 and 23, respectively.

By "regulatory T cell" or "$T_{reg}$ cell" is meant a specialized type of CD4+ T cell that can suppress the responses of other T cells. $T_{reg}$ cells are characterized by expression of CD4, the α-subunit of the IL-2 receptor (CD25), and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors.

By "selective activation of $T_{reg}$ cells" is meant activation of $T_{reg}$ cells essentially without concomitant activation of other T cell subsets (such as CD4+ T helper cells, CD8+ cytotoxic T cells, NK T cells) or natural killer (NK) cells. Methods for identifying and distinguishing these cell types are described in the Examples. Activation may include induction of IL-2 receptor signaling (as measured e.g. by detection of phosphorylated STAT5a), induction of proliferation (as measured e.g. by detection of Ki-67) and/or up-regulation of expression of activation (such as e.g. CD25).

The term "peptide linker" refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$ or $G_4(SG_4)_n$ peptide linkers. "n" is generally a number between 1 and 10, typically between 2 and 4.

The term "modification" refers to any manipulation of the peptide backbone (e.g. amino acid sequence) or the post-translational modifications (e.g. glycosylation) of a polypeptide.

A "knob-into-hole modification" refers to a modification within the interface between two immunoglobulin heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Introduction of two cysteine residues at position S354 and Y3-49, respectively, results in formation of a disulfide bridge between the two antibody heavy chains in the Fc region, further stabilizing the dimer (Carter, J Immunol Methods 248, 7-15 (2001)).

An amino acid "substitution" refers to the replacement in a polypeptide of one amino acid with another amino acid. In one embodiment, an amino acid is replaced with another amino acid having similar structural and/or chemical properties, e.g. conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g. basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid substitution. For example, a substitution from proline at position 329 of the immunoglobulin heavy chain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from. Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the fusion proteins of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

"Autoimmune disease" refers to a non-malignant disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g. type 1 diabetes mellitus or insulin dependent diabetes mellitus); multiple sclerosis and juvenile onset diabetes.

Fusion Proteins of the Invention

The invention provides novel immunoglobulin-IL-2 fusion proteins with particularly advantageous properties for the use in therapeutic methods as described herein.

In a first aspect, the invention provides a fusion protein comprising (i) an immunoglobulin molecule comprising a modification reducing binding affinity of the immunoglobulin molecule to an Fc receptor as compared to a corresponding immunoglobulin molecule without said modification, and (ii) two interleukin-2 (IL-2) molecules.

In one embodiment, said fusion protein essentially consists of an immunoglobulin molecule comprising a modification reducing binding affinity of the immunoglobulin molecule to an Fc receptor as compared to a corresponding immunoglobulin molecule without said modification, two interleukin-2 (IL-2) molecules, and optionally one or more peptide linker.

As shown in the Examples, a fusion protein comprising two molecules surprisingly provides for greatly improved efficacy and selectivity in the activation of regulatory T cells, as compared to a corresponding fusion protein comprising a single IL-2 molecule.

In one embodiment, said immunoglobulin molecule is an IgG-class immunoglobulin molecule, particularly an $IgG_1$-subclass immunoglobulin molecule. In one embodiment, said immunoglobulin molecule is a human immunoglobulin molecule, i.e. it comprises fully human variable and constant regions. The sequence of an exemplary human $IgG_1$ constant region is shown in SECS ID NO: 8. An IgG-class immunoglobulin molecule comprises (i) two immunoglobulin light chains, each comprising from N- to C-terminus a light chain variable domain (VL) and a light chain constant domain (CL), and (ii) two immunoglobulin heavy chains, each comprising from N-terminus to C-terminus a heavy chain variable domain (VH), a heavy chain constant domain (CH) 1, an immunoglobulin hinge region, a CH2 domain and a CH3 domain. The latter two domains form part of the Fc region of the immunoglobulin molecule. The two heavy chains dimerize in the Fc region.

In one embodiment of the fusion protein according to the invention, said two IL-2 molecules are each fused at their N-terminal amino acid to the C-terminal amino acid of one of the immunoglobulin heavy chains of said immunoglobulin molecule, optionally through a peptide linker. Fusion of two (identical) IL-2 molecules to the immunoglobulin heavy chains allows for simple production of the fusion protein, avoiding the formation of undesired side products and obviating the need for modifications promoting heterodimerization of non-identical heavy chains, such as a knob-into-hole modification.

Fusion of the IL-2 molecules to an immunoglobulin molecule provides for favorable pharmacokinetic properties, including a long serum half-life (due to recycling through binding to FcRn, and molecular size being well above the threshold for renal filtration), as compared to free (unfused) IL-2. Furthermore, the presence of an immunoglobulin molecule also enables simple purification of fusion proteins by e.g. protein A affinity chromatography. At the same time, however, the presence of an immunoglobulin molecule, specifically the Fc region of an immunoglobulin molecule, may lead to undesirable targeting of the fusion protein to cells expressing Fc receptors rather than to the preferred IL-2 receptor bearing cells. Moreover, the engagement of Fc receptors may lead to release of (pro-inflammatory) cytokines and undesired activation of various immune cells other than regulatory T cells. Therefore, said immunoglobulin molecule comprised in the fusion protein of the invention comprises a modification reducing binding affinity of the immunoglobulin molecule to an Fc receptor, as compared to a corresponding immunoglobulin molecule without said modification. In a specific embodiment, said Fc receptor is an Fcγ receptor, particularly a human Fcγ receptor. Binding affinity to Fc receptors can be easily determined e.g. by ELISA, or by Surface Plasmon Resonance (SPR) using standard instrumentation such as a BIAcore instrument (GE Healthcare) and Fc receptors such as may be obtained by recombinant expression. A specific illustrative and exemplary embodiment for measuring binding affinity is described in the following. According to one embodiment, Binding affinity to an Fc receptor is measured by surface plasmon resonance using a BIACORE® T100 machine (GE Healthcare) at 25° C. with ligand (Fc receptor) immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 µg/ml before injection at a flow rate of 10 µl/min to achieve approximately 100-5000 response units (RU) of coupled protein. Following the injection of the ligand, 1 M ethanolamine is injected to block unreacted groups. For kinetics measurements, three-to five-fold serial dilutions of antibody (range between ~0.01 nM to 300 nM) are injected in RBS-EP+ (GE Healthcare, 10 mM HEPES, 150 mM NaCl, 3 mM EDTA, 0.05% Surfactant P20, pH 7.4) at 25° C. at a flow rate of approximately 30-50 µl/min. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999). Alternatively, binding affinity antibodies to Fc receptors may be evaluated using cell lines known to express particular Fc receptors, such as NK cells expressing FcγIIIa receptor.

In one embodiment, the modification comprises one or more amino acid mutation that reduces the binding affinity of the immunoglobulin to an Fc receptor. In one embodiment the amino acid mutation is an amino acid substitution. Typically, the same one or more amino acid mutation is present in each of the two immunoglobulin heavy chains. In one embodiment said amino acid mutation reduces the binding affinity of the immunoglobulin to the Fc receptor by at least 2-fold, at least 5-fold, or at least 10-fold. In embodiments where there is more than one amino acid mutation that reduces the binding affinity of the immunoglobulin to the Fc receptor, the combination of these amino acid mutations may reduce the binding affinity of the immunoglobulin to the Fc receptor by at least 10-fold, at least 20-fold, or even at least 50-fold. In one embodiment said immunoglobulin molecule exhibits less than 20%, particularly less than 10%, more particularly less than 5% of the binding affinity to an Fc receptor as compared to a corresponding immunoglobulin molecule without said modification.

In one embodiment, said Fc receptor is an activating Fc receptor. In a specific embodiment, said Fc receptor is selected from the group of FcγRIIIa (CD16a), FcγRI (CD64), FcγRIIa (CD32) and FcαRI (CD89). In a specific embodiment the Fc receptor is an Fcγ receptor, more specifically an FcγRIIIa, FcγRI or FcγRIIa receptor. Preferably, binding affinity to each of these receptors is reduced. In an even more specific embodiment, said Fc receptor is FcγIIIa, particularly human FcγIIIa. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the immuoglobulin molecule to said receptor, is achieved when the immunoglobulin molecule exhibits greater than about 70% of the binding affinity of an unmodified form of the immunoglobulin molecule to FcRn. Immunoglobulin molecules comprised in the fusion proteins of the invention may exhibit greater than about 80% and even greater than about 90% of such affinity.

In one embodiment, said modification reducing binding affinity of the immunoglobulin molecule to an Fc receptor is in the Fc region, particularly the CH2 region, of the immunoglobulin molecule. In one embodiment, said immunoglobulin molecule comprises an amino acid substitution at position 329 (EU numbering) of the immunoglobulin heavy chains. In a more specific embodiment said amino acid substitution is P329A or P329G, particularly P329G. In one embodiment, said immunoglobulin molecule comprises amino acid substitutions at positions 234 and 235 (EU numbering) of the immunoglobulin heavy chains. In a specific embodiment, said amino acid substitutions are L234A and L235A (LALA). In one embodiment said immunoglobulin molecule comprises an amino acid substitution at position 329 (EU numbering) of the antibody heavy chains and a further amino acid substitution at a position selected from position 228, 233, 234, 235, 297 and 331 of the immunoglobulin heavy chains. In a more specific embodiment the further amino acid substitution is S228P, E233P, L234A, L235A, L235E, N297A, N297D or P331S. In a particular embodiment, said immunoglobulin molecule comprises amino acid substitutions at positions P329, L234 and L235 (EU numbering) of the immunoglobulin heavy chains. In a more particular embodiment, said immunoglobulin molecule comprises the amino acid substitutions L234A, L235A and P329G (LALA P329G) in the immunoglobulin heavy chains. This combination of amino acid substitutions almost completely abolishes Fcγ receptor binding of a human IgG-class immunoglobulin, as described in PCT patent application no. PCT/EP2012/055393, incorporated herein by reference in its entirety. PCT patent application no. PCT/EP2012/055393 also describes methods of preparing such modified immunoglobulin and methods for determining its properties such as Fc receptor binding or effector functions.

Immunoglobulins comprising modifications in the immunoglobulin heavy chains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Immunoglobulins or antibodies which comprise modifications reducing Fc receptor binding generally have reduced effector functions, particularly reduced ADCC, as compared to corresponding unmodified immunoglobulins or antibodies. Hence, in one embodiment, said modification reducing binding affinity of the immunoglobulin molecule to an Fc receptor reduces effector function of the immunoglobulin molecule. In a specific embodiment, said effector function is antibody-dependent cell-mediated cytotoxicity (ADCC). In one embodiment, ADCC is reduced to less than 20% of the ADCC induced by a corresponding immunoglobulin molecule without said modification. Effector function of an immunoglobulin or antibody can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998). In some embodiments binding of the immunoglobulin molecule to a complement component, specifically to C1, is also reduced. Accordingly, complement-dependent cytotoxicity (CDC) may also be reduced. C1q binding assays may be carried out to determine whether the immunoglobulin is able to bind C1q and hence has CDC activity. See e.g. C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In addition to the immunoglobulin molecules described hereinabove and in PCT patent application no. PCT/EP2012/055393, immunoglobulins with reduced Fc receptor binding and/or effector function also include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

IgG$_4$-subclass immunoglobulins exhibit reduced binding affinity to Fc receptors and reduced effector functions as compared to IgG$_1$ immunoglobulins. Hence, in some embodiments, said immunoglobulin molecule comprised in the fusion protein of the invention is an IgG$_4$-subclass immunoglobulin, particularly a human IgG$_4$-subclass immunoglobulin. In one embodiment said IgG$_1$-subclass immunoglobulin comprises amino acid substitutions in the Fc region at position S228, specifically the amino acid substitution S228P. To further reduce its binding affinity to an Fc receptor and/or its effector function, in one embodiment, said IgG$_4$-subclass immunoglobulin comprises an amino acid substitution at position L235, specifically the amino acid substitution L235E. In another embodiment, said IgG$_4$-subclass immunoglobulin comprises an amino acid substitution at position P329, specifically the amino acid substitution P329G. In a particular embodiment, said IgG$_4$-subclass immunoglobulin comprises amino acid substitutions at positions S228, L235 and P329, specifically amino acid substitutions S228P, L235E and P329G. Such modified IgG$_4$ subclass immunoglobulins and their Fcγ receptor binding properties are described in PCT patent application no. PCT/EP2012/055393, incorporated herein by reference in its entirety.

In one embodiment, said immunoglobulin molecule is capable of specific binding to an antigen. In one embodiment, said immunoglobulin molecule is a monoclonal antibody. In one embodiment, said immunoglobulin molecule is not capable of specific binding to an antigen, particularly not capable of specific binding to a human antigen. The absence of specific binding of such an immunoglobulin molecule to an antigen (i.e. the absence of any binding that can be discriminated from non-specific interaction) can be determined e.g. by ELISA or surface plasmon resonance as described herein. Such an immunoglobulin molecule is particularly useful e.g. for enhancing the serum half-life of the fusion protein, where targeting to a particular tissue is not desired.

In one embodiment, said immunoglobulin molecule comprises a heavy chain variable region sequence based on the human Vh3-23 germline sequence. In a specific embodiment, said immunoglobulin molecule comprises a heavy chain variable region sequence that is at least 95%, 96%, 97%, 98%, 99% or 100% identical to the sequence of SEQ ID NO: 9. In one embodiment, said immunoglobulin molecule comprises a light chain variable region sequence based on the human Vk3-20 germline sequence. In a specific embodiment, said immunoglobulin molecule comprises a light chain variable region sequence that is at least 95%, 96%, 97%, 98%, 99% or 100% identical to the sequence of SEQ ID NO: 11. In an even more specific embodiment, said immunoglobulin molecule comprises the heavy chain variable region sequence of SEQ ID NO: 9 and the light chain variable region sequence of SEQ ID NO: 11. Immunoglobulin molecules comprising these variable region sequences are not capable of specific binding to an antigen, particularly a human antigen. They lack binding to normal tissues as well as PBMCs, have no polyreactivity and show no non-specific accumulation in vivo by imaging (data not shown). The variable region sequences are entirely based on human germline sequences, with the exception of the heavy chain CDR 3 wherein a CSG sequence has been introduced to generate a non-binding immunoglobulin.

In one embodiment, said IL-2 molecules are wild-type IL-2 molecules. In one embodiment, said IL-2 molecules are human IL-2 molecules. In a specific embodiment, said IL-2 molecules comprise the sequence of SEQ IU NO: 1 (native human IL-2).

In one embodiment, said IL-2 molecule comprises an amino acid substitution at a position corresponding to residue 125 of human IL-2. In one embodiment said amino acid substitution is C125A. In a specific embodiment, said IL-2 molecule comprises the sequence of SEQ ID NO: 3 (human IL-2 with the amino acid substitution C125A). Alternatively, the cysteine at position 125 may be replaced with another neutral amino acid such as serine, threonine or valine, yielding C125S IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 molecule may include a mutation whereby methionine normally occurring at position 104 of wild-type human IL-2 is replaced by a neutral amino acid such as alanine (see U.S. Pat. No. 5,206,344). Such modifications in human IL-2 may provide additional advantages such as increased expression or stability.

The IL-2 molecules comprised in the fusion protein of the invention may also be unglycosylated IL-2 molecules. For example, elimination of the O-glycosylation site of the IL-2 molecule results in a more homogenous product when the fusion protein is expressed in mammalian cells such as CHO or HEK cells, Thus, in certain embodiments the IL-2 molecule comprises a modification which eliminates the O-glycosylation site of IL-2 at a position corresponding to residue 3 of human IL-2. In one embodiment said modification which eliminates the O-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, and T3P. In a specific embodiment, said modification is the amino acid substitution T3A.

In one embodiment, the fusion protein is capable of binding to IL-2 βγ receptor with an affinity constant ($K_D$) of smaller than 10 nM, particularly smaller than 3 nM, when measured by SPR at 25° C. In a specific embodiment, said IL-2 βγ receptor is human IL-2 βγ receptor. In one embodiment, the fusion protein is capable of binding to IL-2 α receptor with an affinity constant ($K_D$) of smaller than 100 nM, particularly smaller than 20 nM, when measured by SPR at 25° C. In a specific embodiment, said IL-2 α receptor is human IL-2 α receptor. A method for measuring binding affinity to IL-2 βγ or IL-2 α receptor by SPR is described herein. According to one embodiment, binding affinity ($K_D$) is measured by surface plasmon resonance using a BIACORE® T100 machine (GE Healthcare) at 25° C. with IL-2 receptors immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant IL-2 receptor is diluted with 10 mM sodium acetate, pH 5.5, to 0.5-30 μg/ml before injection at a flow rate of 10 μl/minute to achieve approximately 200-1000 (for IL-2R α) or 500-3000 (for IL-2R βγ heterodimer) response units (RU) of coupled protein. Following the injection of IL-2 receptor, 1 M ethanolamine is injected to block unreacted groups. For kinetics measurements, three-fold serial dilutions of fusion protein (range between ~3 nM to 300 nM) are injected, in HBS-EP+ (GE Healthcare, 10 mM HEPES, 150 mM NaCl, 3 mM EDTA, 0.05% Surfactant P20, pH 7.4) at 25° C. at a flow rate of approximately 30 μl/min. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

In a particular aspect, the invention provides a fusion protein comprising (i) an IgG$_1$-subclass immunoglobulin molecule comprising the amino acid substitutions L234A, L235A and P329G (EU numbering) in the immunoglobulin heavy chains, and (ii) two interleukin-2 (IL-2) molecules, each fused at its N-terminal amino acid to the C-terminal amino acid of one of the immunoglobulin heavy chains through a peptide linker. In a specific embodiment, said immunoglobulin molecule comprises the heavy chain variable region sequence of SEQ ID NO: 9 and the light chain variable region sequence of SEQ ID NO: 11. In a further specific embodiment, said IL-2 molecules each comprise the amino acid sequence of SEQ ID NO: 3, In an even more specific embodiment, said fusion protein comprises a polypeptide sequence that is at least about 80%, 85%, 90%, 95%, 96%, 97%, 98%, 99% or 100% identical to the sequence of SEQ ID NO: 17, and a polypeptide sequence that is at least about 80%, 85%, 90%, 95%, 96%, 97%, 98%, 99% or 100% identical to the sequence of SEQ ID NO: 19.

As shown in the Examples, the fusion protein of the invention can be used to selectively activate regulatory T cells (i.e. essentially without concomitant activation of other T cell subsets and/or NK cells). Thus, the invention particularly provides the fusion protein for use in selective activation of regulatory T cells in vitro or in vivo. In one embodiment, said use comprises contacting regulatory T cells with said fusion protein in vitro or in vivo. In one embodiment, said use further comprises contacting other (non-regulatory) T cells with said fusion protein. In one embodiment, said use is in vitro and said fusion protein is used at a concentration of about 1 ng/mL or less, particularly about 0.1 ng/mL or less. In another embodiment, said use is in vivo and said fusion protein is used at a dose of about 20 µg/kg body weight or less, particularly about 12 µg/kg body weight or less (wherein "body weight" refers to the body weight of the individual to whom the fusion protein is administered).

The invention also provides a method for selective activation of regulatory T cells in vitro or in vivo, comprising contacting said regulatory T cells with the fusion protein of the invention. In one embodiment, said method further comprises contacting other (non-regulatory) T cells with said fusion protein. In one embodiment, said activation comprises induction of proliferation and/or induction of IL-2 receptor signaling. In one embodiment, said method is in vitro and said fusion protein is used at a concentration of about 1 ng/mL or less, particularly about 0.1 ng/mL or less. In another embodiment, said method is in vivo and said fusion protein is used at a dose of about 20 µg/kg body weight or less, particularly about 12 µg/kg body weight or less (wherein "body weight" refers to the body weight of the individual to whom the fusion protein is administered).

According to certain embodiments of the use or method described in the preceding paragraphs, said activation comprises induction of proliferation and/or induction of IL-2 receptor signaling. Induction of proliferation can be measured e.g. by detection of the intracellular proliferation marker Ki-67, as described in the Examples. In one embodiment, proliferation of regulatory T cells activated by the fusion protein of the invention is increased at least about 1.5-fold, at least about 2-fold, or at least about 3-fold, as compared to proliferation of non-activated regulatory T cells. In one embodiment, proliferation of other (non-regulatory) T cells and/or NK cells contacted with the fusion protein of the invention is increased less than about 1.5 fold, less than about 1.2 fold, or less than about 1.1 fold, as compared to proliferation of corresponding cells not contacted with said fusion protein. Induction of IL-2 receptor signaling can be measured e.g. by detection of phosphorylated STAT5, as described in the Examples. In one embodiment, IL-2 receptor signaling in regulatory T cells activated by the fusion protein of the invention is increased at least about 1.5-fold, at least about 2-fold, at least about 3-fold, or at least about 5-fold, as compared to IL-2 receptor signaling in non-activated regulatory T cells. In one embodiment, IL-2 receptor signaling in other (non-regulatory) T cells and/or NK cells contacted with the fusion protein or the invention is increased less than about 1.5 fold, or less than about 1.2 fold, or less than about 1.1 fold, as compared to IL-2 receptor signaling in corresponding cells not contacted with said fusion protein.

Polynucleotides

The invention further provides polynucleotides encoding a fusion as described herein or a fragment thereof.

Polynucleotides of the invention include those that are at least about 80%, 85%, 90%, 95%, 96%, 97%, 98%, 99%, or 100% identical to the sequences set forth in SEQ ID NOs 2, 4, 5, 6, 7, 10, 12, 18 and 20 including functional fragments or variants thereof.

The polynucleotides encoding fusion proteins of the invention may be expressed as a single polynucleotide that encodes the entire fusion protein or as multiple (e.g., two or more) polynucleotides that are co-expressed. Polypeptides encoded by polynucleotides that are co-expressed may associate through, e.g., disulfide bonds or other means to form a functional fusion protein. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In one embodiment, the present invention is directed to a polynucleotide encoding a fusion protein of an immunoglobulin molecule and two IL-2 molecules, or a fragment thereof, wherein the polynucleotide comprises a sequence that encodes a variable region sequence as shown in SEQ ID NO 9 or 11. In another embodiment, the present invention is directed to a polynucleotide encoding a fusion protein of an immunoglobulin molecule and two IL-2 molecules, or a fragment thereof, wherein the polynucleotide comprises a sequence that encodes a polypeptide sequence as shown in SEQ ID NO 17 or 19. In another embodiment, the invention is further directed to a polynucleotide encoding a fusion protein of an immunoglobulin molecule and two IL-2 molecules, or a fragment thereof, wherein the polynucleotide comprises a sequence that is at least about 80%, 85%, 90%, 95%, 96%, 97%, 98%, or 99% identical to a nucleic acid sequence shown SEQ ID NO 2, 4, 5, 6, 7, 10, 12, 18 or 20. In another embodiment, the invention is directed to a polynucleotide encoding a fusion protein of an immunoglobulin molecule and two IL-2 molecules, or a fragment thereof, wherein the polynucleotide comprises a nucleic acid sequence shown in SEQ ID NO 2, 4, 5, 6, 7, 10, 12, 18 or 20. In another embodiment, the invention is directed to a polynucleotide encoding a fusion protein of an immunoglobulin molecule and two IL-2 molecules, or a fragment thereof, wherein the polynucleotide comprises a sequence that encodes a variable region sequence that is at least about 80%, 85%, 90%, 95%, 96%, 97%, 98%, or 99% identical to the amino acid sequence of SEQ ID NO 9 or 11. In another embodiment, the invention is directed to a polynucleotide encoding a fusion protein of an immunoglobulin molecule and two IL-2 molecules, or a fragment thereof, wherein the polynucleotide comprises a sequence that encodes a polypeptide sequence that is at least 80%, 85%, 90%, 95%, 96%, 97%, 98%, or 99% identical to the amino acid sequence of SEQ ID NO 17 or 19. The invention encompasses a polynucleotide encoding an a fusion protein of an immunoglobulin molecule and two IL-2 molecules, or a fragment thereof, wherein the polynucleotide comprises a sequence that encodes the variable region sequences of SEQ ID NO 9 or 11 with conservative amino acid substitutions. The invention also encompasses a polynucleotide encoding a fusion protein of an immunoglobulin molecule and two IL-2 molecules, or a fragment thereof, wherein the polynucleotide comprises a sequence that encodes the polypeptide sequences of SEQ ID NO 17 or 19 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Fusion proteins of the invention may be obtained, for example, by solid-state peptide synthesis (e.g. Merrifield solid phase synthesis) or recombinant production. For recombinant production one or more polynucleotide encoding the fusion protein (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a fusion protein (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the fusion protein (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the fusion protein (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the fusion is desired, DNA encoding a signal sequence may be placed upstream of the nucleic acid encoding a fusion protein of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. The amino acid and nucleotide sequences of exemplary secretory signal peptides are shown in SEQ ID NOs 39-47.

DNA encoding a short protein sequence that could be used to facilitate later purification (e.g. a histidine tag) or assist in labeling the fusion protein may be included within or at the ends of the fusion protein (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a fusion protein of the invention. As used herein, the term "host cell" refers to any kind of cellular system which can be engineered to generate the fusion proteins of the invention or fragments thereof. Host cells suitable for replicating and for supporting expression of fusion proteins are well known in the art. Such cells may be transfected or transduced as appropriate with the particular expression vector and large quantities of vector containing cells can be grown for seeding large scale fermenters to obtain sufficient quantities of the fusion protein for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese Hamster ovary (CHO) cells, including dhfr⁻ CHO cells (Urlaub et al., Proc Natl Acad Sci USA 77, 4216 (1980)); and myeloma, cell lines such as YO, NS0, P3X63 and Sp2/0. For a review of certain mammalian host cell lines suitable for protein production, see, e.g., Yazaki and Wu, Methods in Molecular. Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one embodiment, a method of producing a fusion protein according to the invention is provided, wherein the method comprises culturing a host cell comprising a polynucleotide encoding the fusion protein, as provided herein, under conditions suitable for expression of the fusion protein, and recovering the fusion protein from the host cell (or host cell culture medium).

In the fusion proteins of the invention, the components (immunoglobulin molecule and IL-2 molecule) are genetically fused to each other. Fusion proteins can be designed such that its components are fused directly to each other or indirectly through a linker sequence. The composition and length of the linker may be determined in accordance with methods well known in the art and may be tested for efficacy. Additional sequences may also be included to incorporate a cleavage site to separate the individual components of the fusion protein if desired, for example an endopeptidase recognition sequence.

In certain embodiments the fusion proteins of the invention comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) gaffing the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci. USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al, in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the immunoglobulins comprised in the fusion proteins of the present invention are engineered to have enhanced binding affinity according to, for example, the methods disclosed in PCT publication WO 2012/020006 (see Examples relating to affinity maturation) or U.S. Pat. Appl. Publ. No. 2004/0132066, the entire contents of which are hereby incorporated by reference. The ability of the fusion proteins of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antibody that competes with a reference antibody for binding to a particular antigen. In certain embodiments, such a competing antibody binds to the same epitope (e.g. a linear or a conformational epitope) that is bound by the reference antibody, Detailed exemplary methods for mapping an epitope to which an antibody binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Fusion proteins prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the fusion protein binds. For example, for affinity chromatography purification of fusion proteins of the invention, a matrix with protein A or protein G may be used. Sequential Protein A or G affinity chromatography and size exclusion chromatography can be used to isolate a fusion protein essentially as described in the Examples. The purity of the fusion protein can be determined by any of a variety of well-known analytical methods including gel electrophoresis, high pressure liquid chromatography, and the like. For example, the fusion proteins expressed as described in the Examples were shown to be intact and properly assembled as demonstrated by reducing and non-reducing SDS-PAGE (see e.g. FIG. 2).

Compositions, Formulations, and Routes of Administration

In a further aspect, the invention provides pharmaceutical compositions comprising any of the fusion proteins provided herein, e.g., for use in any of the below therapeutic methods. In one embodiment, a pharmaceutical composition comprises any of the fusion proteins provided herein and a pharmaceutically acceptable carrier. In another embodiment, a pharmaceutical composition comprises any of the fusion proteins provided herein and at least one additional therapeutic agent, e.g. as described below.

Further provided is a method of producing a fusion protein of the invention in a form suitable for administration in vivo, the method comprising (a) obtaining a fusion protein according to the invention, and (b) formulating the fusion protein with at least one pharmaceutically acceptable carrier, whereby a preparation of fusion protein is formulated for administration in vivo.

Pharmaceutical compositions of the present invention comprise a therapeutically effective amount of one or more fusion protein dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one fusion protein and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp, 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Fusion proteins of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularly, mucosally, intrapericardially, intraumbilically, intraocularly, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the fusion proteins of the invention.

Parenteral compositions include those designed for administration by injection, e.g. subcutaneous, intradermal, intralesional, intravenous, intraarterial intramuscular, intrathecal or intraperitoneal injection. For injection, the fusion proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The fusion proteins may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the fusion proteins provided herein may be used in therapeutic methods.

For use in therapeutic methods, fusion proteins of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, fusion proteins of the invention for use as a medicament are provided. In further aspects, fusion proteins of the invention for use in treating a disease are provided. In certain embodiments, fusion proteins of the invention for use in a method of treatment are provided. In one embodiment, the invention provides a fusion protein as described herein for use in the treatment of a disease in an individual in need thereof. In certain embodiments, the invention provides a fusion protein for use in a method of treating an individual having a disease comprising administering to the individual a therapeutically effective amount of the fusion protein. In certain embodiments the disease to be treated is an autoimmune disease. Exemplary autoimmune diseases include type 1 diabetes, psoriasis, asthma, rheumatoid arthritis, Crohn's disease, systemic lupus erythematosus (SLE) and multiple sclerosis. In one embodiment, the disease is transplant rejection or graft-versus-host disease. In a particular embodiment the disease is selected from the group of type 1 diabetes, Crohn's disease, SLE, and multiple sclerosis. In a more particular embodiment, the disease is type 1 diabetes. In certain embodiments the method further comprises administering to the individual a therapeutically effective amount of at least one additional therapeutic agent, e.g. an immunosuppressive agent if the disease to be treated is an autoimmune disease. An "individual" according to any of the above embodiments is a mammal, preferably a human.

In a further aspect, the invention provides for the use of a fusion protein of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is an autoimmune disease. In one embodiment, the disease is transplant rejection or waft-versus-host disease. In a particular embodiment the disease is selected from the group of type 1 diabetes, Crohn's disease, SLE, and multiple sclerosis. In a more particular embodiment, the disease is type 1 diabetes. In one embodiment, the method further comprises administering to the individual a therapeutically effective amount of at least one additional therapeutic agent, e.g., an immunosuppressive agent if the disease to be treated is an autoimmune disease. An "individual" according to any of the above embodiments may be a mammal, preferably a human.

In a further aspect, the invention provides a method for treating a disease in an individual, comprising administering to said individual a therapeutically effective amount of a fusion protein of the invention. In one embodiment a composition is administered to said individual, comprising a fusion protein of the invention in a pharmaceutically acceptable form. In certain embodiments the disease to be treated is an autoimmune disease. In one embodiment, the disease is transplant rejection or graft-versus-host disease. In a particular embodiment the disease is selected from the group of type 1 diabetes, Crohn's disease, SLE, and multiple sclerosis. In a more particular embodiment, the disease is type 1 diabetes. In certain embodiments the method further comprises administering to the individual a therapeutically effective amount of at least one additional therapeutic agent, e.g. an immunosuppressive agent if the disease to be treated is an autoimmune disease. An "individual" according to any of the above embodiments may be a mammal, preferably a human.

In some embodiments, an effective amount of a fusion protein of the invention is administered to a cell. In other embodiments, a therapeutically effective amount of a fusion protein of the invention is administered to an individual for the treatment of disease.

For the prevention or treatment of disease, the appropriate dosage of a fusion protein of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The fusion protein is suitably administered to the patient at one time or over a series of treatments. Depending on the type and severity of the disease, about 1 µg/kg to 15 mg/kg (e.g. 0.1 mg/kg-10 mg/kg) of fusion protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other non-limiting examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The fusion proteins of the invention will generally be used in an amount effective to achieve the intended purpose. For use to treat or prevent a disease condition, the fusion proteins of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the fusion proteins which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the fusion protein may not be related to plasma concentration. One having skill in the art will be able to optimize therapeutically effective local dosages without undue experimentation.

A therapeutically effective dose of the fusion proteins described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Fusion proteins that exhibit large therapeutic indices are preferred. In one embodiment, the fusion protein according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patients condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The fusion proteins of the invention may be administered in combination with one or more other agents in therapy. For instance, a fusion protein of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunosuppressive agent.

Such other agents are suitably present in combination in amounts that are effective for the purpose intended. The effective amount of such other agents depends on the amount of fusion protein used, the type of disorder or treatment, and other factors discussed above. The fusion proteins are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the fusion protein of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a fusion protein of the invention. The label or package insert indicates that the composition is used for treating the condition of choice. Moreover, the article of manufacture may comprise (a) a first container with a composition contained therein, wherein the composition comprises a fusion protein of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells. SEQ ID NOs 39-47 give exemplary leader peptides and polynucleotide sequences encoding them.

Preparation of IL-2R βγ Subunit-Fc Fusions and IL-2R α Subunit Fc Fusion

To study IL-2 receptor binding affinity, a tool was generated that allowed for the expression of a heterodimeric IL-2 receptor. The β-subunit of the IL-2 receptor was fused to an Fc molecule that was engineered to heterodimerize (Fc(hole)) (see SEQ NOs 21 and 22 (human), SEQ ID NOs 27 and 28 (mouse) and SEQ ID NOs 33 and 34 (cynomolgus)) using the "knobs-into-holes" technology (Merchant et al. Nat Biotech. 16, 677-681 (1998)). The γ-subunit of the IL-2 receptor was then fused to the Fc(knob) variant (see SEQ ID NOs 23 and 24 (human), SEQ ID NOs 29 and 30 (mouse) and SEQ ID NOs 35 and 36 (cynomolgus)), which heterodimerize with Fc(hole). This heterodimeric Fc-fusion protein was then used as a substrate for analyzing the IL-2/IL-2 receptor interaction. The IL-2R α-subunit was expressed as monomeric chain with an AcTev cleavage site and an Avi His tag (SEQ ID NOs 25 and 26 (human), SEQ ID NOs 31 and 32 (mouse) and SEQ ID NOs 37 and 38 (cynomolgus)). The respective IL-2R subunits were transiently expressed in HEK EBNA 293 cells with serum for the IL-2R βγ subunit construct and without serum for the α-subunit construct. The IL-2R βγ subunit construct was purified on protein A (GE Healthcare), followed by size exclusion chromatography (GE Healthcare, Superdex 200). The IL-2R α-subunit was purified via His tag on a NiNTA column (Qiagen) followed by size exclusion chromatography (GE Healthcare, Superdex 75). Amino acid and corresponding nucleotide sequences of various receptor constructs are given in SEQ ID NOs 21-38.

Preparation of Fusion Proteins

The DNA sequences were generated by gene synthesis and/or classical molecular biology techniques and subcloned into mammalian expression vectors under the control of an MPSV promoter and upstream of a synthetic polyA site, each vector carrying an EBV OriP sequence. Fusion proteins as applied in the examples below were produced by co-transfecting exponentially growing HEK293-EBNA cells with the mammalian expression vectors using calcium phosphate-transfection. Alternatively, HEK293 cells growing in suspension were transfected by polyethylenimine (PEI) with the respective expression vectors. Alternatively, stably transfected CHO cell pools or CHO cell clones were used for production in serum-free media. Subsequently, the fusion proteins were purified from the supernatant. Briefly, fusion proteins were purified by one affinity step with protein A (HiTrap ProtA, GE Healthcare) equilibrated in 20 mM sodium phosphate, 20 mM sodium citrate pH 7.5. After loading of the supernatant, the column was first washed with 20 mM sodium phosphate, 20 mM sodium citrate, pH 7.5 and subsequently washed with 13.3 mM sodium phosphate, 20 mM sodium citrate, 500 mM sodium chloride, pH 5.45. The fusion protein was eluted with 20 mM sodium citrate, 100 mM sodium chloride, 100 mM glycine, pH 3. Fractions were neutralized and pooled and purified by size exclusion chromatography (HiLoad 16/60 Superdex 200, GE Healthcare) in final formulation buffer: 20 mM histidine, 140 null NaCl pH 6.0. The protein concentration of purified protein samples was determined by measuring the optical density (OD) at 280 nm, using the molar extinction coefficient calculated on the basis of the amino acid sequence. Purity and molecular weight of fusion proteins were analyzed by SDS-PAGE in the presence and absence of a reducing agent (5 mM 1,4-dithiothreitol) and stained with Coomassie blue (SimpleBlue™ SafeStain, Invitrogen). The NUPAGE® Pre-Cast gel system (Invitrogen) was used according to the manufacturer's instructions (4-2.0% Tris-glycine gels or 3-12% Bis-Tris). Alternatively, purity and molecular weight of molecules were analyzed by CE-SDS analyses in the presence and absence of a reducing agent, using the Caliper LabChip GXII system (Caliper Lifescience) according to the manufacturer's instructions. The aggregate content of fusion protein samples was analyzed using a Superdex 200 10/300GL analytical size-exclusion column (GE Healthcare) in 2 mM MOPS, 150 mM NaCl, 0.02% NaN$_3$, pH 7.3 running buffer at 25° C. Alternatively, the aggregate content of antibody samples was analyzed using a TSKgel G3000 SW XL analytical size-exclusion column (Tosoh) in 25 mM K$_2$HPO$_4$, 125 mM NaCl, 200 mM L-arginine monohydrochloride, 0.02% (w/v) NaN$_3$, pH 6.7 running buffer at 25° C.

Figure 2:
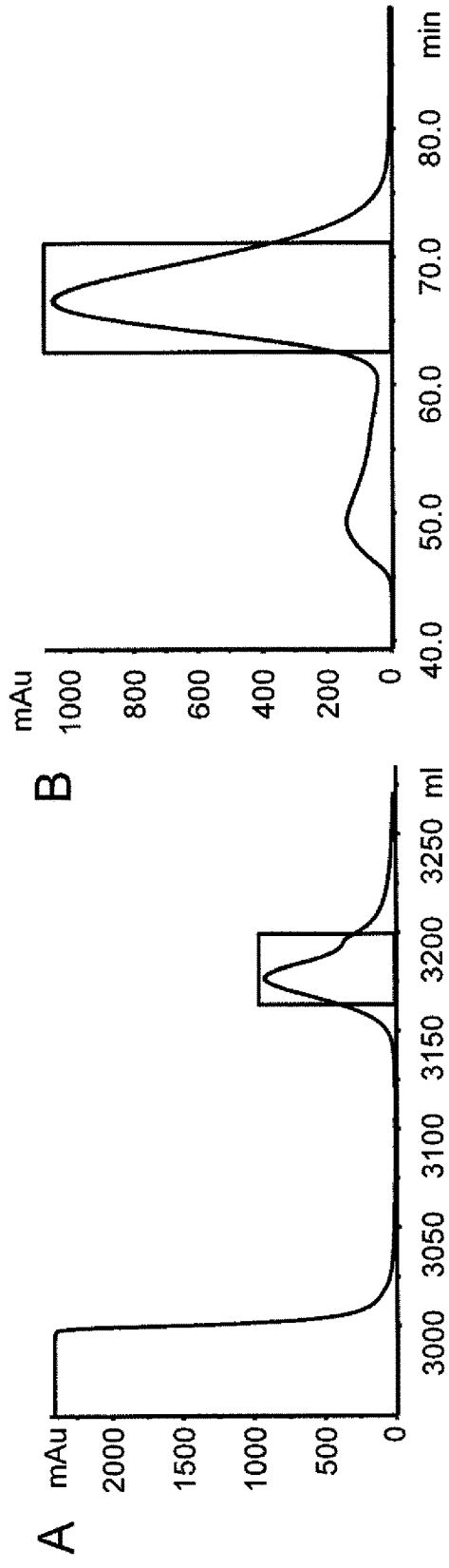
FIG. 2. Purification of DP47GS IgG-(IL-2)$_2$ fusion protein (see SEQ ID NOs 17, 19). (A) Elution profile of the Protein A affinity chromatography step. (B) Elution profile of the size exclusion chromatography step. Yield 13 mg/L. (C) Analytical capillary electrophoresis SDS (Caliper) of the final product. The following band were observed: non-reduced—2.3% area at 172.5 kDa, 97.7% area at 185 kDa; reduced—18.3% area at 27.3 kDa, 0.6% area at 29.2 kDa, 81.1% area at 78.3 kDa. (D)) Analytical size exclusion chromatography of the final product on a Superdex 200 column (100% monomer content).
Figure 2:
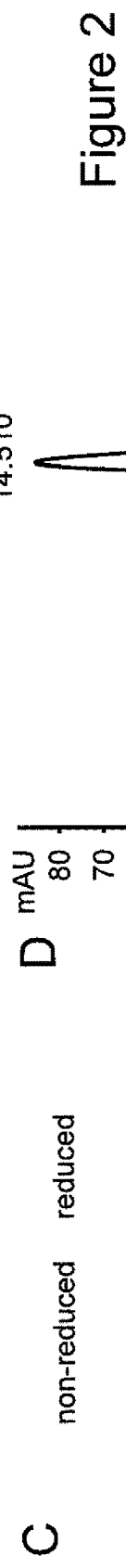
Figure 2:
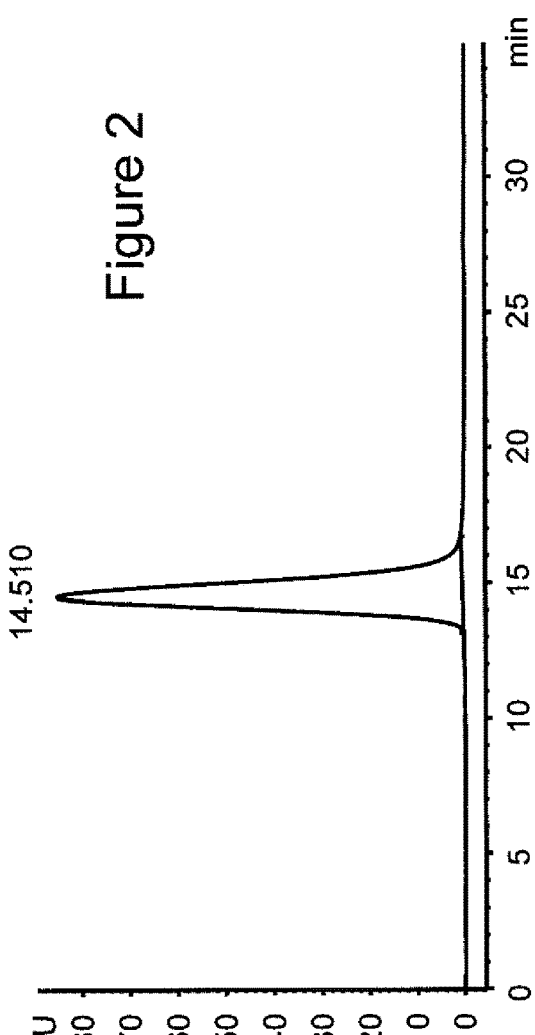

Results of the purification and characterization of the DP47GS IgG-IL-2 and DP47GS IgG-(IL-2)$_2$ constructs are shown in FIGS. 1 and 2.

Affinity to IL-2 Receptors

The affinity of the fusion proteins was determined by surface plasmon resonance (SPR) for the human, murine and cynomolgus IL-2R βγ heterodimer using recombinant IL-2R βγ heterodimer under the following conditions: ligand: human, murine and cynomolgus IL-2R β knob γ hole heterodimer immobilized on CM5 chip, analyte: DP47GS IgG-IL-2 (see SEQ ID NOs 13, 15 and 19) or DP47GS IgG-(IL-2)$_2$ (see SEQ ID NOs 17 and 19), temperature: 25° C., buffer: HBS-EP, analyte concentration: 300 nM down to 33 nM (1:3 dilutions), flow: 30 µl/min, association: 180 s, dissociation: 300 s, regeneration: 6.0 s 3M MgCl$_2$, fitting: 1:1 binding, RI≠0, Rmax=global. The affinity of the fusion proteins was also determined by surface plasmon resonance (SPR) for the human, murine and cynomolgus IL-2R α-subunit using recombinant monomeric IL-2R α-subunit under the following conditions: ligand: human, murine and cynomolgus IL-2R α-subunit immobilized on a CM5 chip, analyte: DP47GS IgG-IL-2 or DP47GS IgG-(IL-2)$_2$, temperature: 25° C., buffer: HBS-EP, analyte concentration 100 nM down to 3.1 nM (1:3 dilutions), flow: 30 µl/min, association: 60 s, dissociation: 180 s, regeneration: none, fitting: 1:1 binding, RI=0, Rmax=global.

Results of the kinetic analysis with the IL-2R βγ heterodimer or the IL-2R α-subunit are given in Table 1.

TABLE 1

Binding of fusion proteins to IL-2R βγ and IL-2R α.

| K$_D$ in nM | Hu IL-2R βγ | Cy IL-2R βγ | Mu IL-2R βγ | Hu IL-2R α | Cy IL-2R α | Mu IL-2R α |
|---|---|---|---|---|---|---|
| DP47GS IgG-IL-2 | 3.1 | 4.6 | 15 | 28 | 29 | 71 |
| DP47GS IgG-(IL2)$_2$ | 2 | 3 | 8.4 | n.d. | n.d. | n.d. |

The affinity of human IL-2 to the human IL 2R βγ heterodimer is described to be around 1 nM, while the fusion proteins both have a slightly lower affinity between 2 and 3 nM. The affinity to the murine IL-2R is several times weaker than for the human and cynomolgous IL-2R.

Expression of IL-2 Receptors on Immune Cells

The high-affinity trimeric IL-2 receptor is composed of the α (IL-2RA, CD25), β (IL-2RB, CD122) and γ (IL-2RG, CD132) chains and has a K$_D$ of ~10 pM. CD25 alone has only a low affinity (K$_D$ ~10 nM) for IL-2. The IL-2RB/IL-2RG dimer, which is expressed on some cell types in the absence of IL-2RA, also binds IL-2 but with an intermediate affinity (K$_D$ ~1 nM). Signalling via the IL-2 receptor is mediated by the IL-2RB and chains. From crystal structure analyses, IL-2RA does not seem to contact either IL-2RB or IL-2RG. It has been proposed that the basis of the cooperativity of the trimeric receptor is an entropy reduction when CD25 captures IL-2 at the cell surface for presentation to IL-2RB and IL-2RG, or alternatively a CD25-induced alteration in IL-2 conformation occurs, thus stabilizing the complex. In Foxp3$^+$ regulatory CD4$^+$ cells, there is a large stoichiometric excess of IL-2RA as compared to the β and γ chains of the receptor supporting the hypothesis that dimers, or even larger complexes, of the a chain aid in the binding of IL-2. There is also evidence that CD25 on one cell can present IL-2 to IL-2RB/IL-2RG dimers on another cell, in a high-affinity, intercellular interaction emphasizing the unique relationship amongst the three chains composing the high affinity IL-2 receptor.

Figure 3:
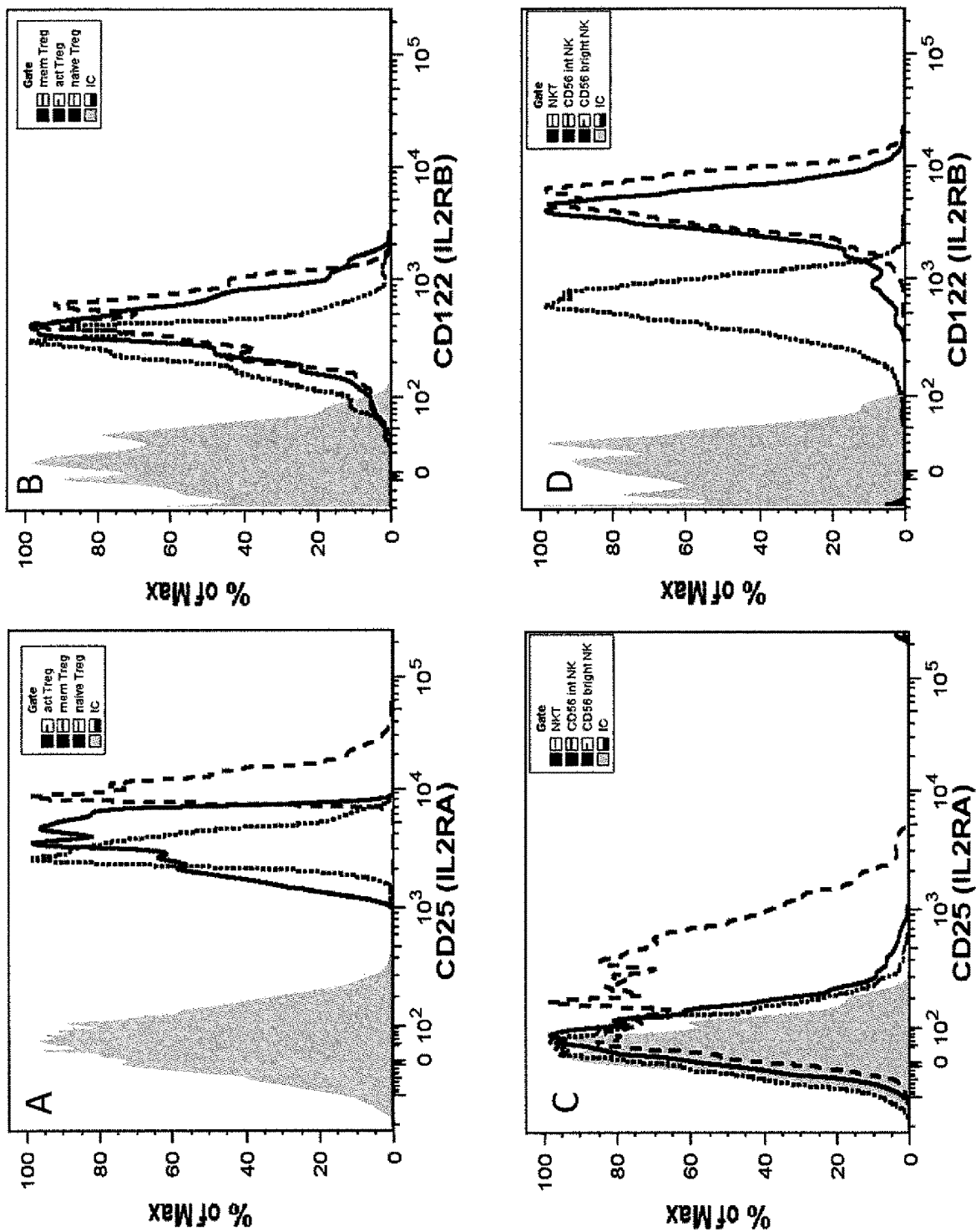
FIG. 3. CD25 (IL-2RA) and CD122 (IL-2RB) expression on CD4$^+$ T$_{reg}$ subsets, NK cell subsets and NKT cells. Cell surface markers were used to define CD4+ T$_{reg}$ subsets, NKT cells and NK cells. In order to optimize staining for CD25 and CD122, intracellular Foxp3 staining was not performed, (A, B) Three regulatory CD4+ T cell (T$_{rlg}$) populations: naïve (CD45RA+, CD25+; dotted line), memory (CD45RA−, CD25+; solid line) and activated (CD45RA−, CD25$^{hi}$; dashed line). (C, D) NKT (dotted line), CD56$^{bright}$ NK cells (dashed line), CD56$^{intermediate}$ NK cells (solid line). Grey: isotype control.
Figure 4:
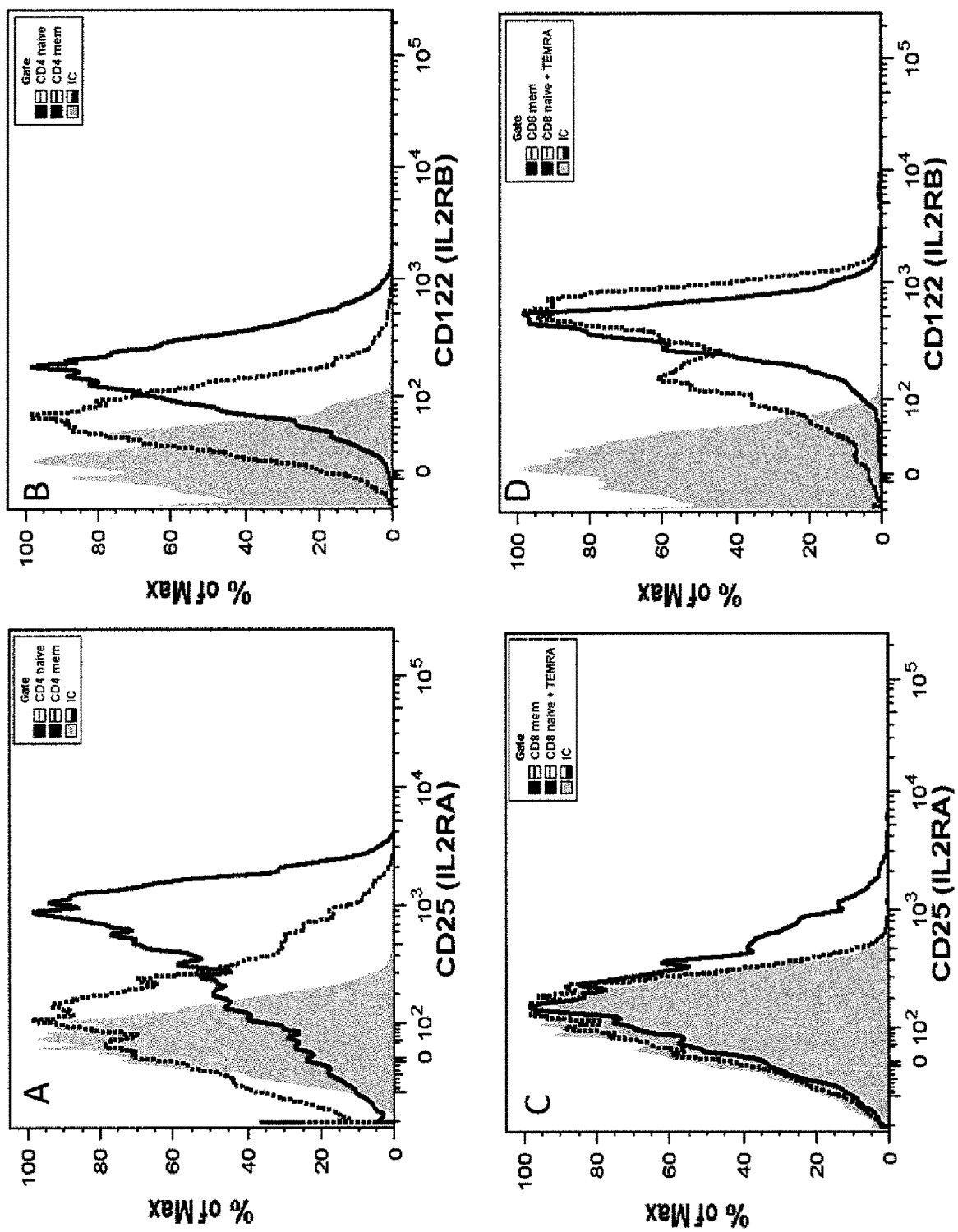
FIG. 4. CD25 (IL-2RA) and CD122 (IL-2RB) expression on CD4+ and CD8+ conventional T cell subsets. Cell surface markers were used to define naïve (CD45RA+; dotted line) and memory (CD45RA−; solid line) conventional CD4+ T cells (A, B), memory conventional CD8+ T cells (CD45RA−; solid line) and CD45RA+ CD8 T cells (a combination of the naïve and TEMRA subsets; TEMRA refers to effector memory cells that have reverted to expressing CD45RA; dotted line) (C, D). Grey: isotype control.

CD25 (IL-2RA) and CD122 (IL-2RB) expression on CD4$^+$ T$_{reg}$ subsets, NK cell subsets and NKT cells, as well as on CD4$^+$ and CD8+ conventional cell subsets was determined by FACS (FIGS. 3 and 4). Cell surface markers were used to define CD4$^+$ T$_{reg}$ subsets, NKT cells and NK cells (FIG. 3). In order to optimize staining for CD25 and CD122, intracellular Foxp3 staining was not performed. Briefly, using 150 μl blood donated by a healthy volunteer, fluorescent antibodies were incubated for 45 min at room temperature in the dark (vortexed at the beginning and after 20 min). Red blood cells were lysed with BD lysis buffer (BD FACS Lysing Solution, 349202) for 9 minutes and the remaining cells were washed (2 ml of PBS+0.1% BSA) and fixed (1% PFA). Cells were analysed on an LSRFortessa cell analyser (Becton Dickinson) and data analysed using FloJo software (TreeStar). T$_{reg}$ subsets were identified using antibodies specific for TCRαβ-FITC (IP26, BioLegend), CD4-Alexa Fluor 700 (RPA-T4, BioLegend), CD127-PE/CY7 (ebioRDR5, Ebioscience), CD45RA-Pacific Blue (HI100, BioLegend), CD25-APC (2A3, M-A251, BD Biosciences) and CD122-PE (TU27, BioLegend). NK and NKT cells were stained in a separate tube with antibodies specific for TCRαβ-FITC, CD4-Alexa Fluor 700, CD8-PE/CY (HTT8a, BioLegend), CD56-Pacific Blue (HCD56, BioLegend), CD25-APC and CD122-PE. Following the gating of lymphocytes based on FSC/SSC and excluding doublets, naïve T$_{reg}$s were identified as TCRαβ$^+$, CD4$^+$, CD127$^-$, CD25$^+$, CD45RA$^+$, memory T$_{reg}$s were identified as TCRαβ$^+$, CD4$^+$, CD127$^-$, CD25$^+$, CD45RA$^-$ and activated T$_{reg}$s were identified as TCRαβ$^+$, CD127$^-$, CD25$^{high}$, CD45RA$^-$. NK cells were identified as TCRαβ$^-$, CD56$^+$ and activated. NK cells identified as TCRαβ$^-$, CD56$^{bright}$. NKT cells were identified as TCRαβ$^-$, CD56$^+$. Isotype controls conjugated to APC and PE were used in order to estimate background fluorescence for CD25 and CD122, respectively.

Similarly, cell surface markers were used to define naïve and memory conventional CD4$^+$ T cells (FIGS. 4A and 4B), memory conventional CD8$^+$ T cells and CD45RA$^+$ CD8 T cells (a combination of the naïve and TEMRA subsets; TEMRA refers to effector memory cells that have reverted to expressing CD45RA) (FIGS. 4C and 4D). Staining and analysis was performed as described above, Using the same tube described above to characterize CD4$^+$ T$_{reg}$s, CD4$^+$ conventional naïve T cells were identified as TCRαβ$^+$, CD4$^+$, CD127$^+$, CD25$^{-/+}$, CD45RA$^+$ and CD4$^+$ conventional memory T cells were identified as TCRαβ$^+$, CD127$^+$, CD25$^{-/+}$, CD45RA$^-$. CD8 T cells were defined using TCRαβ-FITC, CD8-Alexa Fluor 700 (HTT8a, BioLegend), CD28-PE/CY7 (CD28.2, BioLegend), CD45RA-Pacific Blue, CD25-APC and CD122-PE. CD8$^+$ memory T cells were identified as TCRαβ$^+$, CD8$^+$, CD45RA$^-$. CD8$^+$ naïve and TEMRA (TEMRA refers to effector memory cells that have reverted to expressing CD45RA T cells) were identified as TCRαβ$^+$, CD8$^+$, CD45RA$^+$. CD28 was not used to distinguish CD8$^+$ naïve T cells from CD8$^+$ TEMRA T cells since the CD28 marker was not included in the pSTAT5a analysis described below (see FIG. 5).

In FIGS. 3 and 4, the cell-specific expression of IL-2RA and IL-2RB is shown for subsets of T cells, NK cells and NK cells in human peripheral blood (IL-2RG has essentially ubiquitous expression on hematopoietic cells since it partners with a large number of cytokine receptors). The highest level of IL-2RA is present on the three regulatory CD4$^+$ T cell (T$_{reg}$) populations: naïve (CD45RA$^+$, CD25$^+$), memory (CD45RA$^-$, CD25$^+$) and activated (CD45RA$^-$, CD25$^{hi}$) (FIG. 3A). On average, conventional memory CD4$^+$ T cells express approximately 10-fold less CD25 than T$_{reg}$s (FIG. 4A). The expression of CD25 on naïve CD4$^+$ T cells varies significantly amongst donors but is always lower than that observed on memory CD4$^+$ T cells (FIG. 4A). Expression of CD25 on NK, NKT and CD8 T cells is very low or not detectable except for CD56$^{bright}$ NK cells (FIGS. 3C and 4C). The CD56$^{bright}$ NK and CD56$^+$ NK cells express the highest level of IL-2RB (FIG. 3D), approximately 10-fold more than any of the T cell subsets, including NKT cells (FIGS. 3B, 3D, 4B, 4D).

Induction of pSTAT5a in Human Peripheral Blood Cell Subsets

Following IL-2-induced oligomerization of the trimeric IL-2R, the JAK1 and JAK3 cytoplasmic protein tyrosine kinases, that are associated with the intracellular domains of IL-2RB and IL-2RG respectively, become activated. These kinases phosphorylate certain IL-2RB tyrosine residues that act as docking sites for STAT5a and STAT5b that are in turn phosphorylated. The IL-2-induced activation of several signalling pathways eventually results in the transcription of target genes that contribute to the various functions associated with the IL-2/IL-2R pathway. Since various cell types express different levels of the IL-2 receptor IL-2RA and IL-2RB molecules (FIGS. 3 and 4), in order to understand the integrated signalling response to IL-2 mediated by various combinations of the high and intermediate affinity receptors we measured pSTAT5a levels within individual cells by polychromatic flow cytometry.

Figure 5:
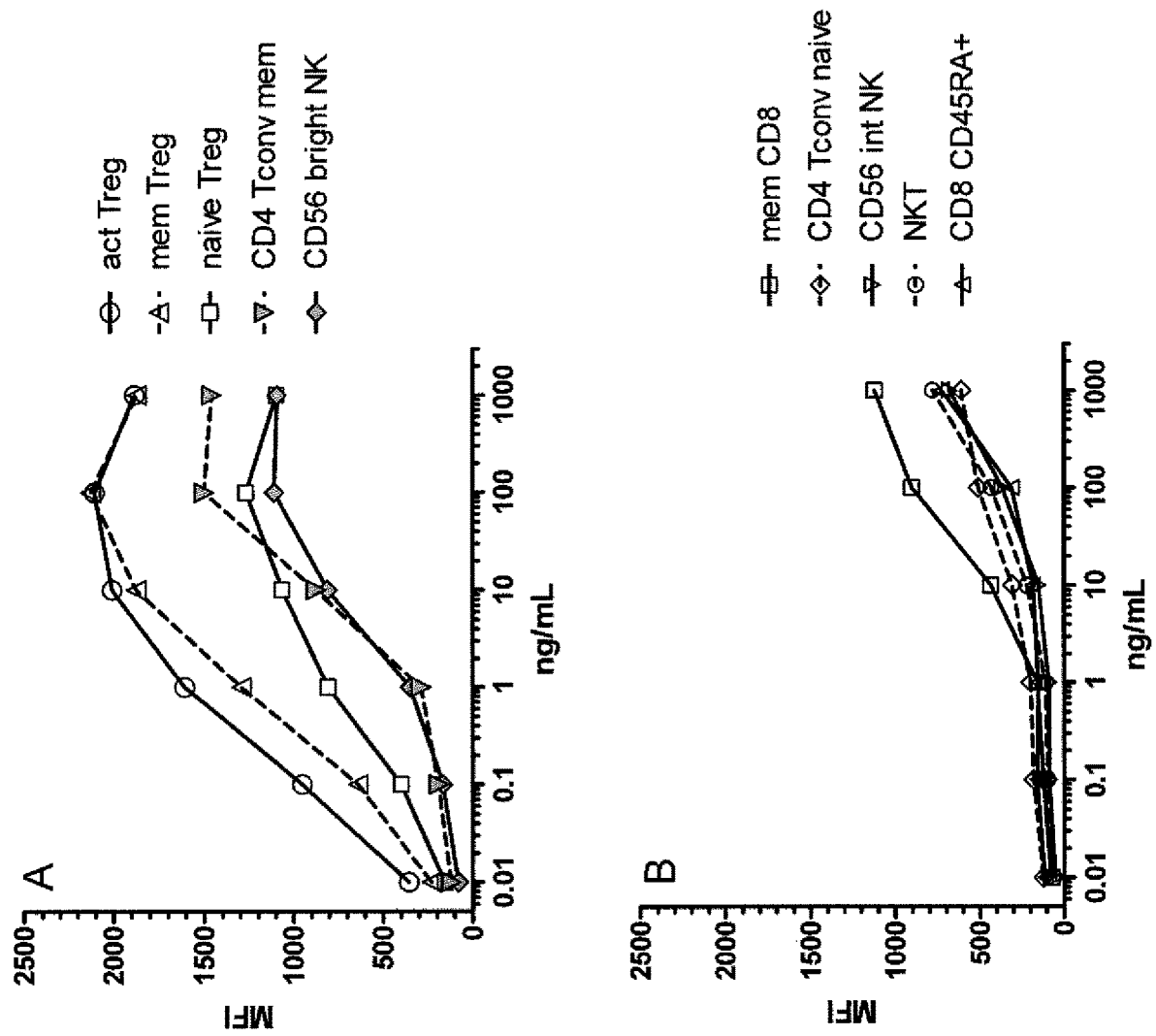
FIG. 5. Induction of pSTAT5a in human peripheral blood cell subsets in response to DP47GS IgG-IL-2. The effects of various doses of DP47 IgG-IL-2 on the induction of STAT5a phosphorylation are shown in human CD4+ Treg subsets, naïve and memory conventional CD4+ T cells, memory conventional CD8+ T cells, CD45RA+ CD8 T cells, NKT cells and NK cells.
Figure 6:
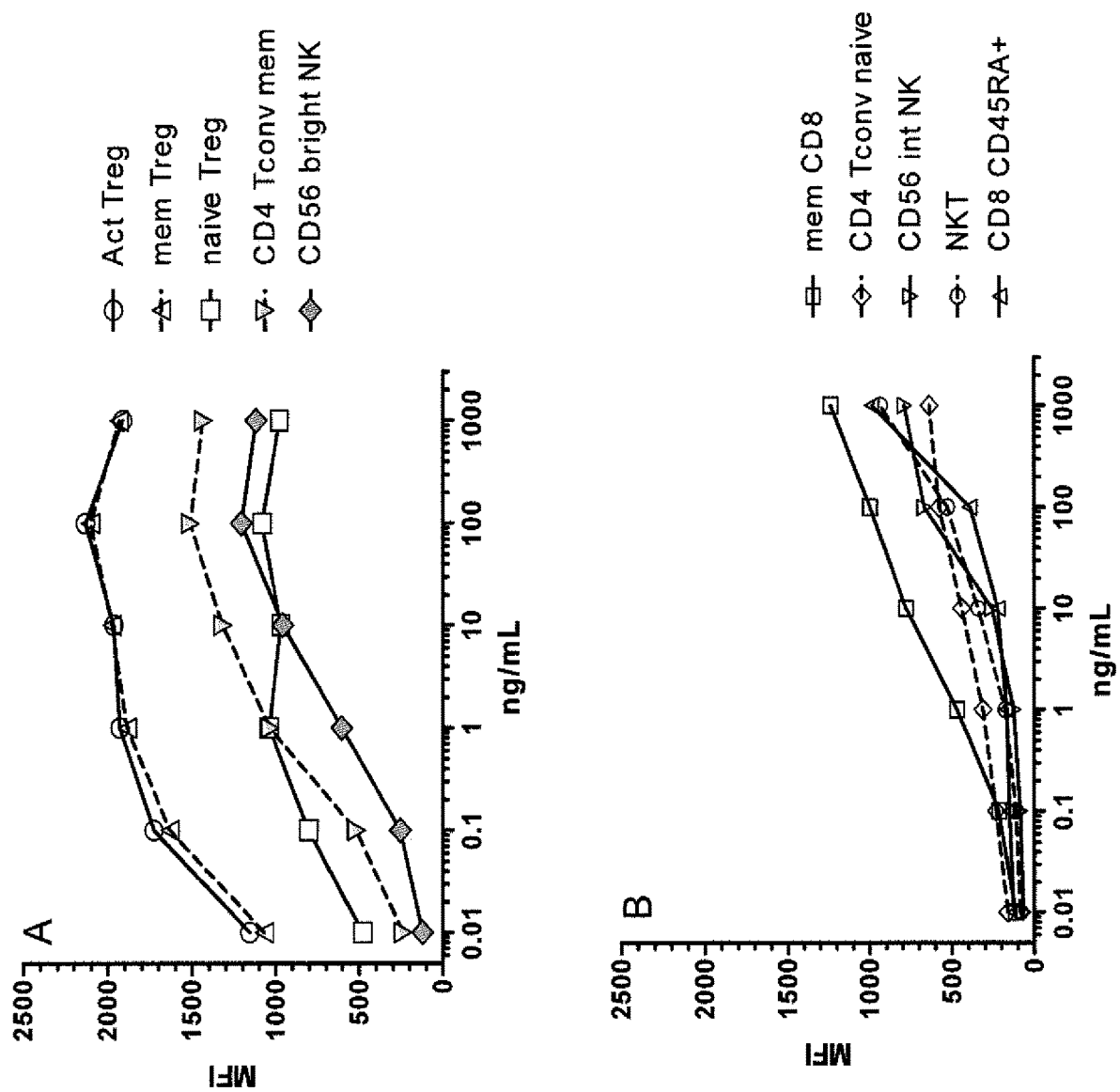
FIG. 6. Induction of pSTAT5a in human peripheral blood cell subsets in response to DP47GS IgG-(IL-2)$_2$. The effects of various doses of DP47 IgG-(IL-2)2 immunoconjugate are shown on the induction of STAT5a phosphorylation in human CD4+ Treg subsets, naïve and memory conventional CD4+ T cells, memory conventional CD8+ T cells, CD45RA+ CD8 T cells, NKT cells and NK cells.

The effects of various doses of DP47GS IgG-IL-2 or DP47GS IgG-(IL-2)$_2$ on the induction of STAT5a phosphorylation were assessed in human CD4$^+$ T$_{reg}$ subsets, naïve and memory conventional CD4$^+$ T cells, memory conventional CD8$^+$ T cells, CD45RA$^+$ CD8 T cells, NKT cells and NK cells (FIGS. 5 and 6). All subsets were characterized in a single tube for each dose. Briefly, blood from a healthy volunteer was drawn into heparinized tubes. Various concentrations of DP47GS IgG-IL-2 or DP47GS IgG-(IL-2)$_2$ were added to 500 μl of blood and incubated at 37° C. After 30 minutes the blood was lysed and fixed using pre-warmed lyse/fix buffer (Becton Dickinson #558049) for 10 minutes at 37° C., washed 2× with PBS containing 0.2% BSA followed by permeabilization with −20° C. pre-cooled methanol (Sigma, Biotech grade #494437) for 20 minutes on ice. The cells were then extensively washed 4× with PBS containing 0.2% BSA before FACS staining was performed using a panel of fluorescent antibodies to distinguish different lymphocyte and NK cell subpopulations and pSTAT5a status. The antibodies utilized were anti-CD4-Alexa Fluor 700 (clone RPA-T4), CD3-PerCP/Cy5.5 (UCHT1), CD45RA-PE/Cy7 (HI100), CD8-Brilliant Violet 605 (RPA-T8), CD56-Brilliant Violet 421 (HCD56), Foxp3-PE (259D) (all from BioLegend), CD25-APC (clones M-A251 & 2A3) and pSTAT5a-Alexa Fluor 488 (pY694) (Becton Dickinson). Samples were acquired using an LSRFortessa cell analyser (Becton Dickinson) and data analysed using FloJo software (TreeStar). After gating on lymphocytes and excluding doublets, T$_{reg}$s were defined as CD3$^+$, CD4$^-$, Foxp3$^+$ and subdivided as CD45$^-$Foxp3$^{hi}$ (activated T$_{reg}$), $CD3^+$, $CD4^+$, $CD45RA^-$, $Foxp3^+$ (memory $T_{reg}$) and $CD3^+$, $CD4^+$, $CD45^+$, $Foxp3^+$ (naïve $T_{reg}$). Conventional $CD4^+$ T cells were defined as $CD3^+$, $CD4^+$, $CD45RA^+$ (naïve) and $CD3^+$, $CD4^+$, $CD45RA^-$ (memory). CD8 T cells were defined as $CD3^+$, $CD8^+$, $CD45RA^-$ (memory) and $CD3^+$, $CD8^+$, $CD45RA^+$. NKT cells were defined as $CD3^+$, $CD56^+$ and NK cells were defined as $CD3^-$, $CD56^{bright}$ (activated NK cells) or $CD3^-$, $CD56^{int}$. Intracellular pSTAT5a levels were quantified in all cell subsets at all doses.

FIG. 5 shows the dose response of the DP47GS IgG-IL-2 immunoconjugate on T cells, NK cells and NK T cells in human peripheral blood. The hierarchy of responsiveness to DP47GS IgG-IL-2 was the same as that observed when recombinant human IL-2 was used (data not shown): all three $T_{reg}$ populations, naïve ($CD45RA^+$, $CD25^+$), memory ($CD45RA^-$, $CD25^+$) and activated ($CD45RA^-$, $CD25^{hi}$) increased pSTAT5 levels at the 0.1 ng/ml concentration of DP47GS IgG-IL-2 whereas other cell populations required 1 ($CD56^{bright}$ NK and memory $CD4^+$ T cells), 10 (memory $CD8^+$ T cells), or 100 ng/ml ($CD56^+$ NK cells, naïve $CD4^+$ T cells, NKT cells and $CD45RA^+$ CD8 T cells) DP47 IgG-IL-2 to produce detectable increases in pSTAT5a. Also see FIG. 8 for detailed dose responses by the $T_{reg}$ populations that display their high sensitivity for DP47GS IgG-IL-2. It is notable that the high expression of IL-2RB on NK cells with intermediate levels of CD56 (FIG. 3D) as compared to IL-2RB expression on T cell subsets is not sufficient to allow $T_{reg}$-like IL-2 sensitivity (FIG. 5B). Overall, activated, memory and naive $T_{reg}$ subsets showed the greatest sensitivity to DP47GS IgG-IL-2, while $CD56^{bright}$ NK cells and $CD4^+$ conventional memory T cells were 20-50 fold less sensitive, respectively. Amongst the other subsets analysed, increased pSTAT5a was detected in memory $CD8^+$ T cells at a 10-fold higher concentration of DP47 IgG-IL-2 than that observed to induce pSTAT5a in $CD4^+$ conventional memory T cells. Naïve $CD4^+$ and $CD8^+$ T cells, NKT cells and "resting" NK cells (positive, not bright staining for CD56) were relatively insensitive to the immunoconjugate (FIG. 5B).

Figure 7:
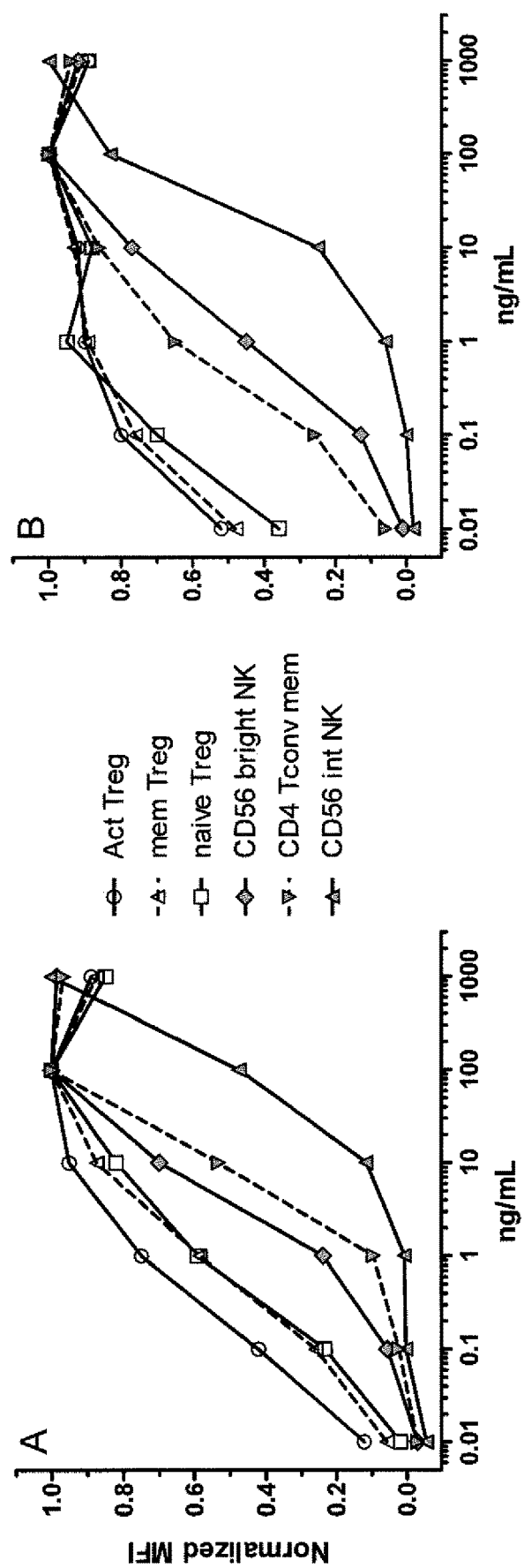
FIG. 7. Induction of pSTAT5a in human peripheral blood cell subsets: comparison of DP47GS IgG-IL-2 and DP47GS IgG-(IL-2)$_2$.
Figure 8:
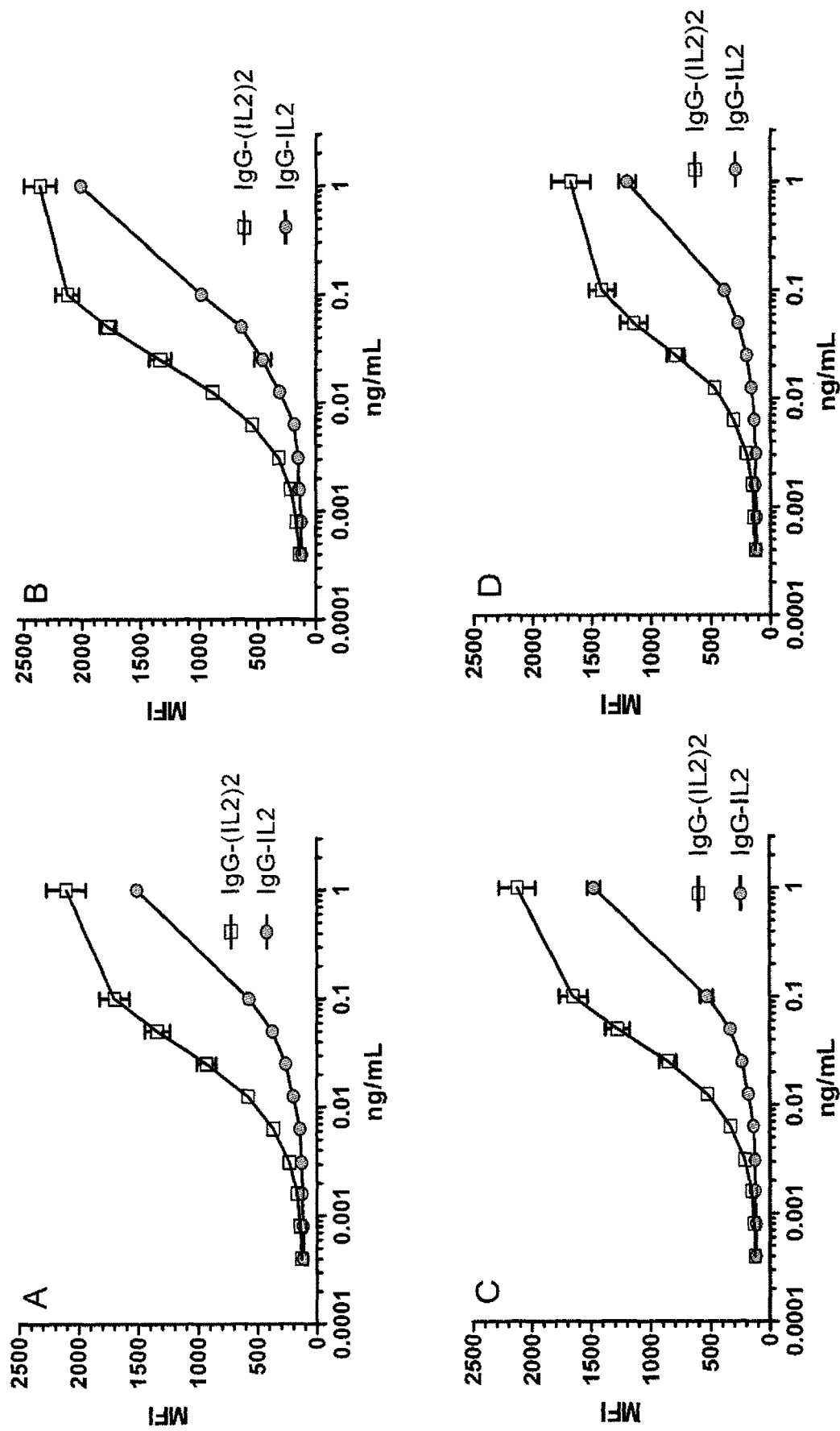
FIG. 8. Detailed examination of T$_{reg}$ subset sensitivity in three donors comparing DP47GS IgG-IL-2 and DP47GS IgG-(IL-2)$_2$. Graphs represent the average and SE of the pSTAT5a MFI for the three donors. (A) Total CD3+, CD4+, Foxp3+ T$_{reg}$s. (B) Activated T$_{reg}$s. (C) Memory T$_{reg}$s. (D) Naïve T$_{reg}$s.

As observed for DP47GS IgG-IL-2 (FIG. 5), the $T_{reg}$ subsets were the cells most sensitive to DP47GS IgG-$(IL-2)_2$ induced pSTAT5a (FIGS. 6 and 8). To more readily compare DP47GS IgG-IL-2 and DP47GS IgG-$(IL-2)_2$, the pSTAT5a values were normalized (FIG. 7). To normalize MFI values, unstimulated pSTAT5a MFI values specific for each gated subset were subtracted from all stimulated MFI values for that cell subset. The resulting values were divided by the highest pSTAT5a MFI value obtained by that subset in the dose response. The $EC_{50}$s were estimated based on the amount of IL-2 fusion protein required to reach 50% of the maximal pSTAT5a MFI observed for that subset. As shown in FIG. 7, the DP47GS IgG-$(IL2)_2$ immunoconjugate produced a more potent and selective induction of pSTAT5a in cells constitutively expressing CD25, potentially as a consequence of increased avidity of the immunoconjugate for the high affinity IL-2 receptor. The $EC_{50}$ for pSTAT5a activation was observed to be 20-60 fold lower in $T_{reg}$ when directly comparing DP47GS IgG-$(IL-2)_2$ to DP47GS IgG-IL-2. Table 2 summarizes the $EC_{50}$ values and fold differences for pSTAT5a activation by DP47GS IgG-IL-2 vs. DP47GS IgG-$(IL-2)_2$ in the different cell subsets.

TABLE 2

$EC_{50}$ values and fold differences for pSTAT5a activation by DP47GS IgG-IL-2 vs. DP47GS IgG-$(IL-2)_2$ in different cell subsets.

| T cell | IgG-IL-2 | IgG-$(IL-2)_2$ | Fold change |
|---|---|---|---|
| activated $T_{reg}$ | 0.20 ng/mL | 0.010 ng/mL | 20 |
| memory $T_{reg}$ | 0.60 ng/mL | 0.010 ng/mL | 60 |
| naïve $T_{reg}$ | 0.60 ng/mL | 0.025 ng/mL | 24 |
| $CD56^{bright}$ NK | 3.5 ng/mL | 1.5 ng/mL | 2.3 |
| CD4 Tconv mem | 10 ng/mL | 0.4 ng/mL | 25 |
| $CD56^{intermediate}$ NK | 100 ng/mL | 25 ng/mL | 4 |

Even at extremely limiting concentrations, DP47GS IgG-$(IL-2)_2$ produced higher levels of pSTAT5a as compared to DP47GS IgG-IL-2 (FIG. 8). For this experiment, blood from three healthy volunteers were tested individually on the same day for responses to a 2-fold titration of DP47 IgG-IL-2 and DP47 IgG-$(IL-2)_2$ at limiting concentrations. Graphs in FIG. 8 represent the average and SE of the pSTAT5a MFI for the three donors. In addition to the three $T_{reg}$ subsets examined individually (FIG. 8B-D), a gate was applied to assess pSTAT5a in total $CD3^+$, $CD4^+$, $Foxp3^+$ Tregs (FIG. 8A), Polychromatic flow cytometry was performed as described above (see FIG. 5).

$CD4^+$ conventional memory T cells also responded to lower (25-fold) concentrations of DP47GS IgG-$(IL-2)_2$ as compared to DP47GS IgG-IL-2. However, although the $EC_{50}$ values were reduced for $CD56^{bright}$ NK cells and NK cells when comparing DP47GS IgG-$(IL-2)_2$ to DP47 IgG-IL-2, the reductions were only 2.3-fold and 4-fold, respectively. This is likely due to the reliance of these cells on the intermediate affinity IL-2 receptor for IL-2-mediated signalling. This differential shift in the $ED_{50}$ for $T_{reg}$s vs. NK cells increases the preference for $T_{reg}$ activation several fold.

Induction of pSTAT5a in Cynomolgus Peripheral Blood Cell Subsets

As observed in human peripheral blood, there is a preferential induction of pSTAT5a in $T_{reg}$ subsets in cynomolgus peripheral blood stimulated with DP47GS IgG-IL-2. In a direct comparison of the ability of DP47GS IgG-$(IL-2)_2$ and DP47GS IgG-IL-2 to induce pSTAT5a in the three $T_{reg}$ subsets, 2-8 fold less DP47GS IgG-$(IL-2)_2$, was required to reach 50% of the maximal phosphorylation level (Table 3).

Similar to human whole blood, cell surface and intracellular markers were used to identify regulatory T cell subsets and conventional T cells in whole blood from normal healthy cynomolgus monkeys. Blood samples were collected on the same day from three healthy cynomolgus monkeys in sodium heparin tubes and various concentrations of DP47GS IgG-IL-2 or DP47GS IgG-$(IL-2)_2$ were added to 500 μl of blood and incubated at 37° C. After 10 min at 37° C., samples were lysed and fixed with pre-warmed BD Lyse/Fix buffer (BD Biosciences). After washing, cells were permeabilized with 1 mL methanol for 30 min on ice. Samples were washed 3 times and stained with a panel of FoxP3-Alexa Fluor® 647 (clone: 259D, BioLegend), CD4-V500 (clone: L200, BD Biosciences), CD45RA-V450 (clone: 5H9, BD Biosciences), CD25-PE (clone: 4E3, eBioscience), pSTAT5a-Alexa Fluor® 488 (clone: 47, BD Biosciences), and Ki-67-PerCP-Cy5.5 (clone: B56, BID Biosciences) for 1 hour at 4° C. All the samples were acquired by an LSRFortessa cell analyser (Becton Dickinson) and then analysed with FlowJo software (Tree star, Inc., Ashland, USA).

Table 3 summarizes the $EC_{50}$ values for pSTAT5a activation by DP47GS IgG-IL-2 vs. DP47GS IgG-(IL-2)$_2$ in the different cell subsets.

TABLE 3

Induction of pSTAT5a in cynomolgus peripheral blood cell subsets in response to DP47GS IgG4L-2 and DP47GS IgG-(IL-2)$_2$.

| T cell | IgG-IL-2 | IgG-(IL-2)$_2$ |
| --- | --- | --- |
| activated $T_{reg}$ | 0.070 ng/mL | 0.020 ng/mL |
| memory $T_{reg}$ | 0.210 ng/mL | 0.025 ng/mL |
| naïve $T_{reg}$ | 0.040 ng/mL | 0.020 ng/mL |
| memory $T_{conv}$ | >0.400 ng/mL | >0.100 ng/mL |

Induction of $T_{reg}$ Number in Cynomolgus Monkeys

Figure 9:
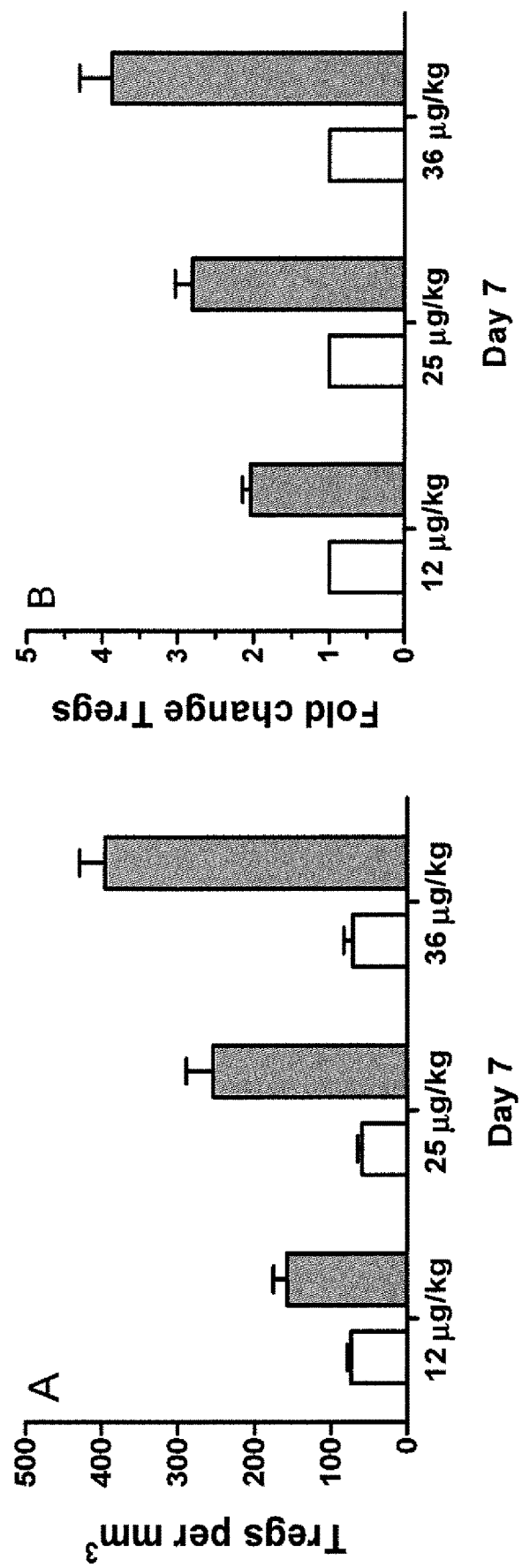
FIG. 9. DP47GS IgG-IL-2 has a dose dependent effect in cynomolgus monkeys increasing regulatory T cells. The changes in whole blood CD4+, CD25+, FoxP3+, regulatory T cells on day 7 post treatment are shown as the absolute cell number per mm$^3$ of whole blood (A) and the fold change in T$_{reg}$s (B); all data are represented as the mean±SEM. Shaded bars: DP47GS IgG-IL-2 (n=6); open bars: vehicle (n=3).

Cynomolgus animals treated in vivo with DP47GS IgG-IL-2 had dose-dependent increases in the absolute number of $T_{reg}$s as well as the fold increase above baseline 7 days post dosing (FIGS. 9A and 9B, respectively). Normal healthy cynomolgus monkeys of both sexes at ages ranging from 3 to 6 years were used in all tests and no animal was used more than once. While under anaesthesia, various doses of DP47GS (n=6) or vehicle (n=3) were injected SC on the lateral dorsum. Individual doses of DP47GS IgG-IL-2 were based on body weight and formulated for injection in a vehicle of sterile PBS pH 7.2 containing 0.5% sterile cynomolgus serum. Blood samples were collected at various times post treatment and tested for haematological changes (CBC and Differential) with an Advia Automated Hematology Analyser as well as cell surface and intracellular markers detailed above (experimental procedures for Table 3). The changes in whole blood CD4$^+$, CD25$^+$, FoxP3$^+$, regulatory T cells on day 7 post treatment are shown in FIG. 9 as the absolute cell number per mm$^3$ of whole blood (FIG. 9A) and the fold change in $T_{reg}$s (FIG. 9B); all data are represented as the mean±SEM. At the higher doses of 25 μg/kg and 36 μg/kg DP47GS IgG-IL-2, average $T_{reg}$ increases of nearly 3-fold (range of 111-255%) and 4-fold (range of 110-470%), respectively, were observed. Without wishing to be bound by theory, the ~2 increase in $T_{reg}$s (ranging from 67-133%) with the 12 μg/kg DP47GS IgG-IL2 dose represents about the desirable increase in $T_{reg}$s. There is a large range in the numbers of $T_{reg}$s in humans (20-90 $T_{reg}$s per mm$^3$ of blood; 4 to 10% of CD4$^+$ cells) and it is reasonable to assume that an increase of $T_{reg}$s induced by IL-2 within an individual will result in an overall increase in functional suppression. It might be desirable, however, not to increase $T_{reg}$ numbers above the normal range for this cell population for a sustained period of time, but primarily enhance the function of these cells.

Figure 10:
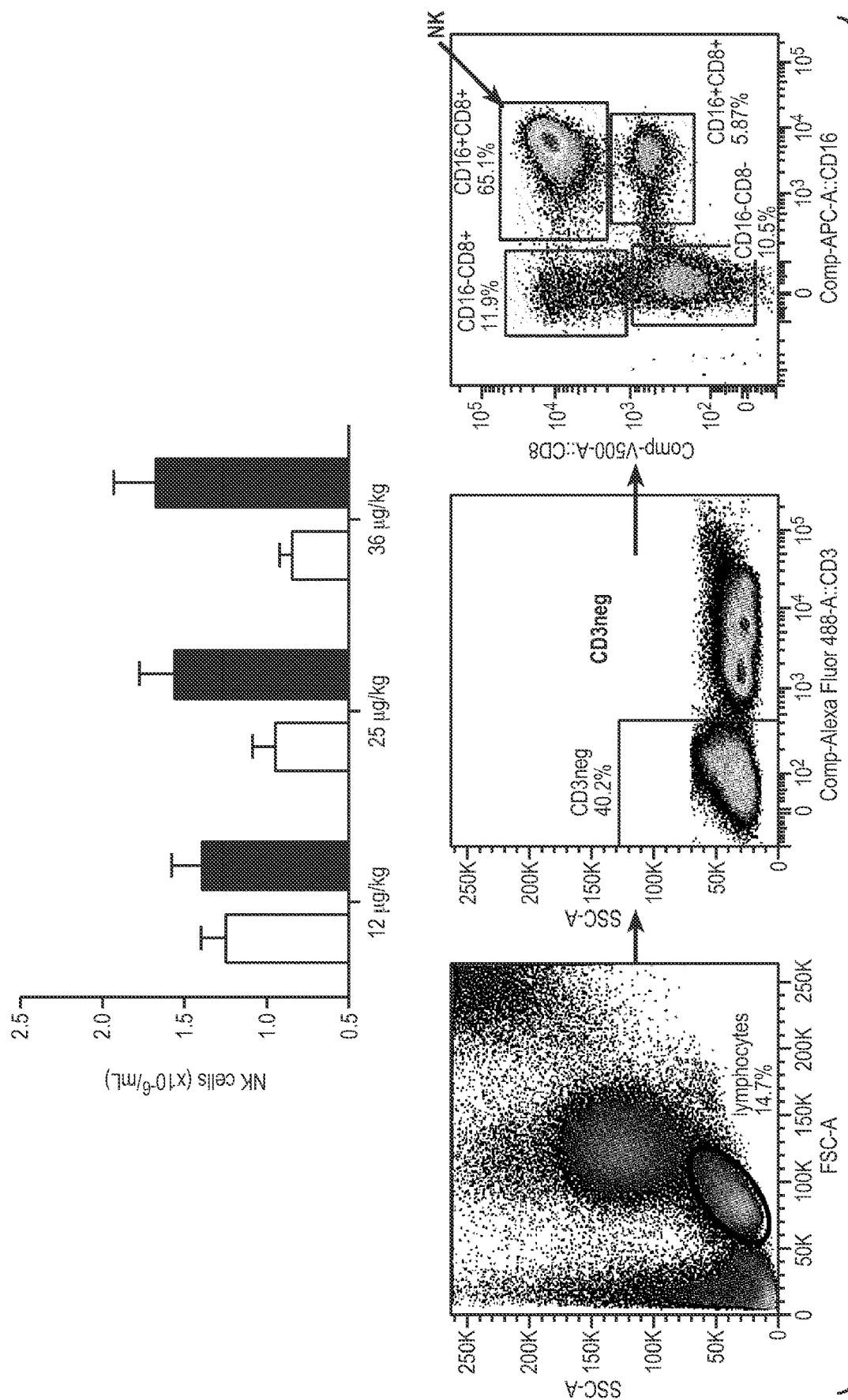
FIG. 10. Dose dependent effects of DP47 IgG-IL-2 on Natural Killer cells. NK cells were identified as CD3−, CD8+ CD16+ as shown. Vehicle treated monkeys (n=3, open bars) and those treated with DP47 IgG-IL2 (n=6, shaded bars) are shown as total blood NK cells (×10$^{-6}$ per ml).

In the DP47GS IgG-IL2 dose response test outlined above (FIG. 9) cynomolgus Nature Killer cells (NK) were also examined for treatment related changes. Cynomolgus NK cells are not CD56$^+$ so an alternative staining strategy was used to define NK cells in cynomolgus blood; a panel of CD3-Alexa Fluor® 488 (clone: SP34-2, BD Biosciences), CD16-APC (clone: 3G8, BD Biosciences), and CD8-V500 (clone: SKI, BD Biosciences) was used to stain another set of blood samples with NK cells identified as CD3$^-$, CD8$^+$ CD16$^+$ as shown. Vehicle treated monkeys (n=3) and those treated with DP47GS IgG-IL-2 (n=6) are shown in FIG. 9 as total blood NK cells (×10$^{-6}$ per ml). Importantly, at the 12 μg/kg dose, no increase in NK cells was observed. At the higher doses of 25 μg/kg and 36 μg/kg DP47GS IgG-IL-2, average NK increases of approximately 2-fold and 3-fold (range of 110-470%), respectively, were observed (FIG. 10). These data strongly support the hypothesis that low dose IL-2 can preferentially stimulate increases in $T_{reg}$ numbers in vivo.

Figure 11:
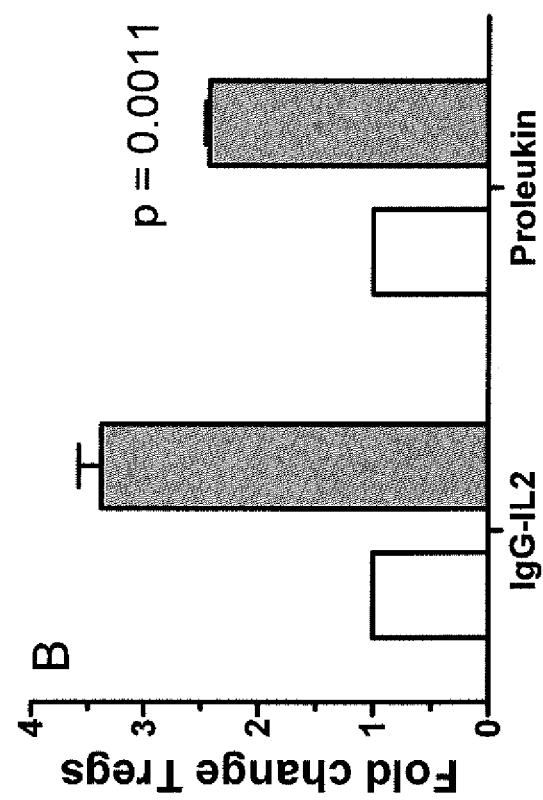
FIG. 11. Low dose DP47GS IgG-IL-2 is more effective than high dose Proleukin in T$_{reg}$ induction in cynomolgus monkeys. Normal healthy cynomolgus monkeys (groups of n=5) were treated with low doses of DP47GS IgG-IL-2 or high doses of Proleukin and the change in regulatory T cells tested at day 10. On days 0 and 7, DP47GS IgG-IL-2 was given SC at a dose of 16,800 IU/kg. Proleukin treatment was given SC 3 times per week (MWF) for a total of 5 doses at 200,000 IU/kg. The results are shown as mean±SEM for the change in total T$_{reg}$s per mm$^3$ blood (A), the fold increase in T$_{reg}$s (B), and the change in the ratio of T$_{reg}$s to conventional CD4+ FoxP3− cells (C). Shaded bars: IL-2 treatment; open bars: vehicle control.
Figure 11:
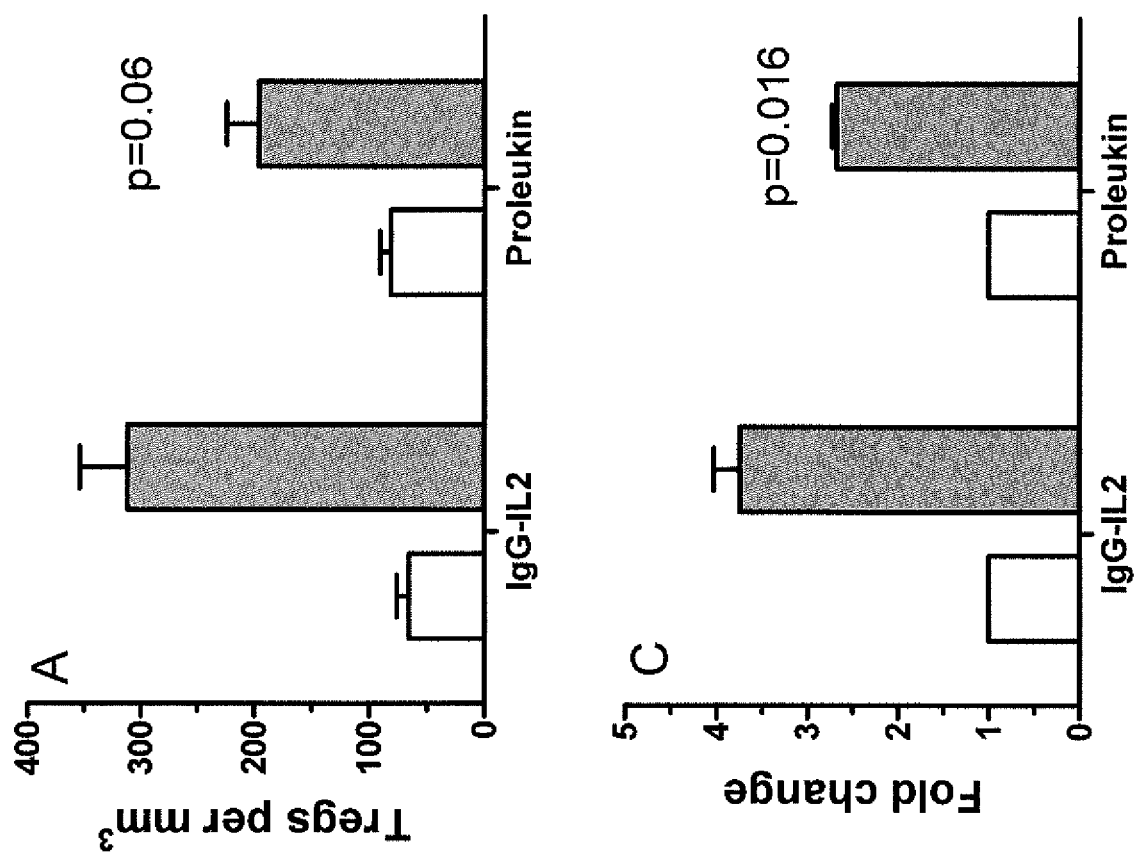

A comparison of the ability of DP47GS IgG-IL-2 to induce an increase in Tregs in vivo in cynomolgus monkeys with that of Proleukin is shown in FIG. 11. Normal healthy cynomolgus monkeys (groups of n=5) were treated with low doses of DP4705 IgG-IL-2 or high doses of Proleukin and the change in regulatory cells tested at day 10. On days 0 and 7, DP47 IgG-IL-2 was given SC at a dose of 16,800 IU/kg. Proleukin treatment was given SC 3 times per week (MWF) for a total of 5 doses at 200,000 IU/kg. The results are shown in FIG. 11 as mean±SEM for the change in total $T_{reg}$s per mm$^3$ blood (FIG. 11A), the fold increase in $T_{reg}$s (FIG. 11B), and the change in the ratio of $T_{reg}$s to conventional CD4$^+$ FoxP3$^-$ cells (FIG. 11C).

Because of the short half-life of Proleukin (see FIG. 14), it is normally dosed 5 days per week in humans. Therefore, during a 10 day study of $T_{reg}$ induction comparing DP47GS IgG-IL-2 and Proleukin, two doses of 16,800 IU/kg of DP47GS IgG-IL-2 (12 μg/kg) were administered (days 0 and 7) whereas five doses (days 0, 2, 4, 7, 9) of Proleukin at 200,000 IU/kg were given. The dose of Proleukin was based on an extrapolation from human studies where $T_{reg}$ numbers had been shown to be increased following the administration of Proleukin. Although nearly 30-fold less units of DP47GS IgG-IL-2 activity were administered over the 10 day period, DP47GS IgG-IL-2 induced a larger increase in the number of $T_{reg}$s than Proleukin (FIG. 11A, p=0.06). The increase of $T_{reg}$s above baseline (FIG. 11B) and the increase of $T_{reg}$ cells relative to conventional CD4 T cells (FIG. 11C) were also larger (p=0.0011 and p=0.016, respectively) in animals dosed with DP47GS IgG-IL-2 as compared to Proleukin. In humans the ratio of regulatory CD4 T cells (usually defined as Foxp3$^+$ or by a combination of surface markers) non-regulatory CD4 T cells (referred to as conventional or effector cells) is often used to define the functional levels of $T_{reg}$s in patients through time.

In Vivo Response of Cynomolgus Peripheral Blood Cell Subsets to Low Dose DP47GS IgG-IL-2 Treatment The in vivo cellular specificity of low dose IL-2 treatment is a critical parameter. We have determined that in vivo cell activation induced by DP47GS IgG-IL-2 or Proleukin can be sensitively monitored by measuring pSTAT5a levels ex vivo at various times after dosing cynomolgus monkeys or mice. The in vivo response of all cell populations that can be monitored in vitro (FIGS. 5-7) can be examined ex vivo.

One and 3 days after in vivo administration of a single low dose of DP47GS IgG-IL-2 (12 μg/kg) to healthy cynomolgus monkeys whole blood was collected and tested for STAT5 phosphorylation as described above (experimental procedures to Table 3). Each monkey was bled on day 0 before treatment and the amount of STAT5 phosphorylation was measured and used individually to assess fold-changes post treatment. The fold change in pSTAT5 in $T_{reg}$s on days 1 and 3 is shown in FIG. 12A, the fold change in pSTAT5 in conventional CD4$^+$ CD45$^-$ memory T cells in FIG. 12B, and the fold change in pSTAT5 in naïve T cells is in FIG. 12C.

Figure 12:
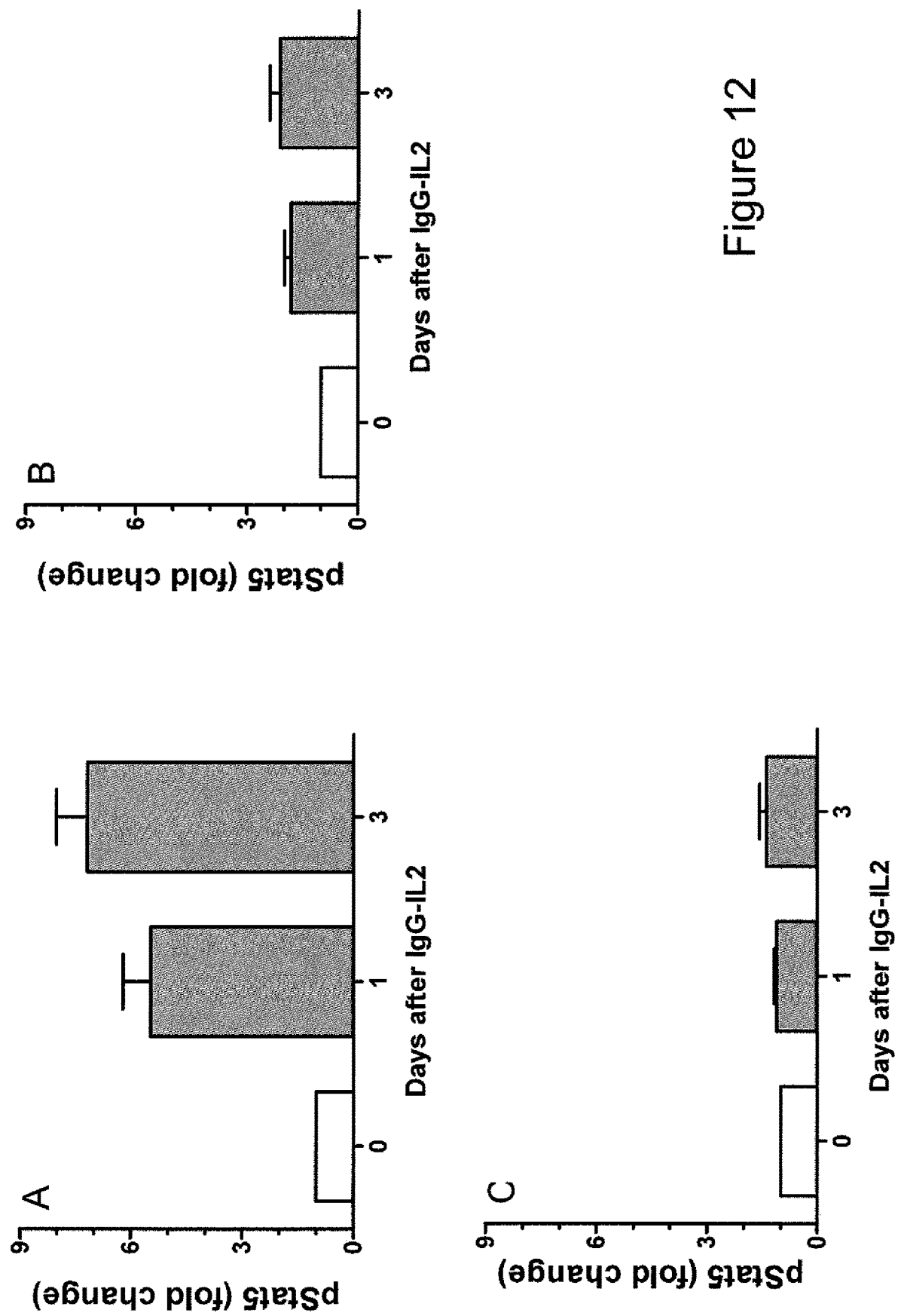
FIG. 12. Ex vivo whole blood pSTAT5 as a marker for DP47GS IgG-IL-2 T$_{reg}$ activation in vivo. One and 3 days after in vivo administration of a single low dose of DP47GS IgG-IL-2 (12 µg/kg) to healthy cynomolgus monkeys (n=5), whole blood was collected and tested for STAT5. Each monkey was bleed on day 0 before treatment and the amount of STAT5 phosphorylation was measured (open bars) and used individually to assess fold-changes post treatment (shaded bars). The fold change in pSTAT5 in T$_{reg}$s on days 1 and 3 (A), the fold Change in pSTAT5 in conventional CD4+ CD45− memory T cells (B), and the fold change in pSTAT5 in naïve T cells (C) is shown.

Cynomolgus blood cells obtained one and three days after a single low dose of DP47GS IgG-IL-2 (12 μg/kg) showed preferential pSTAT5a increases in $T_{reg}$ cells as compared to naïve and memory conventional CD4+ T cells (FIG. 12).

Figure 13:
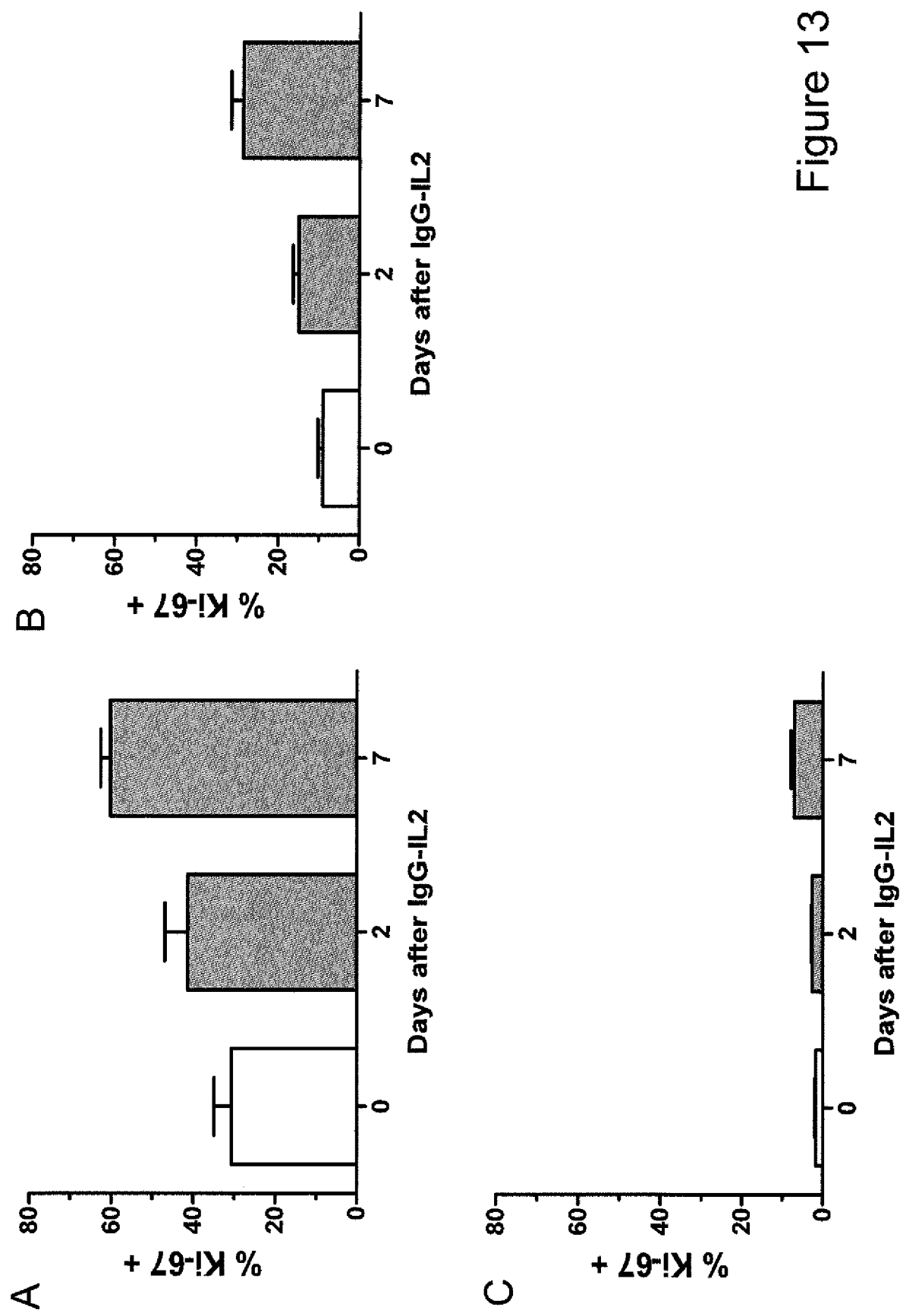
FIG. 13. Ex vivo whole blood Ki-67 as a marker for DP47GS IgG-IL-2 T cell proliferation in vivo. The cynomolgus monkeys treated with DP47GS IgG-IL-2 as described in FIG. 11 were also monitored for ex vivo changes in the intracellular marker Ki-67 to assess the extent of proliferation in vivo. The percentage of cells that were in cell cycle (Ki-67+) on day 0 (open bars) is compared to the percentage of cells Ki-67+ at 2 and 7 days post treatment (shaded bars). Ki-67+ T$_{reg}$s (A), conventional CD4+ CD45− memory T cells (B), and naïve CD4+CD45RA+ T cells (C) are shown.

The increase in $T_{reg}$ cells in the peripheral blood after low dose IL-2 treatment could reflect a change in the distribution of the cells in the body rather than an actual increase of the cells. To substantiate that Treg increases in vivo are at least in part due to the induction of cell division by IL-2 treatment, the intracellular marker of proliferation Ki-67 was assessed. Ki-67 is a protein that can be detected in the nucleus during $G_1$, S, $G_2$, and mitosis but is absent from resting cells that are in the $G_0$ phase of the cell cycle. The cynomolgus monkeys treated with DP47GS IgG-IL-2 as described above (FIG. 12) were also monitored for ex vivo changes in the intracellular marker Ki-67 as described above (experimental procedures to Table 3) to assess the extent of proliferation in vivo. The percentage of cells that were in cell cycle (Ki-67+) on day 0 was compared to the percentage of cells Ki-67+ at 2 and 7 days post treatment. Ki-67+ $T_{reg}$s are shown in FIG. 13A, conventional CD4+CD45− memory T cells are in FIG. 13B, and naïe CD4+CD45RA+ T cells are in FIG. 13C. Cynomolgus blood cells obtained two and seven days after a single low dose of DP47GS IgG-IL-2 (12 μg/kg) showed preferential Ki-67 increases in $T_{reg}$ cells as compared to naïve and memory conventional CD4+ T cells (FIG. 13).

Pharmacokinetic Properties of DP47GS IgG-IL-2

Figure 14:
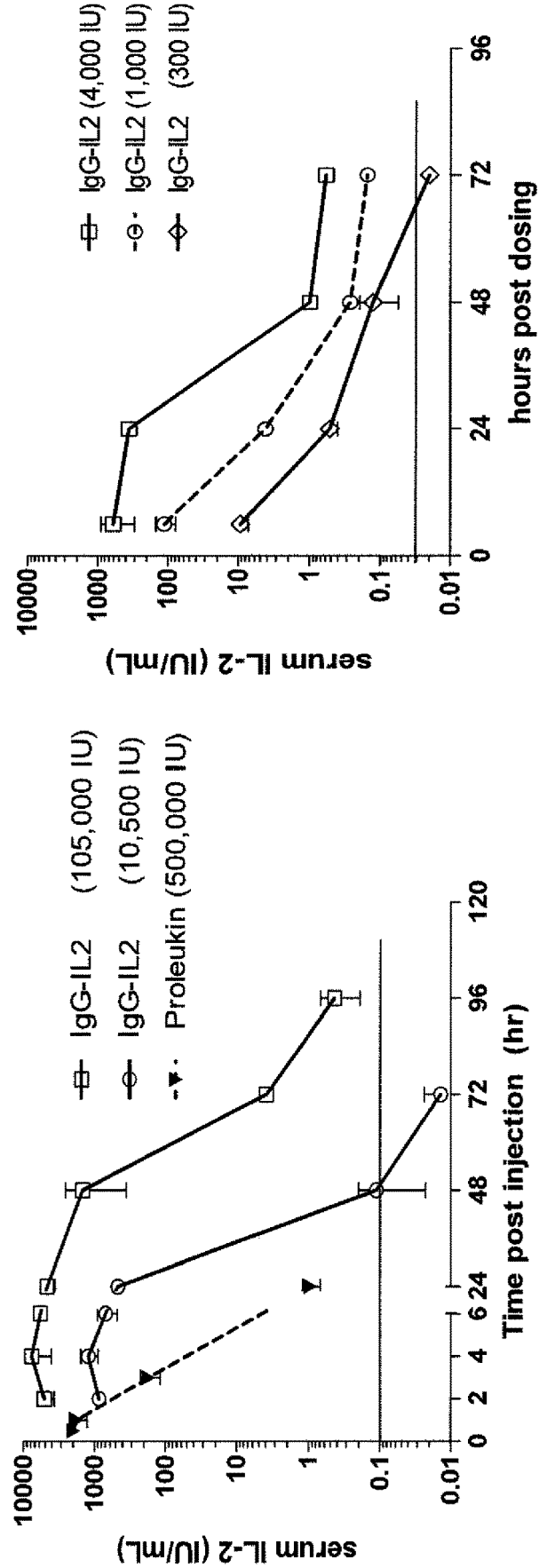
FIG. 14. DP47GS IgG-IL-2 has enhanced PK properties compared to Proleukin. NOD mice were injected IP (left panel) or SC (right panel) with the indicated doses of DP47GS IgG-IL-2 or Proleukin. Human IL-2 was assessed in serum samples at the indicated times.

Prior to beginning functional studies in mice, the pharmacokinetic properties of the immunoconjugate DP47 IgG-IL-2 were compared to those of Proleukin (Novartis) (FIG. 14).

NOD mice were injected IP or SC with the indicated doses of DP47GS IgG-IL-2 or Proleukin in PBS containing 0.5% mouse serum and bled at various times after the injections. Doses of DP47GS IgG-IL-2 are summarized in Table 4. Human IL-2 was assessed in serum samples using mouse anti-human IL-2 mAb, BD Pharmingen, Cat #555051, clone 5344.111 to coat 96-well plates to capture the IL-2. IL-2 was detected using biotinylated mouse anti-human IL-2 mAb, BD Pharmingen, Cat #555040, clone B33-2. Binding was visualized using Europium-conjugated streptavidin.

As described previously, Proleukin is cleared rapidly. In contrast, DP47GS IgG-IL-2 is cleared much more slowly. Results from comparing the PK of DP47GS IgG-IL-2 in normal mice and CD25KO scid mice support the hypothesis that a major component driving the in vivo clearance of DP47GS IgG-IL-2 is the high affinity IL-2 receptor (data not shown).

TABLE 4

Doses of DP47GS IgG-IL-2 for PK study shown in FIG. 14.

| IgG-IL2 IU/25 g | IgG-IL2 mg/kg |
| --- | --- |
| 105,000 | 3.0 |
| 10,500 | 0.3 |
| 4,000 | 0.114 |
| 1,000 | 0.0286 |
| 300 | 0.0086 |

Foxp3 and CD25 MFI Increase in $T_{reg}$s After Treatment with IgG-IL-2

To compare the abilities of the immunoconjugate DP47GS IgG-IL-2 and recombinant human IL-2 to stimulate Foxp3+ Treg cells in vivo, mice were injected subcutaneously with either Proleukin (Novartis, 4,000 or 40,000 or DP47 IgG-IL-2 (4,000 IU) and Tregs were monitored for changes in the expression of CD25 and Foxp3 one and three days later (FIG. 5).

NOD mice (3 mice/treatment group, including control cohorts at 24 and 72 h) were injected subcutaneously with either Proleukin (Novartis, 4,000 or 40,000 IU) or DP47GS IgG-IL-2 (4,000 IU). Doses were delivered in 100 μl sterile PBS pH 7.2 containing 0.5% sterile-filtered mouse serum. After 24 and 72 h mice were euthanized by cervical dislocation and spleens excised. A single cell suspension of splenocytes was generated in 1 ml L-15 media and stored on ice, until further processing. A filtered aliquot of the single cell suspension, 40 μl, was transferred to FACS tubes and washed with 2 ml FACS buffer (600×g, 5 min). Samples were then incubated with fluorochrome-conjugated antibodies directed against cell surface antigens: CD4 (clone RM4-5, fluorochrome A700), CD25 (eBio7D4, Af488), CD44 (IM7, e605), CD62L (MEL-14, PE), ICOS (C398.4A, PE/Cy7), CD103 (2E7, APC). Staining was performed for 30 min, at 4° C. in 100 μl FACS buffer (PBS pH 7.2+0.2% BSA). Following cell surface staining, samples were washed with 4 ml FACS buffer (600×g, 5 min) before intracellular staining (according to the eBioscience intracellular staining protocol). Briefly, samples were resuspended in 200 μl fixation/permeabilization buffer (eBioscience #00-5521) and incubated for 1 h, 4° C. 1 ml of 1× permeabilization buffer (eBioscience #00-8333) was added to samples before 3 ml PACS buffer and washing (600×g, 5 min). Intracellular antigens, Ki67 (B56, PerCP Cy5.5) and Foxp3 (FJK-16S, e450), were stained in 100 μl 1× permeabilization buffer for 1 h, 4° C. Samples were washed with 4 ml FACS buffer (600×g, 5 min—twice) and data acquired on a BD Fortessa Analyser and analysed using FlowJo software (Tree Star Inc.). $T_{reg}$s were defined as CD4+, Foxp3+ from singlets within the lymphocyte gate; from this population, CD25 and Foxp3 mean fluorescence intensity (MFI) were calculated for all samples.

Figure 15:
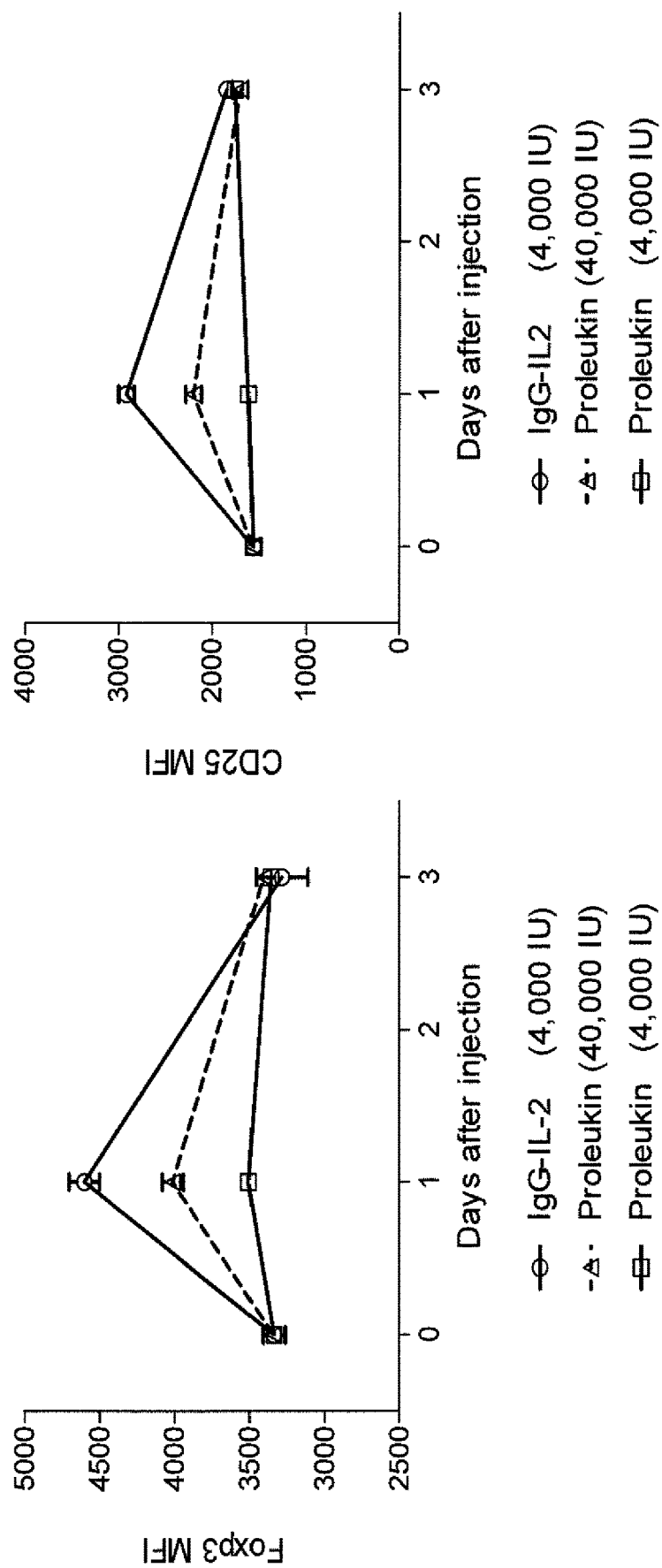
FIG. 15. Foxp3 and CD25 MFI increase in T$_{reg}$s after treatment with IgG-IL-2. NOD mice (3 mice/treatment group, including control cohorts at 24 and 72 h) were treated with either Proleukin (Novartis, 4,000 or 40,000 IU) or DP47GS IgG-IL-2 (4,000 IU), and cell surface antigen levels on splenocytes determined after 24 and 72 h by FACS. T$_{reg}$s were defined as CD4+, Foxp3+ from singlets within the lymphocyte gate; from this population, CD25 (right panel) and Foxp3 (left panel) mean fluorescence intensity (MFI) were calculated for all samples.

As shown in FIG. 15, 4,000 IU DP47 IgG-IL-2 induced greater up-regulation of Foxp3 and CD25 compared to 40,000 Proleukin. There was no significant increase in Foxp3 or CD25 expression when mice were treated with 4,000 IU Proleukin. In all treatment groups, Foxp3 and CD25 levels returned to baseline 72 h after IL-2 treatment.

In Vivo Treatment with DP47GS IgG-IL-2 Suppresses Immune Responses in Mice

Figure 16:
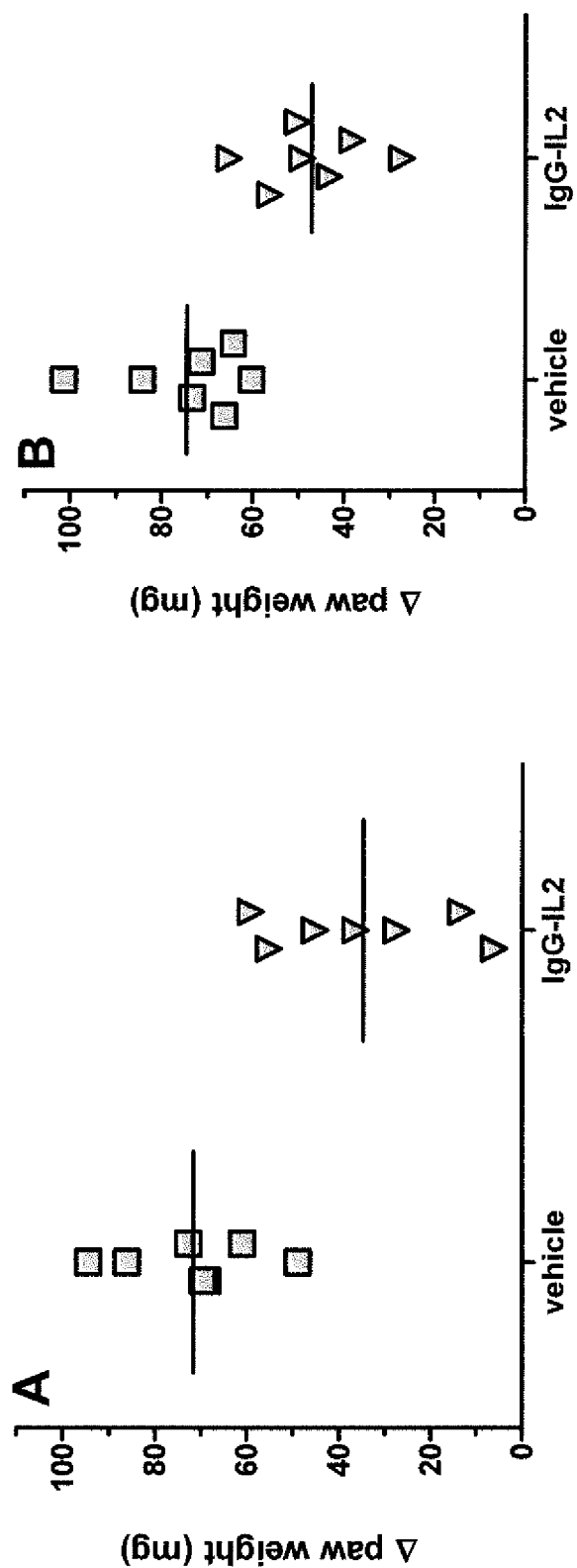
FIG. 16. In vivo treatment with DP47GS IgG-IL-2 suppresses murine delayed type hypersensitivity. Left panel: NOD mice, right panel: C57B/6 mice. The magnitude of the DTH response is shown as the change in paw weight compared to non-immunized mice (Δ paw weight).
Figure 17:
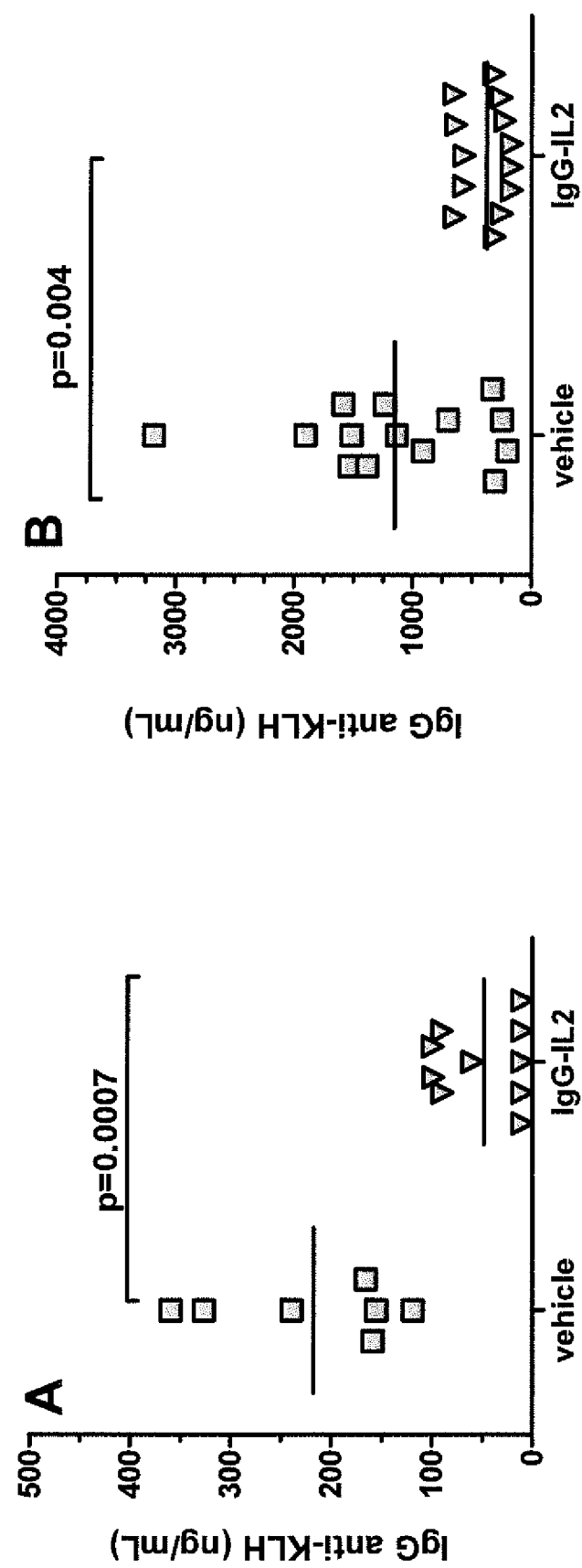
FIG. 17. In vivo treatment with DP47GS IgG-IL-2 suppresses the murine antibody responses to KLH.

Since we observed that a 4,000 IU DP47GS dose activated mouse Foxp3+ regulatory T cells in vivo, this dose was used to assess its ability to suppress immune responses in mice (FIGS. 16 and 17).

NOD mice and C57BL/6 mice (n=7) were immunized IV with sheep red blood cells (srbc) and challenged 3 days later with a bolus of srbc in a single hind foot to induce a delayed type hypersensitivity (DTH) response. One day after challenge, mice were euthanized with $CO_2$ and the paws excised and weighed. The magnitude of the DTH response is shown as the change in paw weight compared to non-immunized mice (Δ paw weight). DP47GS IgG-IL-2 was given SC at 4,000 IU per mouse 3 days before and on the day of srbc immunization and the vehicle was sterile PBS pH 7.2. Statistical significance was derived from the Mann Whitney test in GraphPad Prism.

Dosing DP47GS IgG-IL-2 three days before and on the day of sheep red blood cell immunization suppressed the subsequent delayed type hypersensitivity response to a sheep blood cell challenge by 51% in NOD mice (FIG. 16A; p-0.0023) and 38% in C57BL/6 mice (FIG. 16B; p=0.002).

DP47GS IgG-IL-2 was also able to suppress KLH-specific IgG responses in C57BL/6 (78% inhibition, p=0.0007, FIG. 17A) and NOD (67% inhibition, p=0.004, FIG. 17B) mice. For this experiment, healthy young C57BL/6 mice (n=7-10) and NOD mice (n=13-14) were immunized IP with 100 μg of human vaccine grade KLH without adjuvant as recommended by the manufacturer (Stellar). DP47GS IgG-IL-2 treatment consisted of 1 (NOD) or 2 (C57BL/6) weekly treatments with 4,000 IU per mouse SC initiated on the day of immunization. Seven days (NOD) and 21 days (C57BL/6) after immunization, blood was collected and serum KLH specific IgG responses were measured by ELISA.

The ability of DP47GS IgG-IL-2 to suppress immune responses in vivo supports the hypothesis that the regulatory T cell activation induced by low dose IL-2 produces functional regulatory T cells that mediate a reduction in the immune response.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for treating an autoimmune disease, said method comprising: administering a pharmaceutical composition comprising a fusion protein comprising
   (i) an immunoglobulin molecule comprising a modification reducing binding affinity of the immunoglobulin molecule to an Fc receptor as compared to a corresponding immunoglobulin molecule without said modification, and
   (ii) two interleukin-2 (IL-2) molecules to a patient,
   wherein said immunoglobulin molecule comprises the heavy chain variable region sequence of SEQ ID NO: 9 and the light chain variable region sequence of SEQ ID NO: 11, and wherein said immunoglobulin molecule comprises the amino acid substitutions L234A, L235A and P329G (EU numbering) in the immunoglobulin heavy chains,
   wherein said autoimmune disease is selected from the group consisting of type 1 diabetes, systemic lupus erythematosus, ulcerative colitis, Crohn's disease and multiple sclerosis.

2. The method of claim 1, wherein administration of said pharmaceutical composition comprises induction of IL-2 receptor signaling.

3. The method of claim 1, wherein administration of said pharmaceutical composition comprises induction proliferation of at least a subset of T cells.

4. The method of claim 2, wherein said method is in vitro and said fusion protein is used at a concentration of about 1 ng/mL or less, particularly about 0.1 ng/mL or less.

5. The method of claim 1, wherein said method is in vivo and said fusion protein is used at a dose of about 20 µg/kg body weight or less.

6. The method of claim 5, wherein said dose is less than or equal to about 12 µg/kg body weight.

* * * * *